United States Patent
Bruehwiler et al.

(10) Patent No.: US 9,107,988 B2
(45) Date of Patent: Aug. 18, 2015

(54) CIRCUITOUS BAND NEEDLE CHANGING APPARATUS

(75) Inventors: Michel Bruehwiler, Newton, MA (US); Cole Constantineau, Cambridge, MA (US); Ryan Schoonmaker, San Marcos, CA (US); James Bates, Sparta, NJ (US); Margaret Taylor, Groton, MA (US); Robert Banik, Long Valley, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1031 days.

(21) Appl. No.: 13/206,405

(22) Filed: Aug. 9, 2011

(65) Prior Publication Data

US 2012/0041383 A1 Feb. 16, 2012

Related U.S. Application Data

(60) Provisional application No. 61/344,526, filed on Aug. 16, 2010.

(51) Int. Cl.
*A61M 5/00* (2006.01)

(52) U.S. Cl.
CPC .......... *A61M 5/008* (2013.01); *A61M 2005/004* (2013.01)

(58) Field of Classification Search
CPC .................. A61M 2005/004; A61M 5/008
USPC .......................................... 604/192, 200, 240
See application file for complete search history.

(56) References Cited

U.S. PATENT DOCUMENTS

| | | | |
|---|---|---|---|
| 5,829,589 A * | 11/1998 | Nguyen et al. | 206/366 |
| 5,873,462 A * | 2/1999 | Nguyen et al. | 206/366 |
| 5,971,966 A | 10/1999 | Lav | |
| 6,616,616 B2 | 9/2003 | Fritz et al. | |
| 6,783,537 B1 | 8/2004 | Kuhr et al. | |
| 7,544,185 B2 | 6/2009 | Bengtsson | |
| 8,579,861 B2 * | 11/2013 | Radmer et al. | 604/173 |
| 2002/0020646 A1 | 2/2002 | Groth et al. | |
| 2003/0014018 A1 * | 1/2003 | Giambattista et al. | 604/198 |
| 2009/0227958 A1 | 9/2009 | Burroughs et al. | |
| 2012/0016315 A1 | 1/2012 | Radmer et al. | |

FOREIGN PATENT DOCUMENTS

| | | |
|---|---|---|
| JP | 2006-527622 A | 12/2006 |
| JP | 2007-531591 A | 11/2007 |
| WO | WO 2004/004812 | 1/2004 |
| WO | WO2005/097237 | 10/2005 |
| WO | WO2007/143323 | 12/2007 |
| WO | WO2009/016161 | 2/2009 |
| WO | WO 2009/016161 | 2/2009 |

* cited by examiner

*Primary Examiner* — Aarti B Berdichevsky
(74) *Attorney, Agent, or Firm* — Roylance, Abrams, Berdo & Goodman, L.L.P.

(57) ABSTRACT

An apparatus is disclosed for storing and changing needles for a medicament delivery device having a medicament container, including a fixed mount for connecting the apparatus with the medicament delivery device, a needle holder displaceable along a circuitous path and connecting a plurality of needles displaceably disposed thereon, and a guide member for guiding displacement of the needle holder, the guide member being disposed about the fixed mount. The apparatus also includes a user interface rotatably disposed about the fixed mount and having at least one internal engaging structure for displacing the needle holder along the circuitous path.

25 Claims, 55 Drawing Sheets

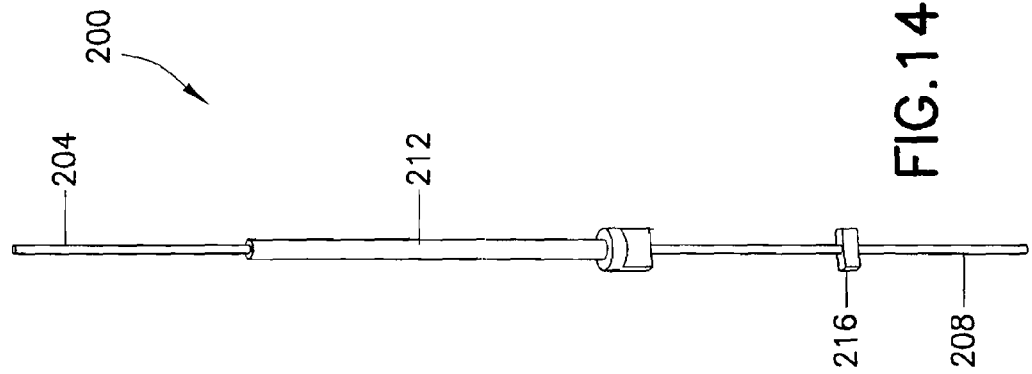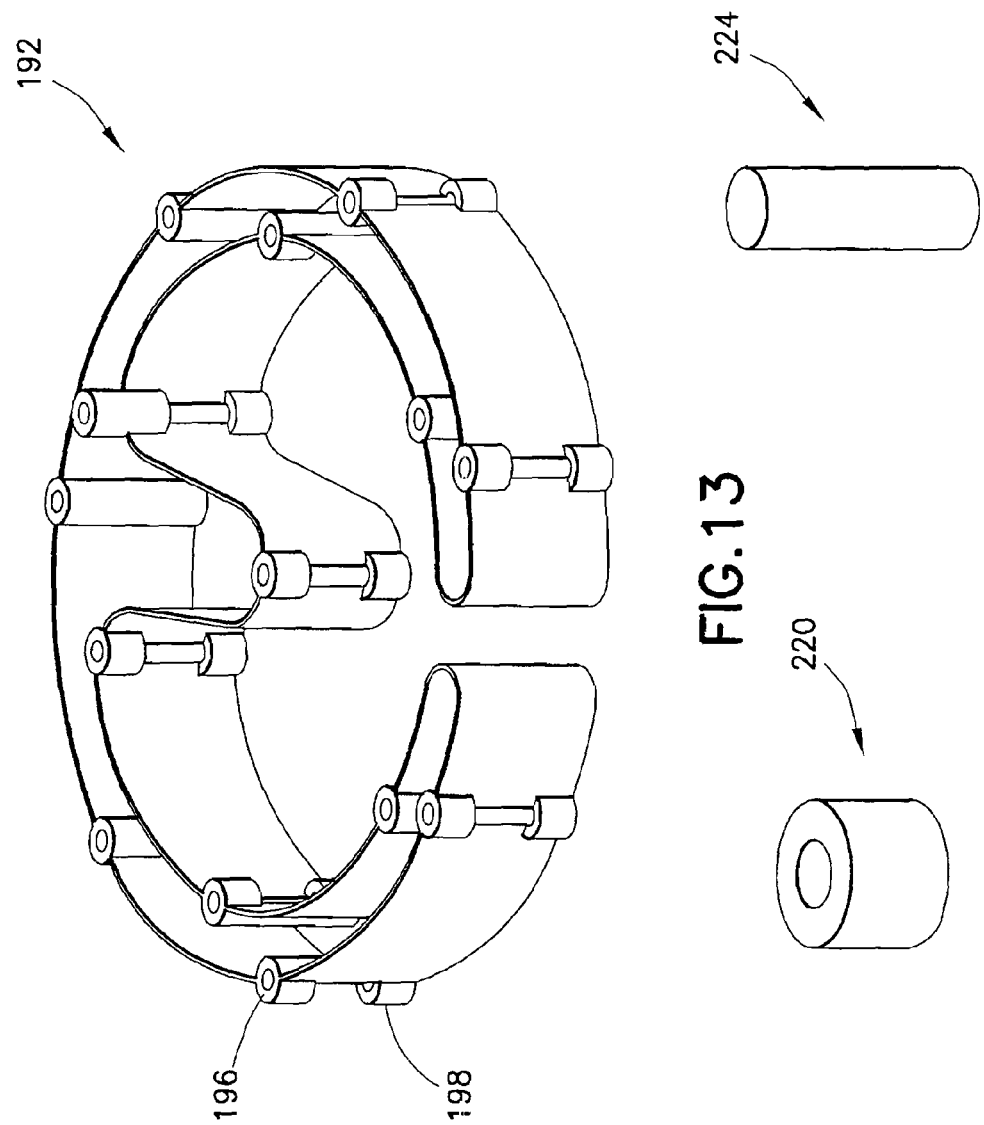

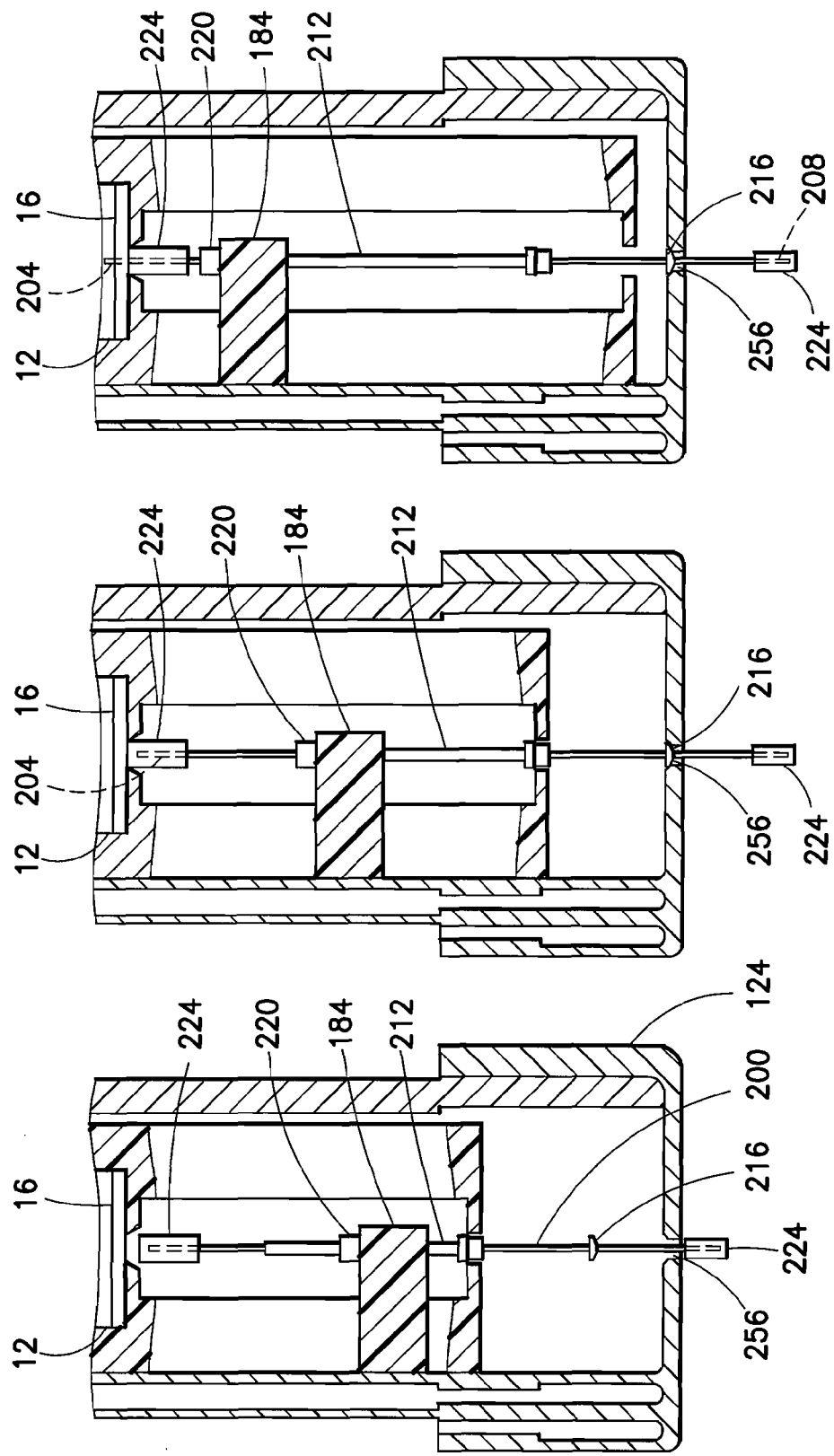

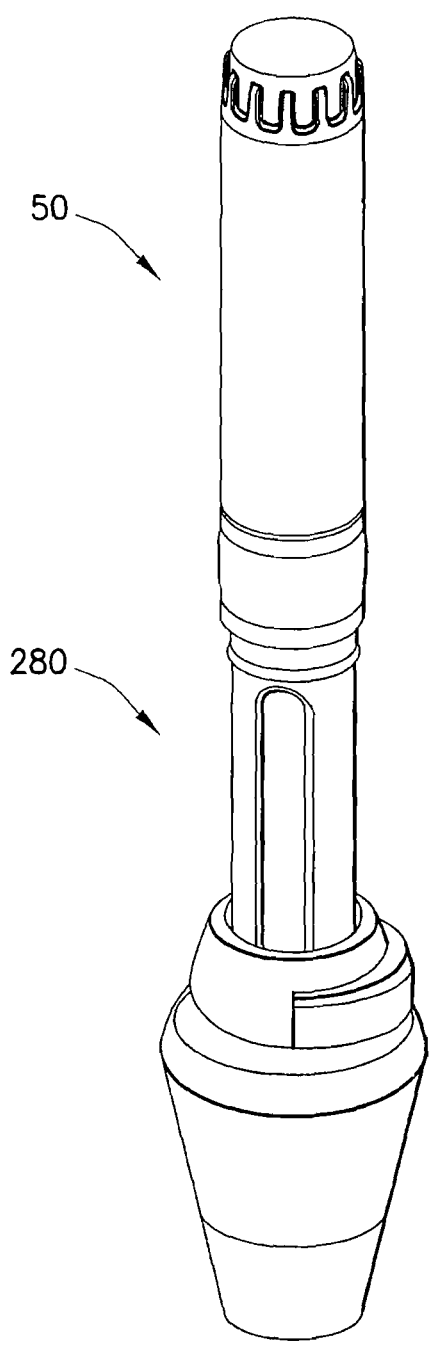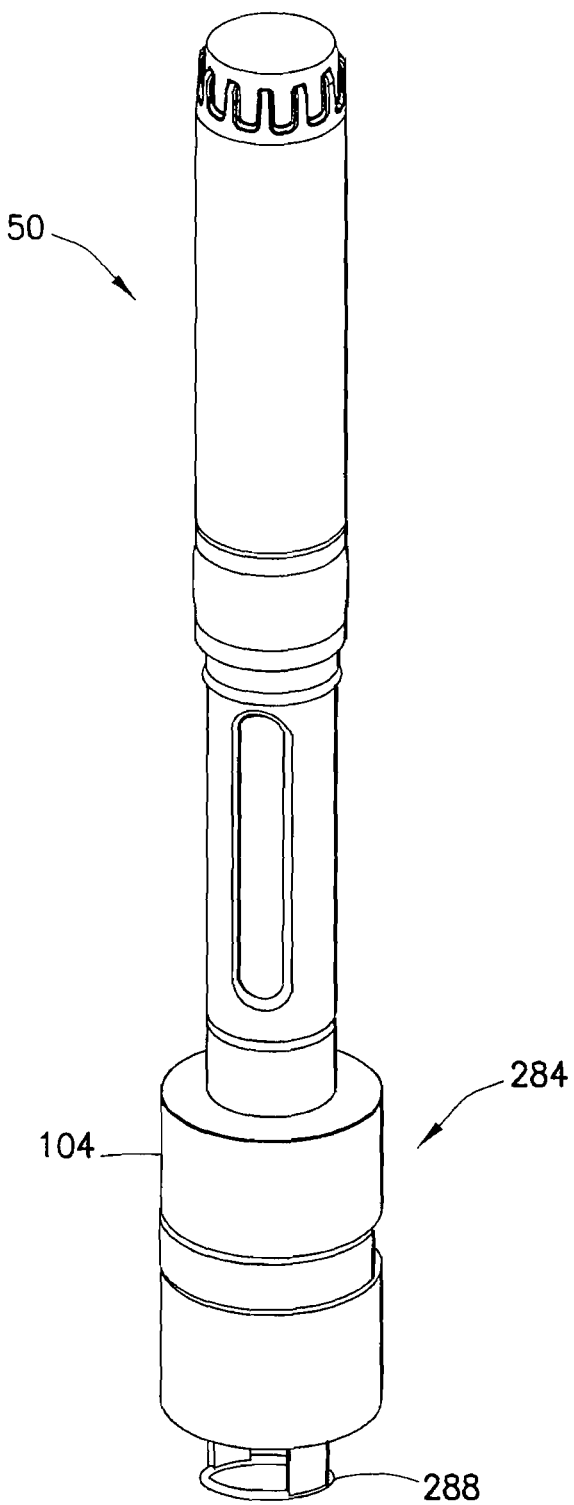
FIG.47
FIG.48

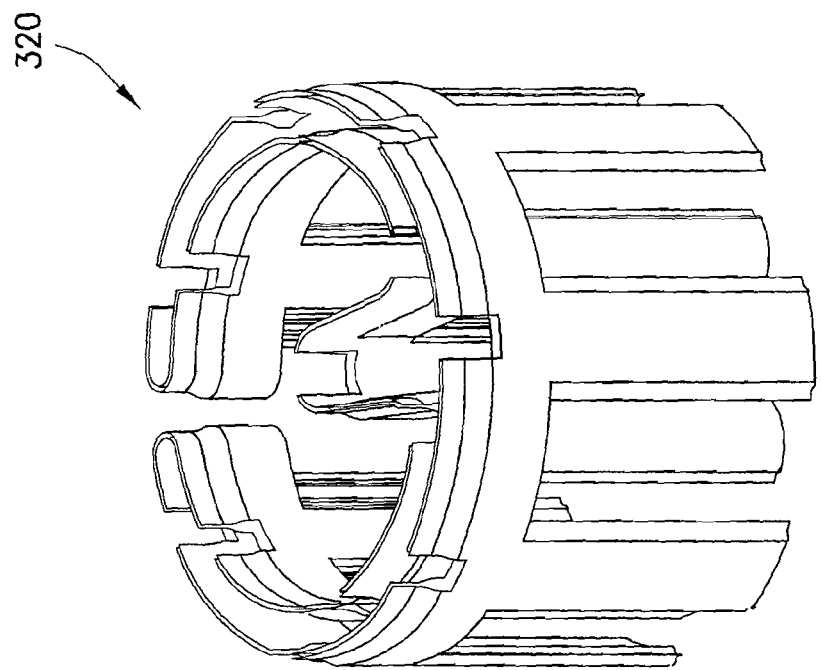
FIG.53
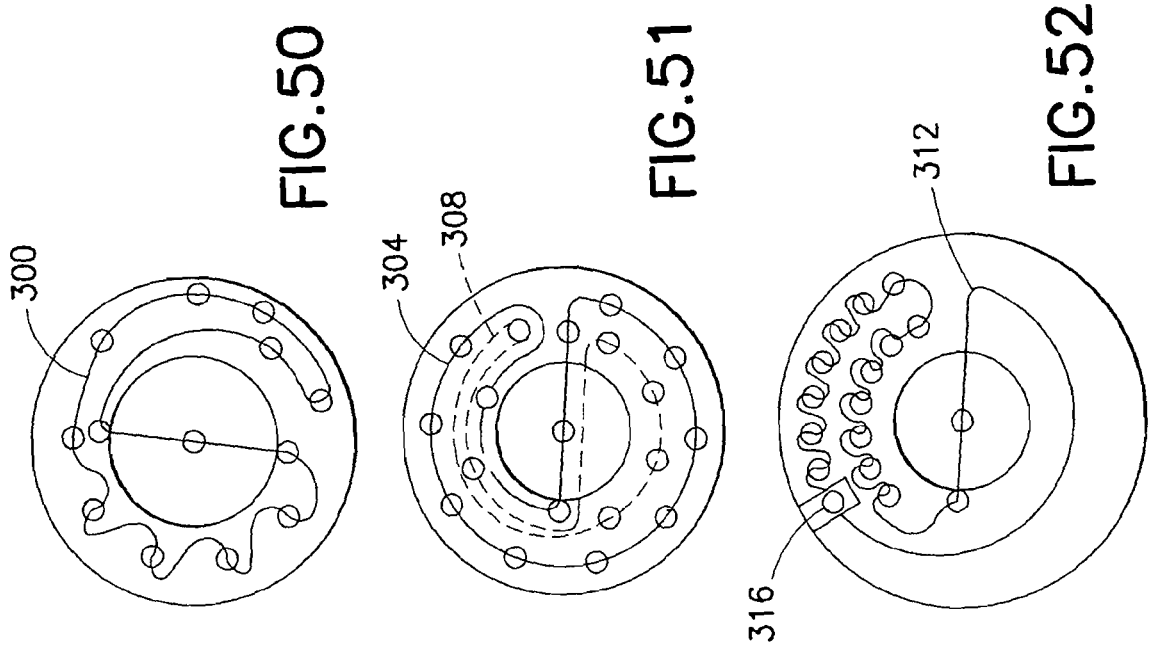
FIG.50
FIG.51
FIG.52

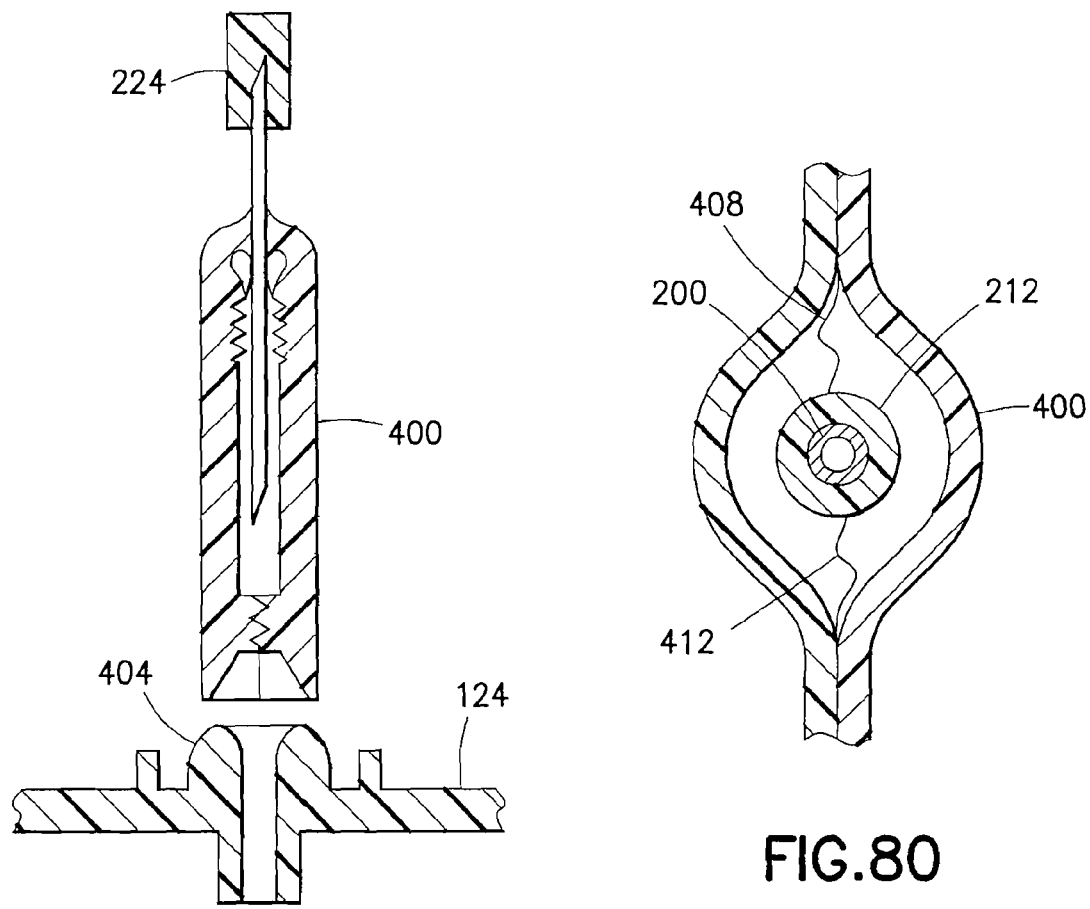
FIG.79
FIG.80
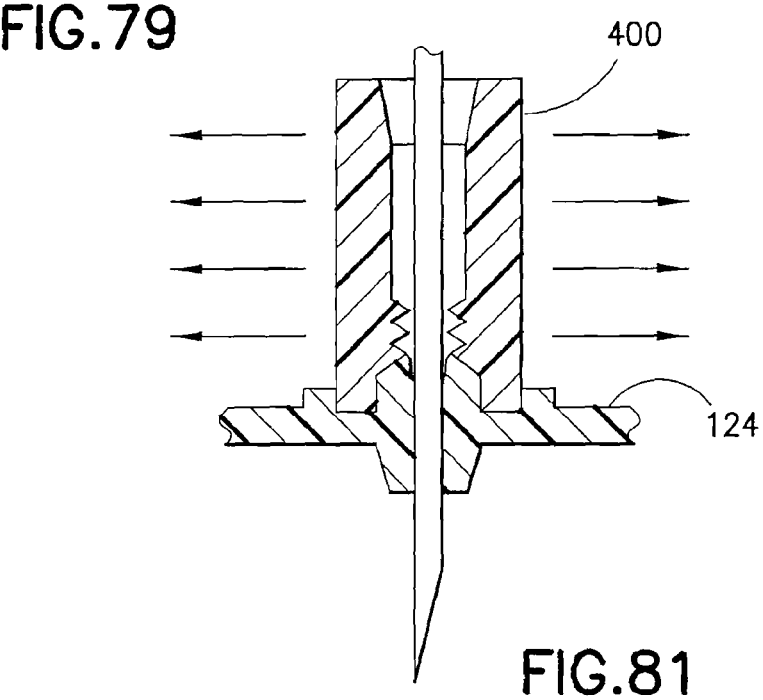
FIG.81

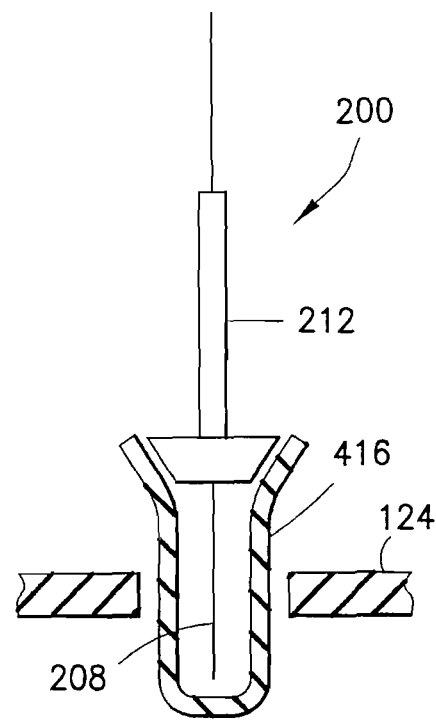
FIG.82
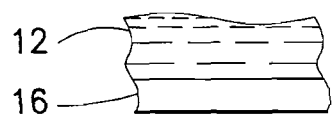
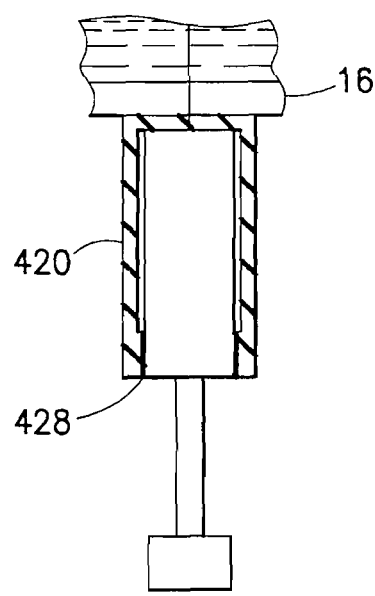
FIG.83
FIG.84

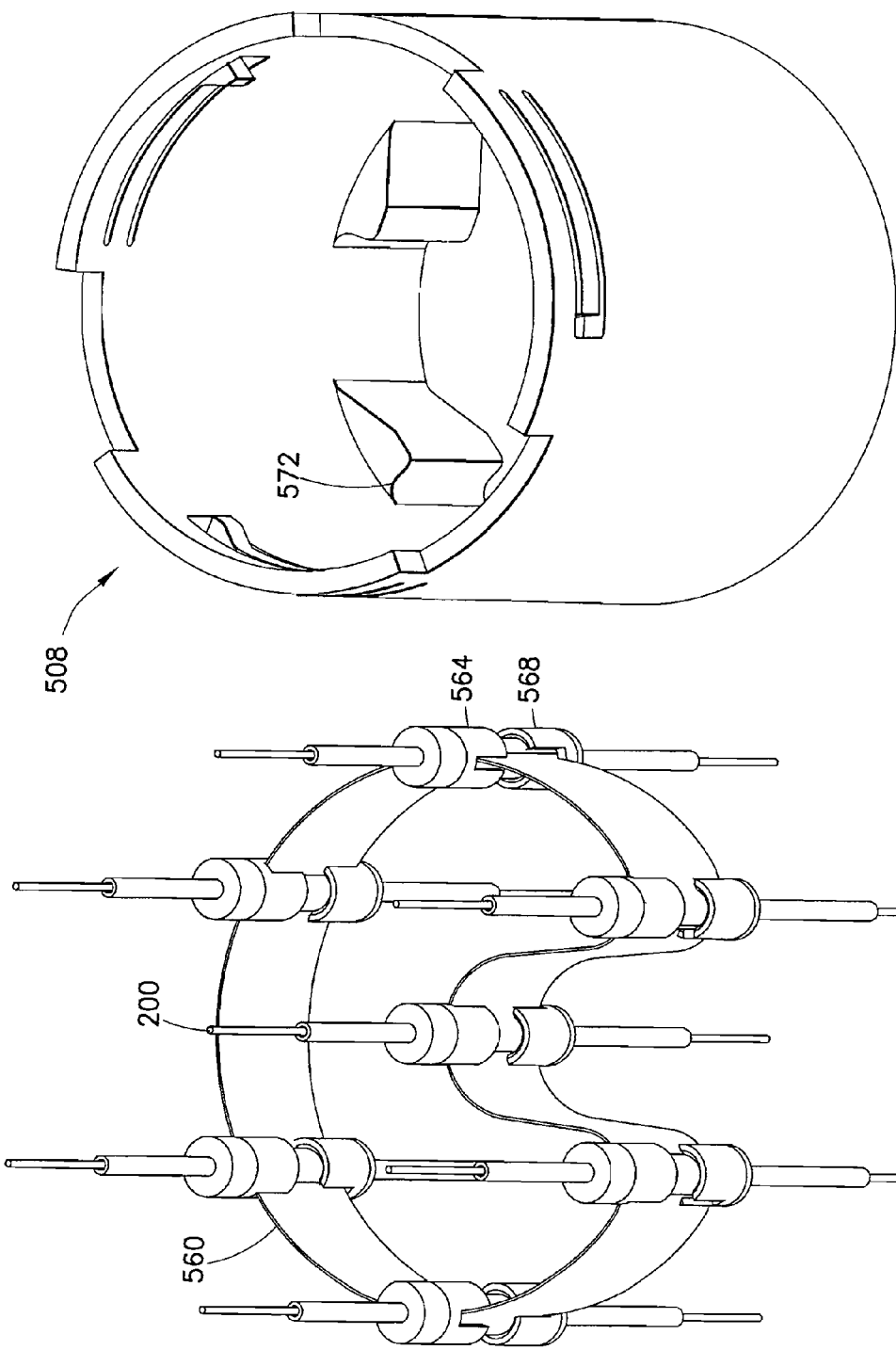

US 9,107,988 B2

CIRCUITOUS BAND NEEDLE CHANGING APPARATUS

CROSS-REFERENCE TO RELATED APPLICATIONS

This application claims priority under 35 USC §119(e) from U.S. Provisional Patent Application Ser. No. 61/344,526, filed on Aug. 16, 2010, the disclosure of which is incorporated herein by reference in its entirety.

BACKGROUND OF THE INVENTION

1. Field of the Invention

The present invention relates to needles for a medicament delivery device, such as a pen injection device or a syringe, and more particularly, to a multiple needle changing apparatus for a medicament delivery device.

2. Description of the Related Art

Medicament delivery devices are used for self-injection of precisely measured doses of medication. Pen injection devices are widely used, for example, by diabetics to self-inject insulin. A typical medicament delivery pen includes a cartridge that contains a volume of liquid medication sufficient for several doses. Using a pen needle attached to a pen injection device, the dose is injected into a tissue area, such as the intramuscular tissue layer, the subcutaneous tissue layer, or the intradermal tissue layer.

The assembly and operation of a typical pen injection device is described in commonly-assigned U.S. Patent Application Publication No. 2006/0229562, published on Oct. 12, 2006, which is hereby incorporated by reference in its entirety.

Pen injection devices, such as the exemplary pen injector 50 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art.

A pen needle assembly 10 includes a hub 20, a patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move with respect to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen injector 50, an outer shield 29, which attaches to the hub 20, covers the hub 20. The outer shield 29 can also be used as a handle or grip to screw hub 20 onto or off of pen injector 50. An inner shield 28 covers the patient needle 11 within the outer shield 29. The inner shield 28 can be secured to the hub 20 to cover the patient needle 11 by any suitable means, such as an interference fit or a snap fit. As shown in FIG. 2, the hub 20 also includes ribs 64 for engaging the outer shield 29. The outer shield 29 and inner shield 28 are removed prior to use. The cap 21 fits snugly against outer sleeve 13 to allow a user to securely carry the pen injection device 50.

To use the pen needle assembly 10, the user removes a sterile cover (not shown) on the outer shield 29, twists the pen needle assembly 10 onto the pen injector 50, removes the outer shield 29, and then finally removes the inner shield 28. While there are some needle storage devices that aid in placing the pen needle assembly 10 on the pen injector 50, the user still must remove needle hub packaging, including the inner and outer shields 28 and 29, to place a needle hub onto a pen injector and ready the device for injection. This process must be repeated for each successive injection.

Pen needle assemblies are usually sold individually packaged inside a plastic cover (such as outer shield 29) with a label covering the opening in the cover to provide a sterility barrier. A need exists for a needle dispensing and storing apparatus that stores a plurality of needles before and after their use.

SUMMARY OF EMBODIMENTS OF THE INVENTION

It is an aspect of the present invention to provide an apparatus for changing needles. It is also an aspect of the present invention to provide an apparatus for storing needles prior to their use as well as subsequent to their use. Additionally, it is an aspect of the present invention to provide an apparatus for changing needles for use with a medicament delivery device.

The foregoing and/or other aspects of the present invention are achieved by providing an apparatus for storing and changing needles for a medicament delivery device having a medicament container, including a fixed mount for connecting the apparatus with the medicament delivery device, a needle holder displaceable along a circuitous path and connecting a plurality of needles displaceably disposed thereon, and a guide member for guiding displacement of the needle holder, the guide member being disposed about the fixed mount. The apparatus also includes a user interface rotatably disposed about the fixed mount and having at least one internal engaging structure for displacing the needle holder along the circuitous path.

The foregoing and/or other aspects of the present invention are also achieved by providing a method of selecting a needle for a medicament delivery device having a medicament container, the method including the operations of connecting the medicament delivery device with an apparatus for storing and changing needles, rotating a user interface to displace one of a plurality of needles mounted in a needle holder along a circuitous path to an activated position, and also to displace a second user interface, and proximally sliding the user interface to expose a patient end of a needle outside of the apparatus and fluidly connect a non-patient end of the needle with the medicament container. The method also includes the operations of displacing the second user interface to advance a needle counter, and distally sliding the user interface to re-sheathe the patient end and disconnect the non-patient end from the medicament container.

The foregoing and/or other aspects of the present invention are also achieved by providing an apparatus for storing and changing needles for a medicament delivery device having a medicament container, including a fixed mount for connecting the apparatus with the medicament delivery device, and a guide member axially slidably disposed about the fixed mount, the fixed mount and the guide member forming at least a portion of a circuitous path. The apparatus also includes a needle holder displaceable along the circuitous path and connecting a plurality of needles displaceably disposed thereon, and a user interface rotatably disposed about the fixed mount and the guide member, and axially slidable relative to the fixed mount for sliding along with the guide member.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which:

FIG. 13 is a perspective view of a needle holder of the needle changing device of FIG. 3;

FIG. 14 is a perspective view of a needle of the needle changing device of FIG. 3;

FIG. 15 is a perspective view of a lock ring of the needle changing device of FIG. 3;

FIG. 16 is a perspective view of a sterility barrier of the needle changing device of FIG. 3;

FIGS. 42-44 are perspective cutaway views of the needle changing device of FIG. 3;

FIG. 47 is a perspective view of a needle changing device in accordance with another embodiment of the present invention;

FIG. 48 is a perspective view of a needle changing device in accordance with yet another embodiment of the present invention;

FIGS. 50-52 are partial plan views illustrating alternative embodiments of needle-holders;

FIG. 53 is a perspective view of an alternative sterility barrier for a patient end of a needle;

FIGS. 61-89 illustrate other alternative sterility barriers;

FIG. 97 is a perspective view of a needle holder 560 of the needle changing device of FIG. 90;

FIG. 98 is a perspective view of a user dial of the needle changing device of FIG. 90;

DETAILED DESCRIPTION OF EMBODIMENTS OF THE PRESENT INVENTION

Figure 1:
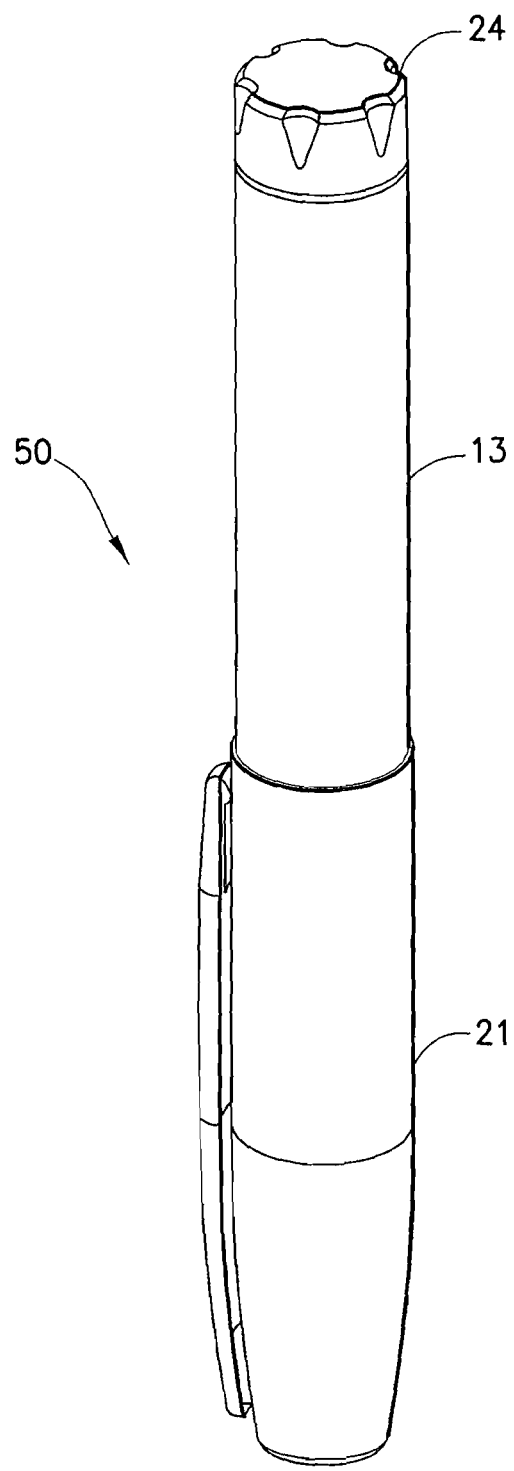
FIG. 1 is a perspective view of an exemplary drug delivery pen.
Figure 2:
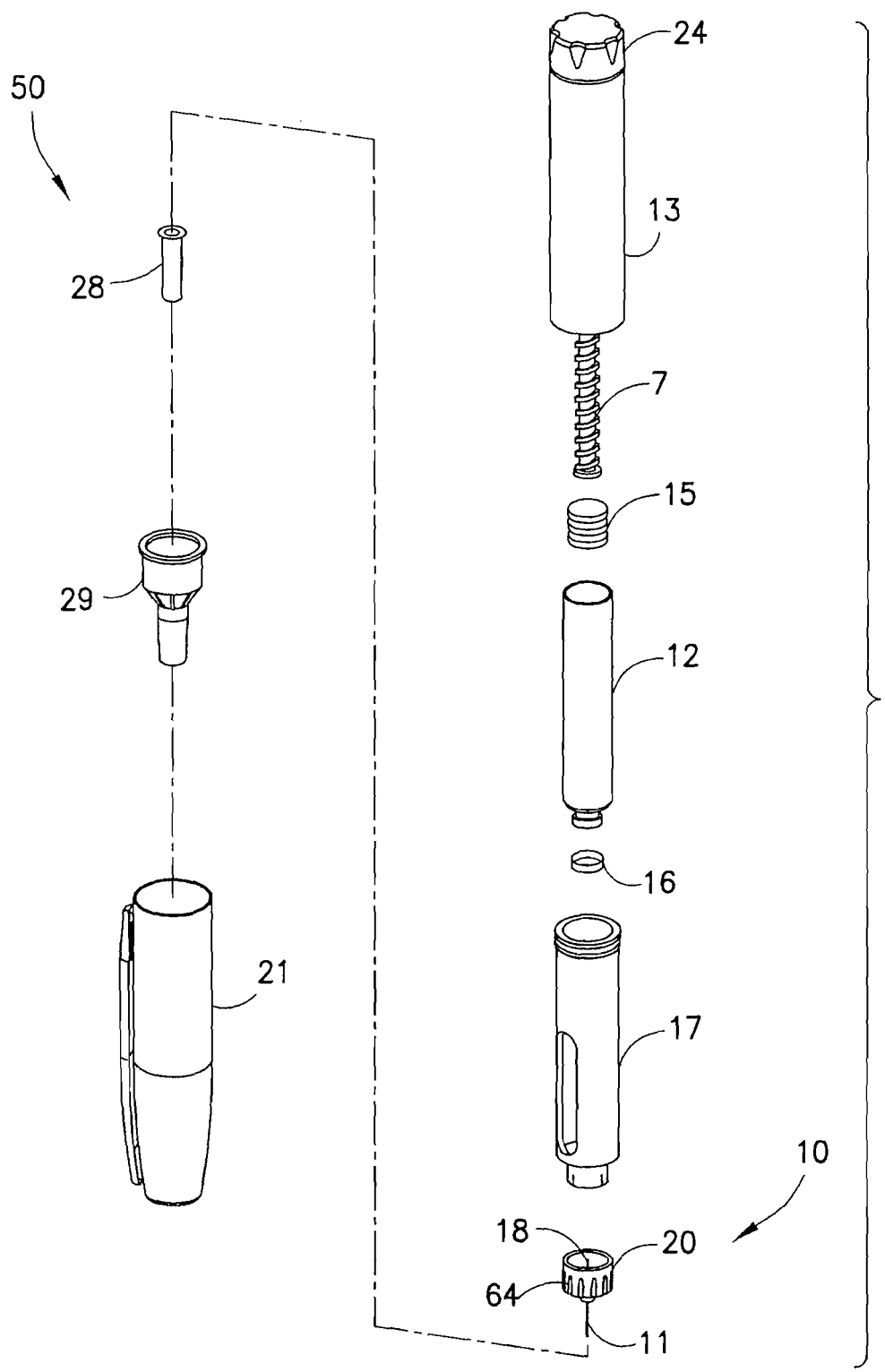
FIG. 2 is an exploded view of the exemplary drug delivery pen of FIG. 1.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 3:
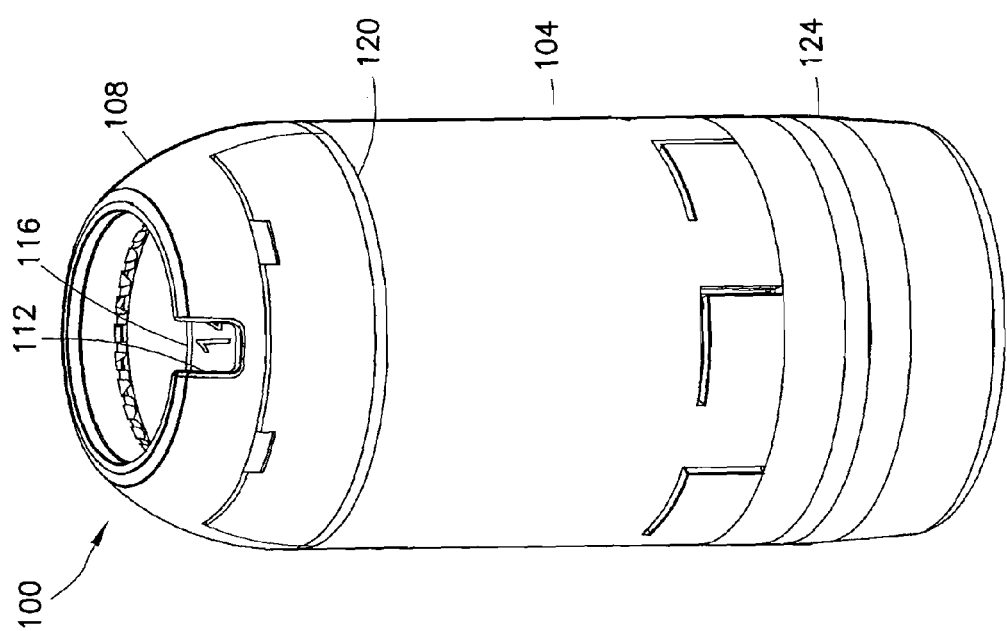
FIG. 3 is a perspective view of a needle changing device in accordance with an embodiment of the present invention.
Figure 28:
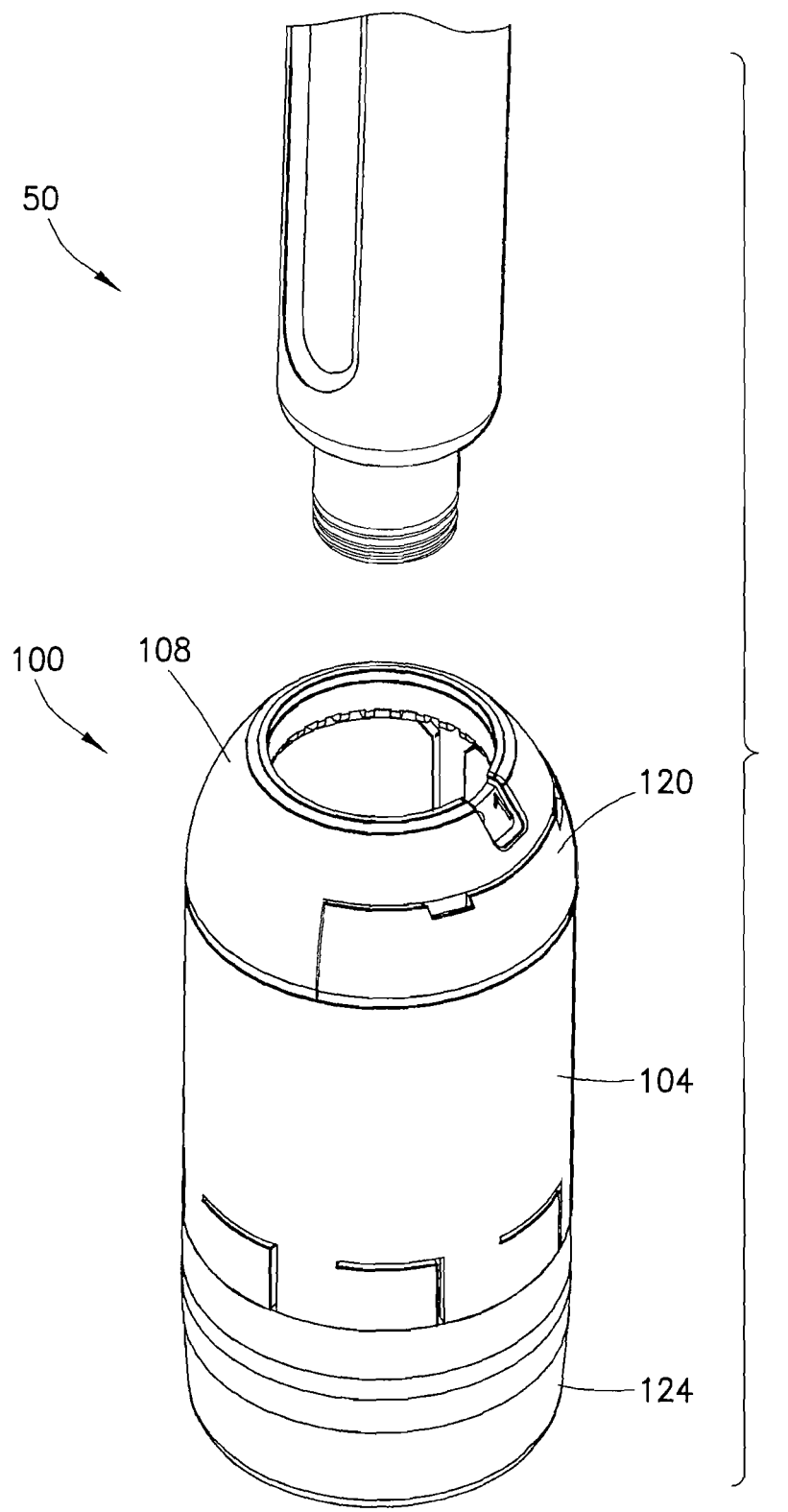
FIG. 28 is a perspective view illustrating assembly of the drug delivery pen of FIG. 1 and the needle changing device of FIG. 3.
Figure 29:
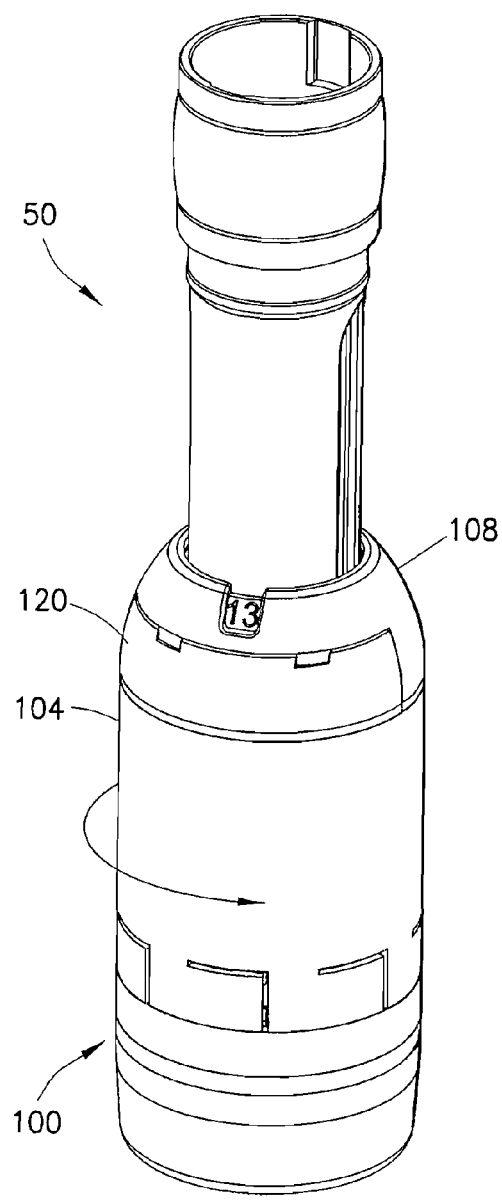
FIGS. 29-34 are perspective views illustrating operation of the needle changing device of FIG. 3.

FIG. 3 is a perspective view of a needle changing device 100 in accordance with an embodiment of the present invention. As shown in FIG. 28, the user combines the injector pen 50 and the changing device 100, for example, by screwing the pen injector 50 into the changing device 100. For brevity, the phrase "changing device 100" will be used hereinafter instead of "needle changing device 100." As shown in FIG. 3, the changing device 100 includes a user dial or user interface 104, a cap 108 that includes a cap window 112, a needle counter 116, a user button or second user interface 120, and an inner track or inner housing or bottom housing 124.

Figure 4:
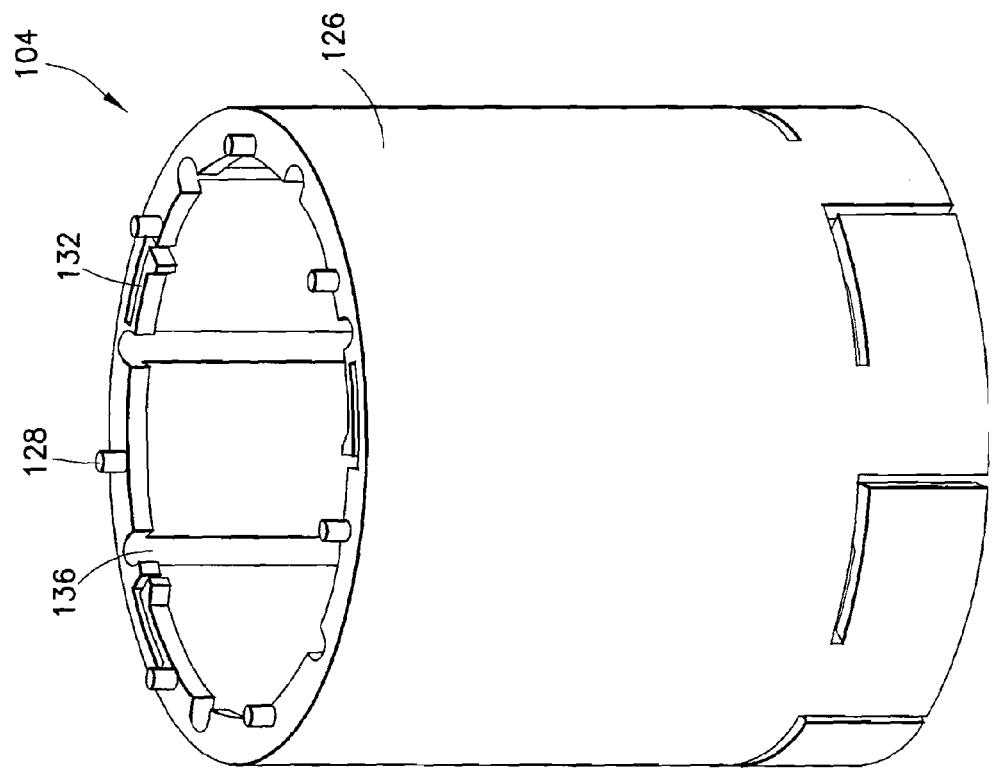
FIG. 4 is a perspective view of a user dial of the needle changing device of FIG. 3.

FIG. 4 is a perspective view of the user dial 104. The user dial 104 includes a user interface portion 126 for the user to grasp. The user dial 104 also includes a plurality of bosses 128 extending from a top surface thereof and a plurality of cantilevered engagement arms 132 extending inwardly from a top of the user dial 104. Additionally, the user dial 104 includes a plurality of internal engaging structures or rounded axial grooves 136 radially arrayed around an inner surface of the user dial 104.

Figure 5:
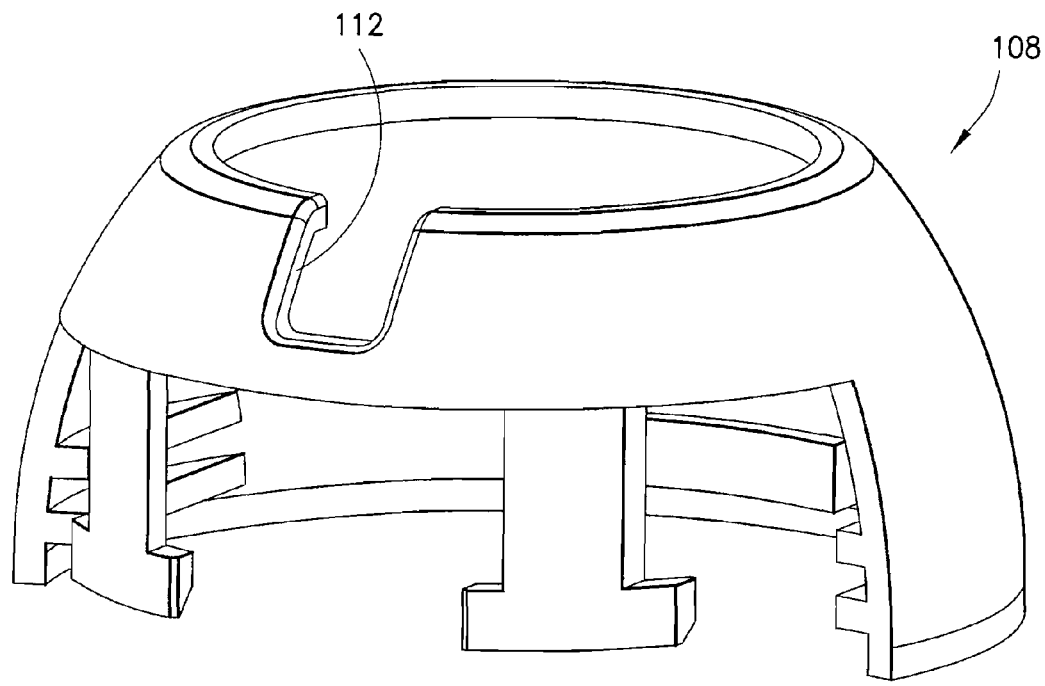
FIG. 5 is a perspective view of a cap of the needle changing device of FIG. 3.

FIG. 5 is a perspective view of the cap 108. The cap 108 includes the cap window 112 for a number on the needle counter 116 representing the number of the next unused needle. Although this embodiment of the present invention illustrates counting up with regard to the number of needles, one skilled in the art will understand that the numbers could count down the number of remaining unused needles without departing from the scope of the present invention.

Figure 6:
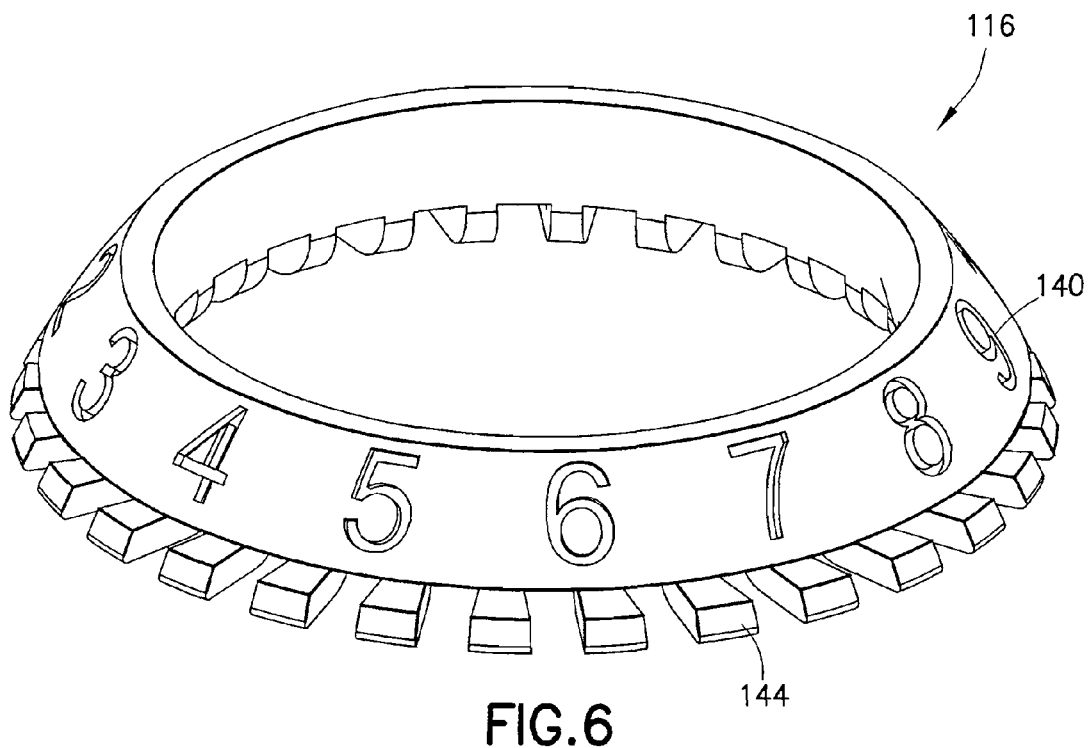
FIG. 6 is a perspective view of a needle counter of the needle changing device of FIG. 3.

FIG. 6 is a perspective view of the needle counter 116, which is rotatably disposed within the changing device 100. The needle counter 116 includes a plurality of identification numbers 140 for identifying the number of the next unused needle and a plurality of fingers or teeth 144 radially arrayed about the needle counter 116 and extending outwardly therefrom.

Figure 7:
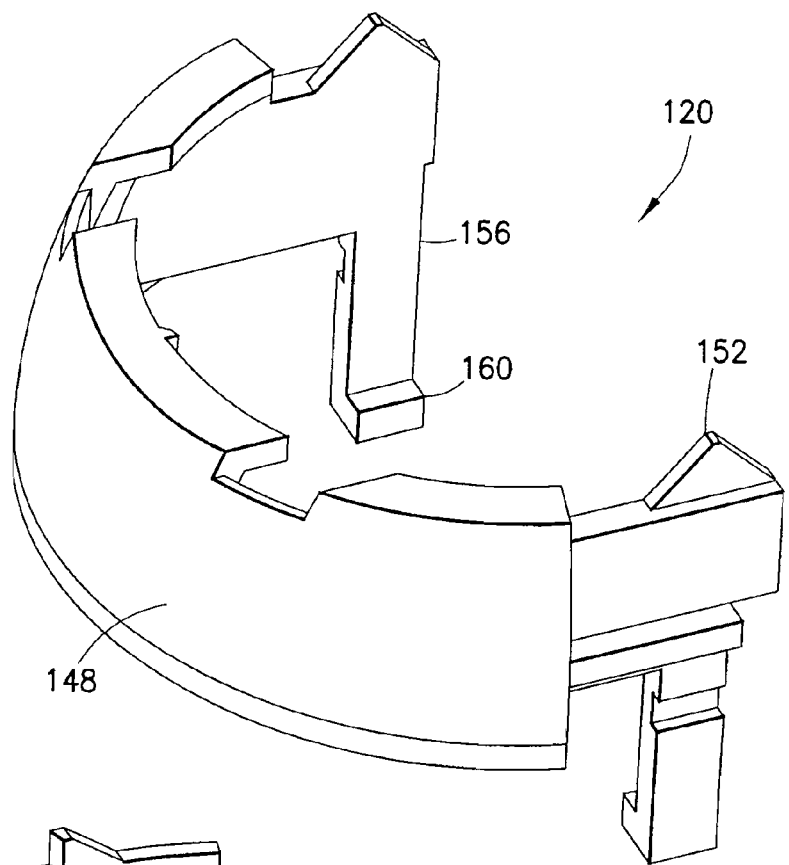
FIG. 7 is a perspective view of a user button of the needle changing device of FIG. 3.

FIG. 7 is a perspective view of the user button 120. As shown in FIG. 7, the user button 120 includes a user pressing portion 148 for interfacing with the user. The user button 120 also includes a tooth engaging portion 152 for engaging the teeth 144 to rotate the needle counter 116 when the user depresses the user button 120. As will described in greater detail below, the user button 120 further includes a cantilevered sliding member 156 with a foot 160 disposed at a distal end thereof.

Figure 8:
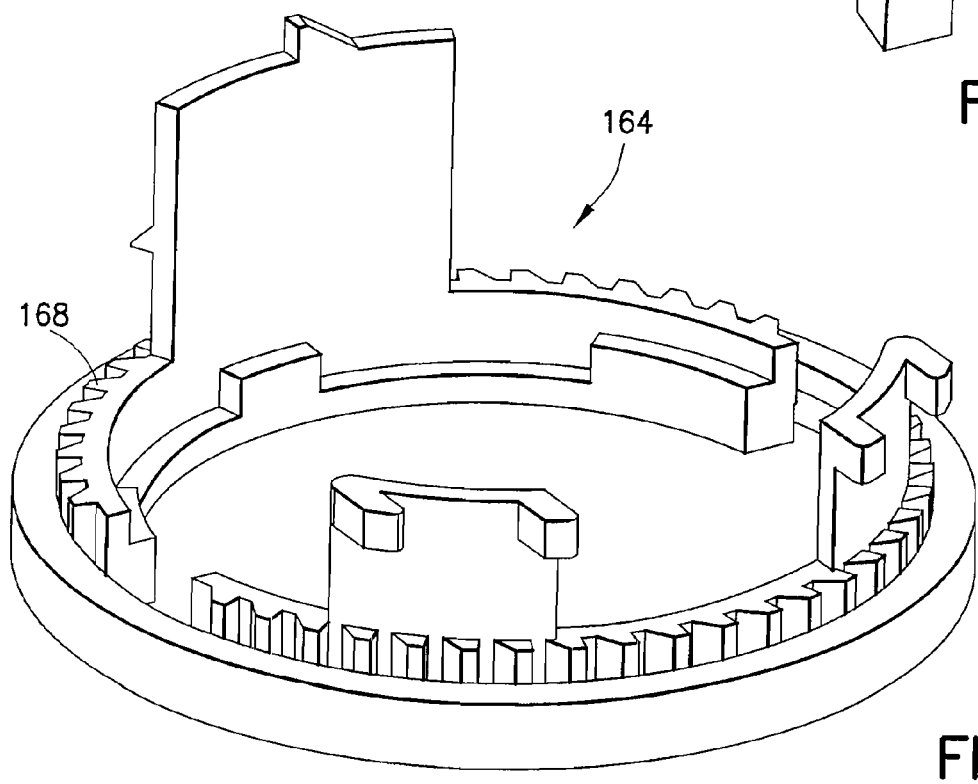
FIG. 8 is a perspective view of a ratchet top of the needle changing device of FIG. 3.

FIG. 8 is a perspective view of a ratchet top 164 of the changing device 100. The ratchet top 164 is disposed within the changing device 100 and includes a plurality of gear teeth 168 for selective engagement with the engagement arms 132 of the user dial 104. As the user rotates the user dial 104, the cantilevered engagement arms 132 disengage from gear teeth 168 and engage adjacent gear teeth 168. According to one embodiment, the gear teeth 168 and the engagement arms 132 are shaped so that the user dial 104 can only rotate in one direction.

Figure 9:
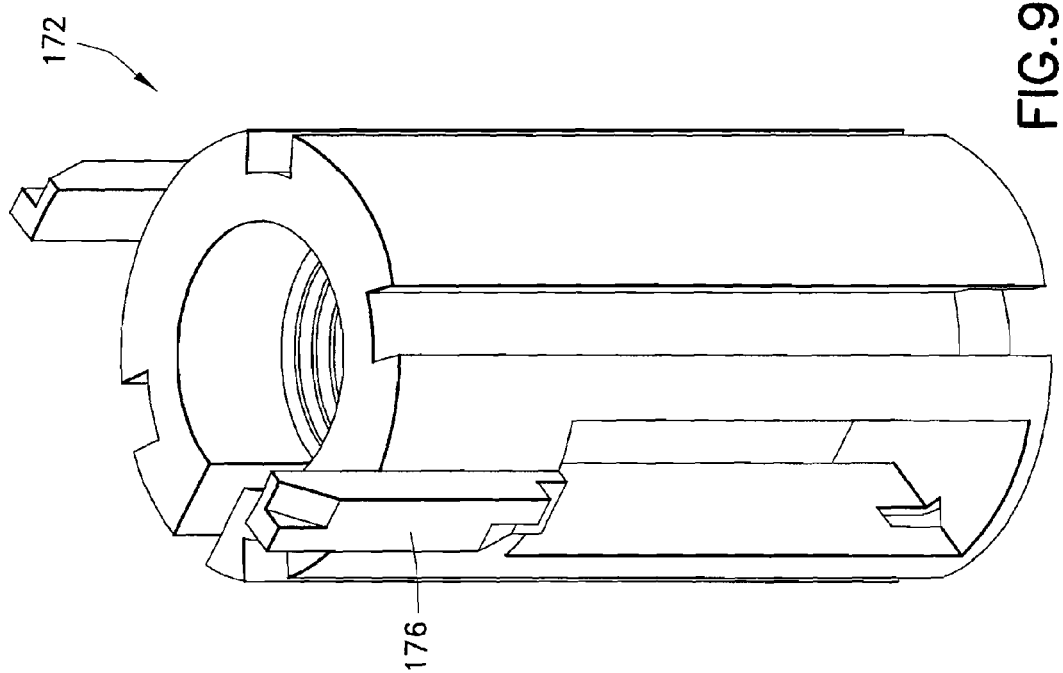
FIG. 9 is a perspective view of a fixed mount member of the needle changing device of FIG. 3.

FIG. 9 is a perspective view of a fixed mount member or fixed mount 172 of the changing device 100. As will be described in greater detail below, the fixed mount member 172 includes a sliding guide 176 for interaction with the sliding member 156 of the user button 120.

Figure 10:
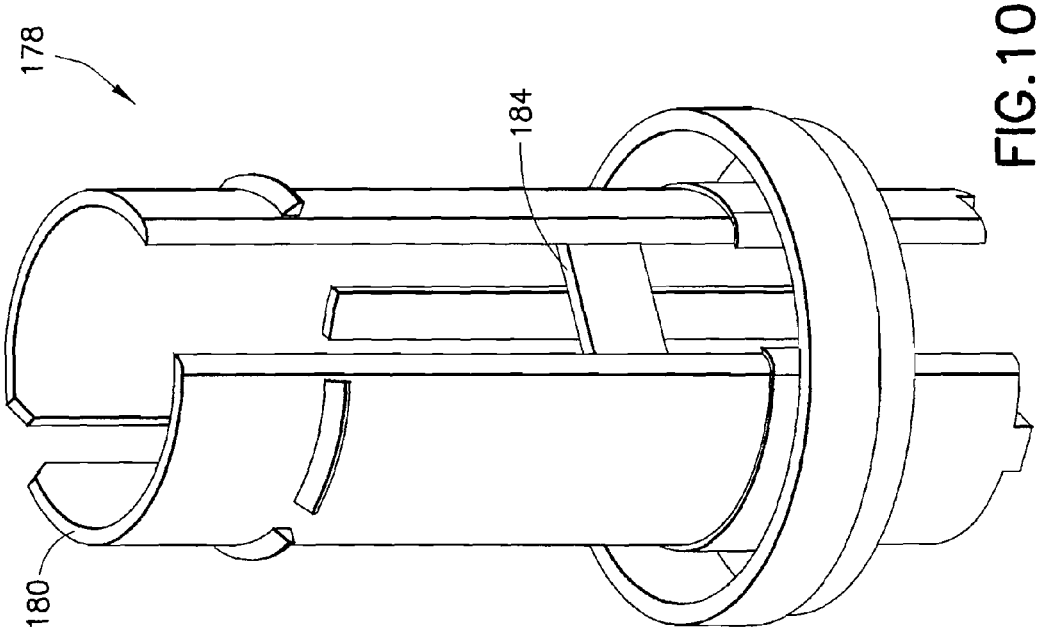
FIG. 10 is a perspective view of a maze member of the needle changing device of FIG. 3.
Figure 11:
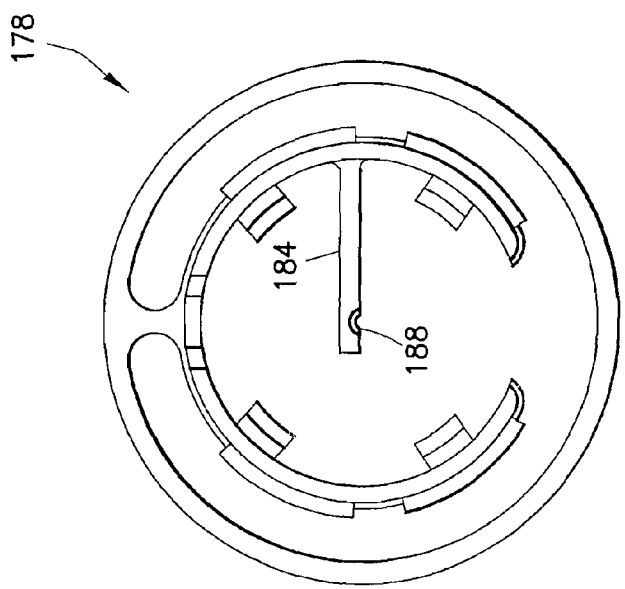
FIG. 11 is a perspective end view of a the maze member of FIG. 10.

FIG. 10 is a perspective view of a maze or maze member or guide member 178 and FIG. 11 is a perspective end view of the maze member 178. The maze member 178 includes guide walls 180 and a cantilevered needle snap arm 184. As shown in FIG. 11, the needle snap arm 184 includes a nesting portion 188. According to one embodiment the nesting portion 188 comprises a rounded axial groove.

Figure 12:
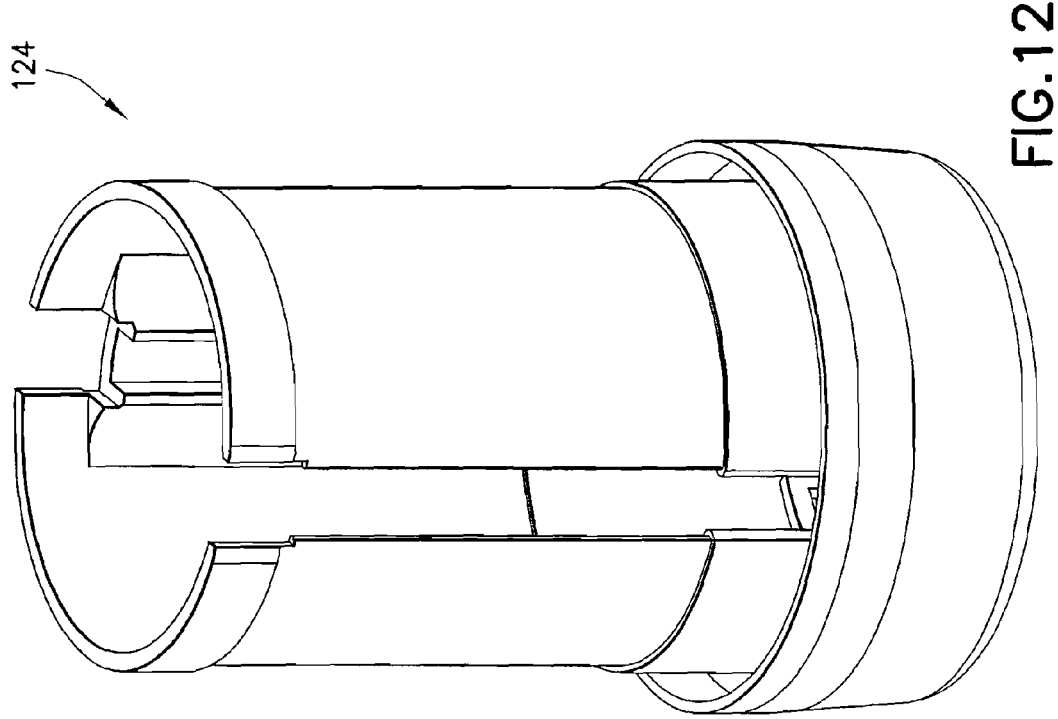
FIG. 12 is a perspective view of an inner track of the needle changing device of FIG. 3.

FIG. 12 is a perspective view of the inner track 124. When assembled, as will be described in greater detail below, the maze member 178 and the fixed mount 172 are disposed within the inner track 124.

FIG. 13 is a perspective view of a needle holder or band or band olier 192 of the changing device 100. As will be described in greater detail below, the needle holder 192 is a flexible band and has a plurality of upper and lower needle guides 196 and 198 for holding patient needles 200.

FIG. 14 is a perspective view of a patient needle or needle 200 of the changing device 100. As shown in FIG. 14, the needle 200 has a non-patient or septum end 204 for piercing the cartridge septum 16 of a pen injector, for example, pen injector 50. Although one of ordinary skill in the art will appreciate that other pen injectors may be used, for brevity, hereinafter, the pen injector 50 will be used as an exemplary pen injector. The needle 200 also has a patient end 208. The septum end 204 fluidly communicates with the patient end 208. As will be described in greater detail below, the needle 200 also includes hub 212 and a lifting hub 216.

FIG. 15 is a perspective view of a lock ring or needle donut 220 of the changing device 100. As shown in FIG. 15, the lock ring 220 has an axial hole therethrough to accommodate a needle 200.

FIG. 16 is a perspective view of a sterility barrier 224 of the changing device 100. According to one embodiment, as will be described in greater detail below, the sterility barrier 224 is disposed on the septum end 204 of the needle 200. According to another embodiment, the sterility barrier 224 is disposed on both the septum end 204 and the patient end 208 of the needle 200.

Figure 17:
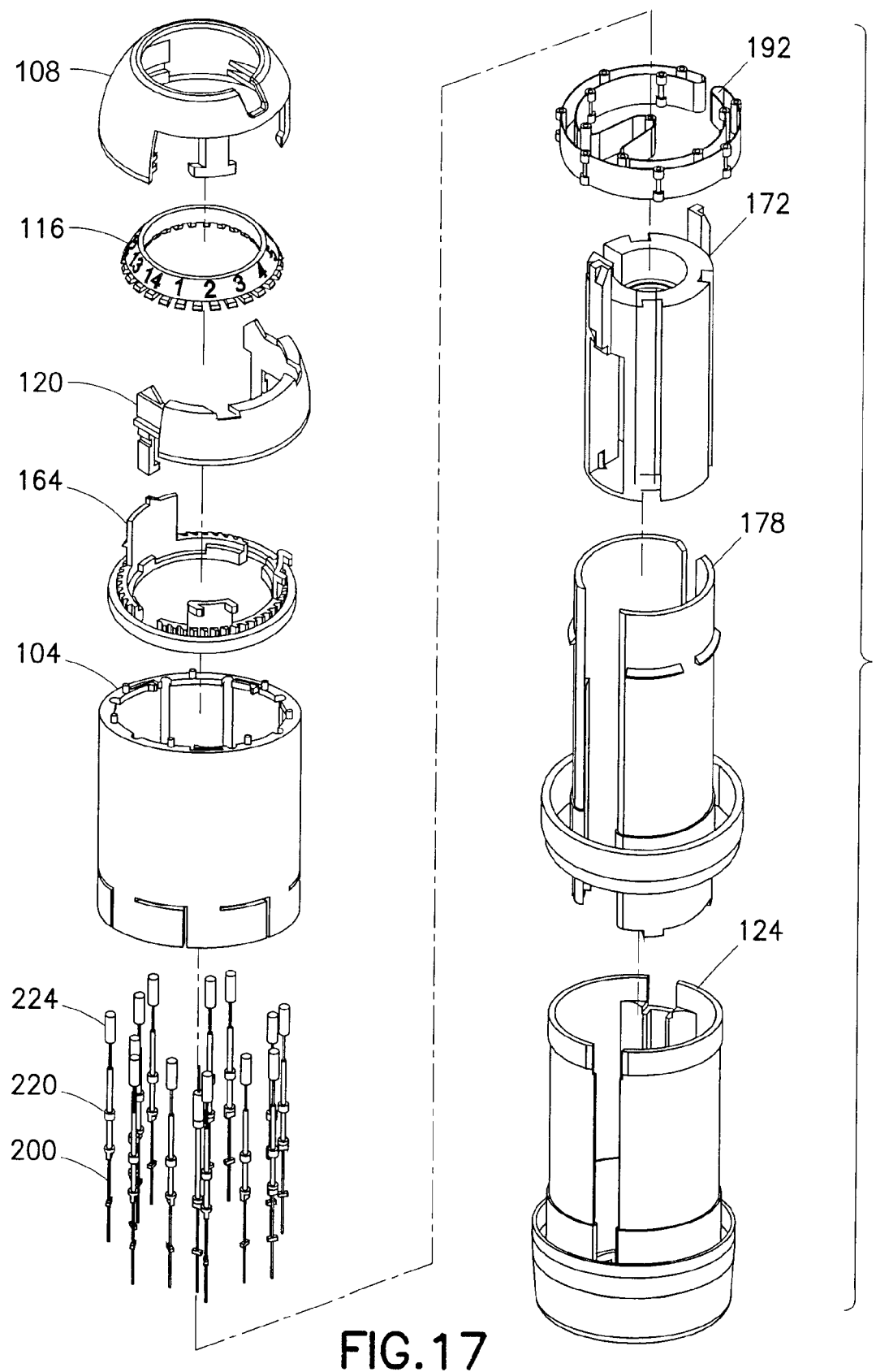
FIG. 17 is an exploded perspective view of the needle changing device of FIG. 3.
Figure 18:
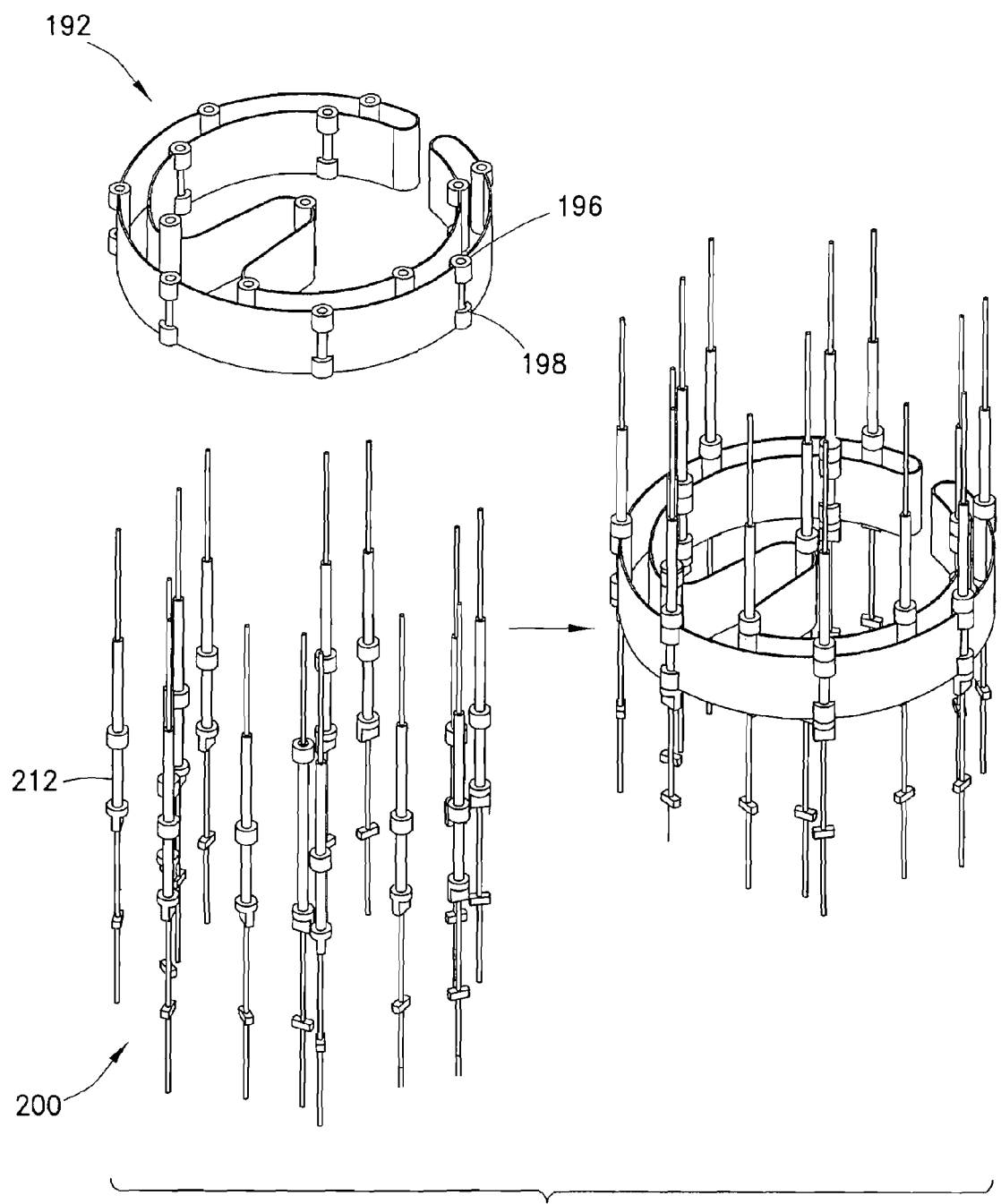
FIGS. 18-27 are perspective views of a method of assembling the needle changing device of FIG. 3.
Figure 19:
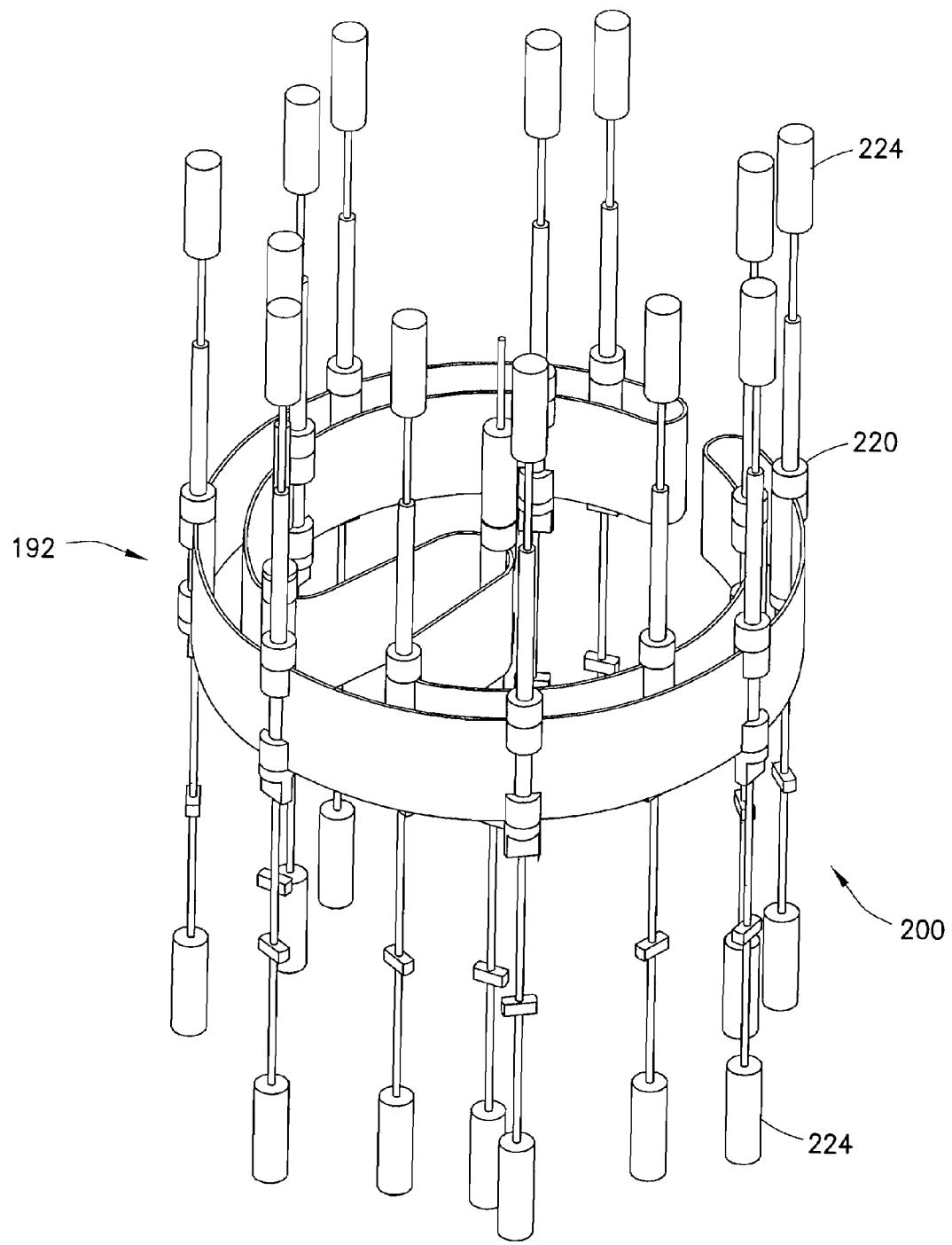

FIG. 17 is an exploded perspective view of the changing device 100. With reference to FIGS. 17-27, a method of assembly for the changing device 100 will now be described. Initially, needles 200 are inserted into needle guides 196 and 198 of the needle holder 192 until respective bases of the hubs 212 contact the respective lower needle guides 198 (FIG. 18). Subsequently, lock rings 220 are inserted over the septum ends 204 of the needles 200 to contact respective upper needle guides 196, and sterility barriers 224 are inserted on both the septum ends 204 and the patient ends 208 of the needles 200 (FIG. 19).

Figure 20:
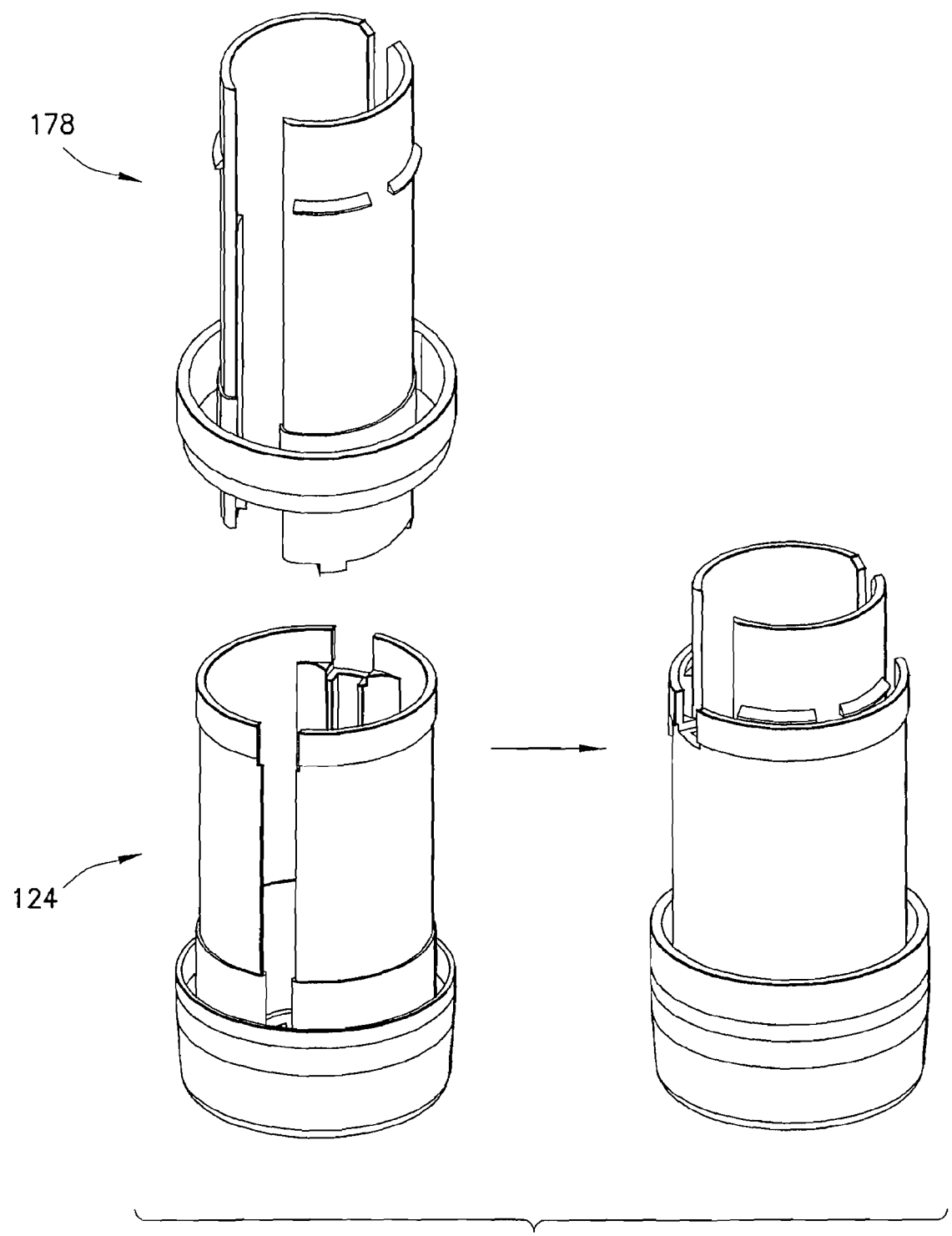
Figure 21:
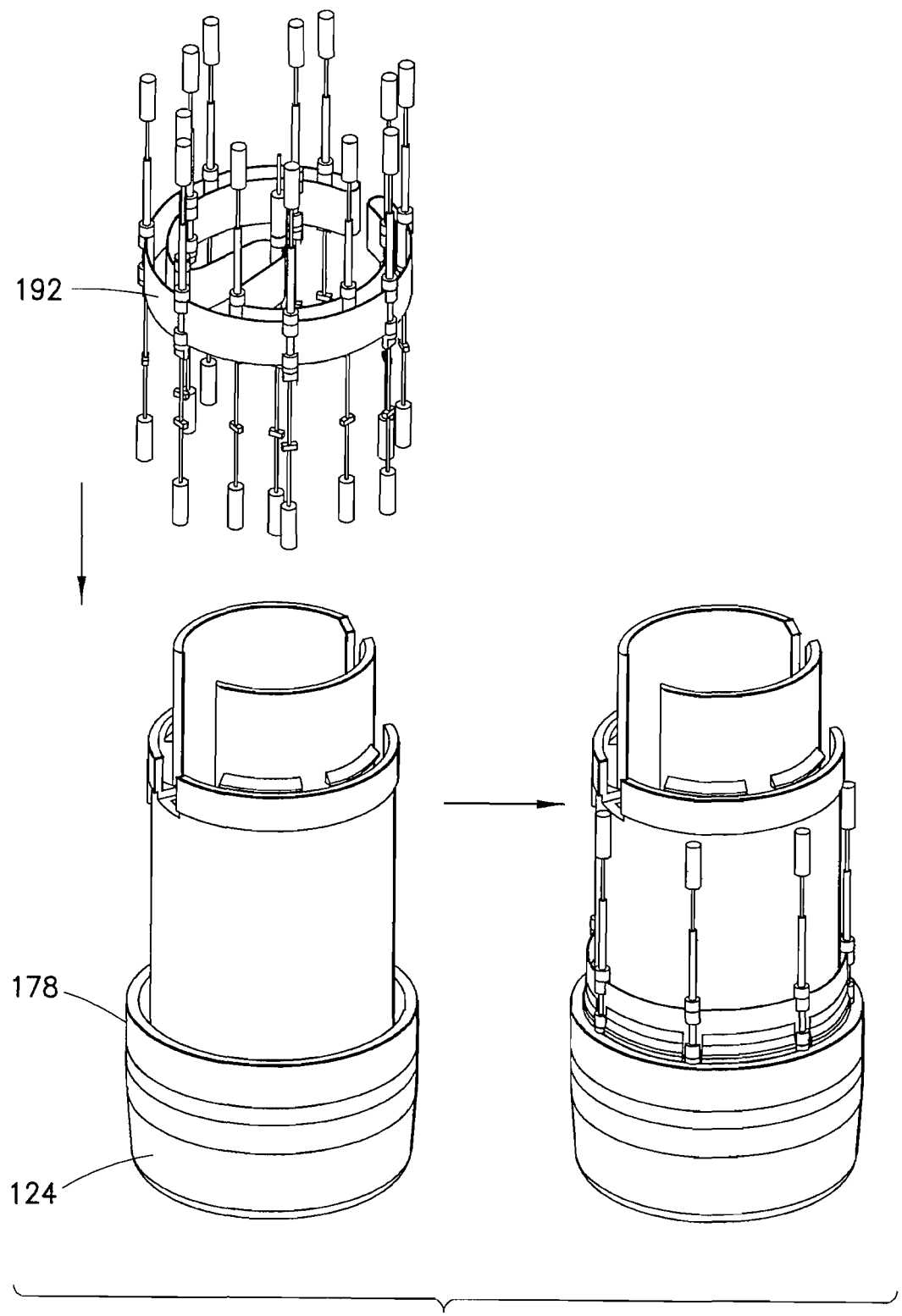
Figure 22:
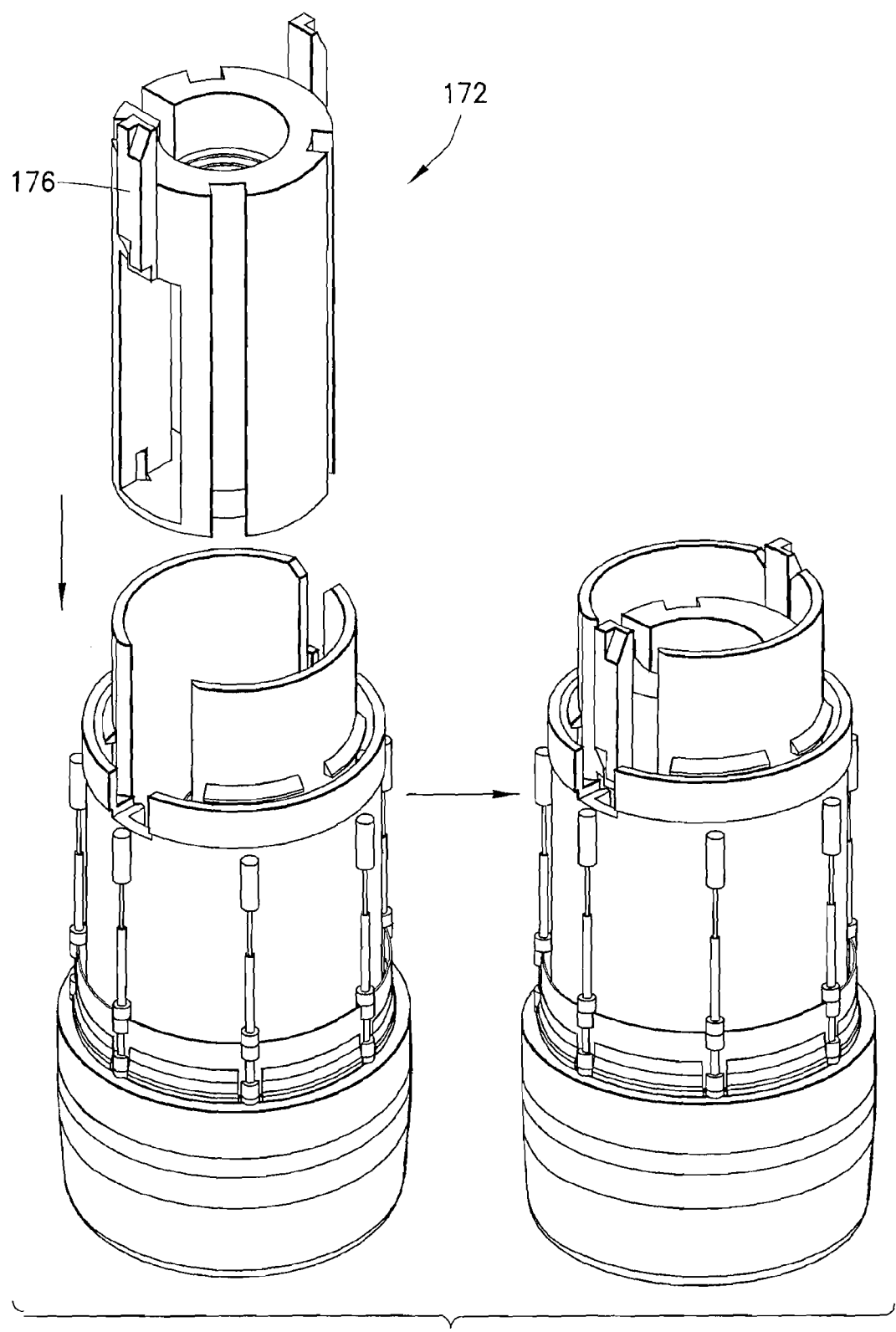

Next, an assembler combines the inner track 124 and the maze member 178, for example, by snapping them together (FIG. 20). Then, the assembler slides the needle holder 192 (formed into a non-circular, circuitous loop) onto the inner track 124 and maze member 178 assembly (FIG. 21).

Figure 23:
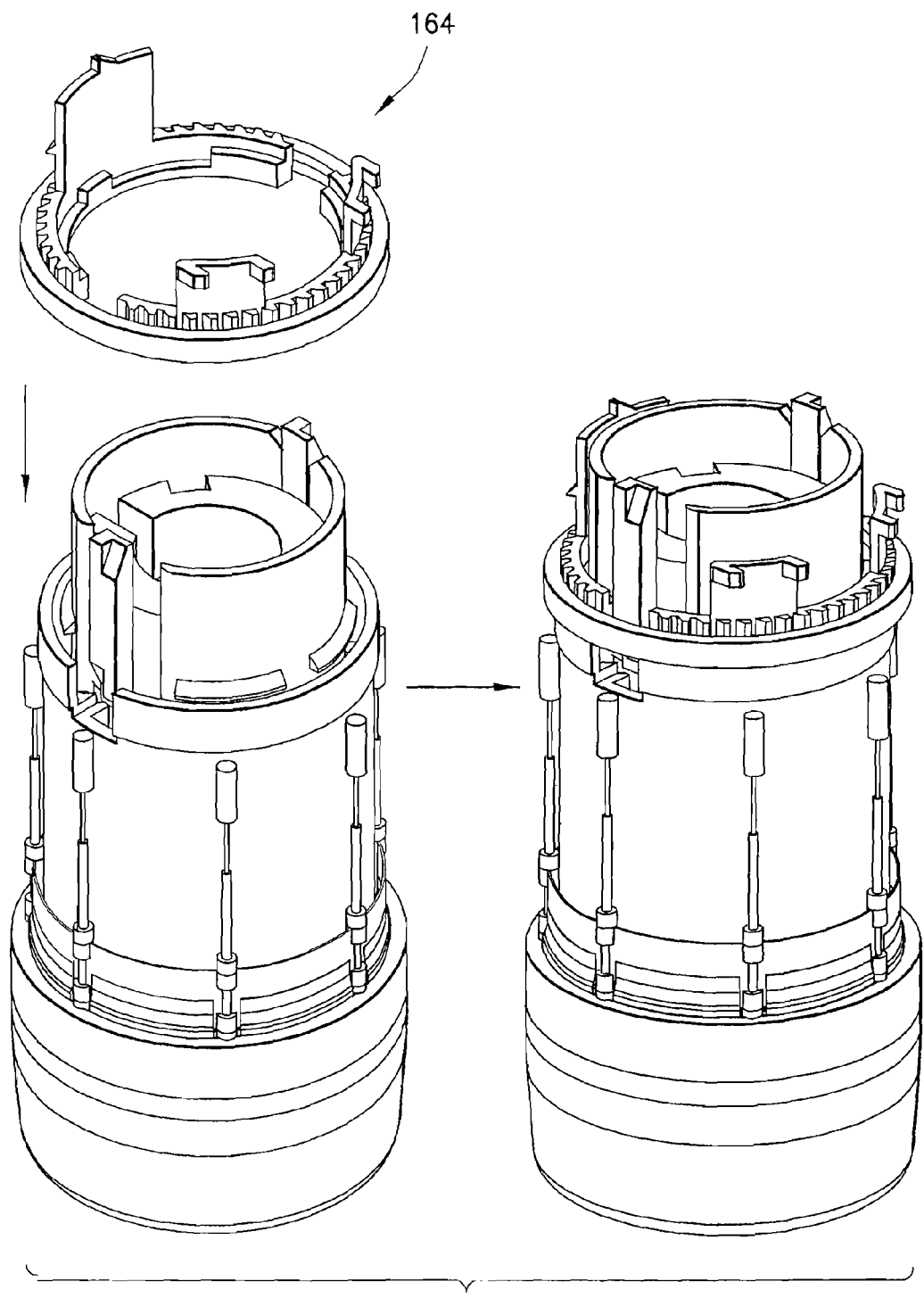
Figure 24:
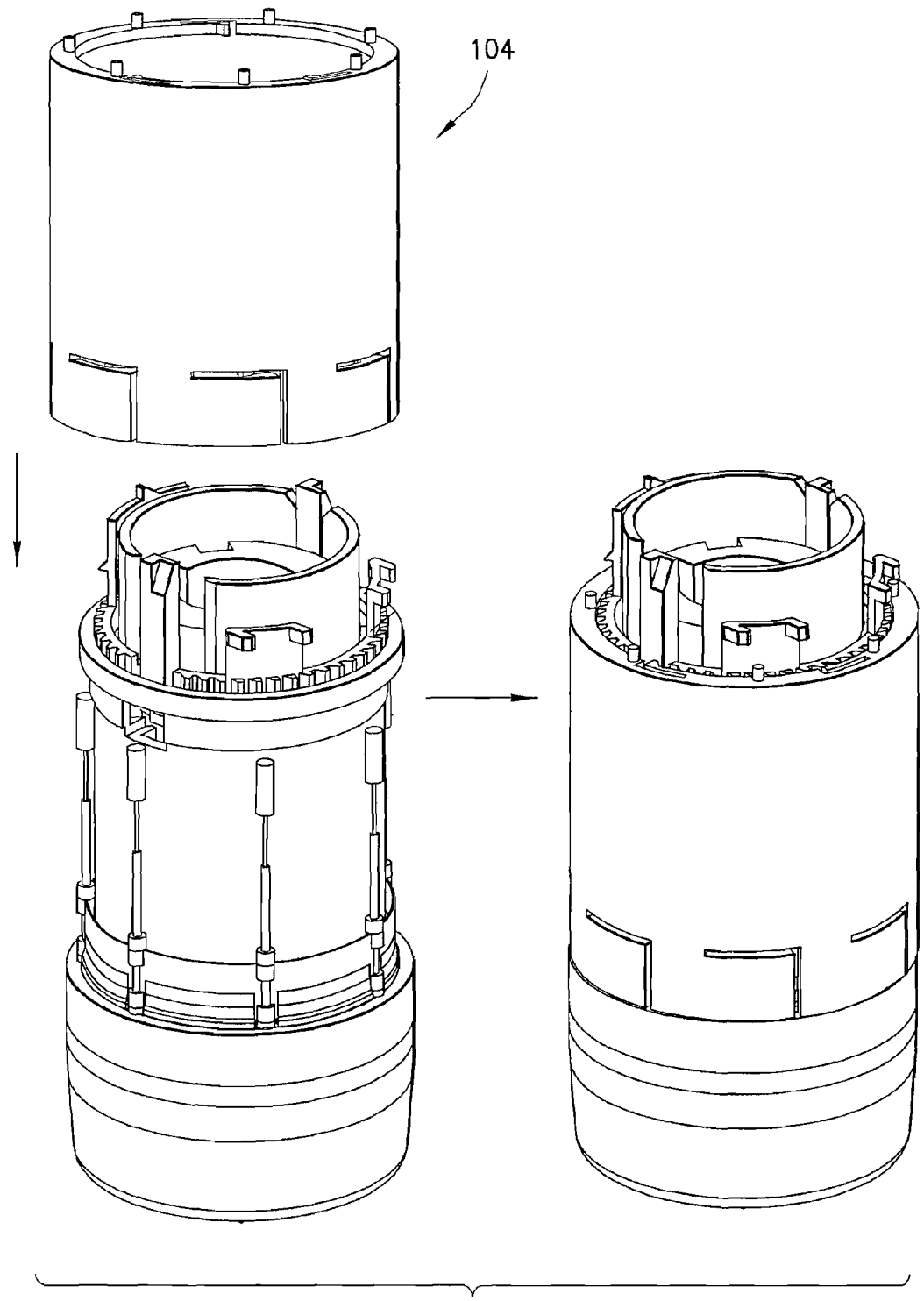
Figure 25:
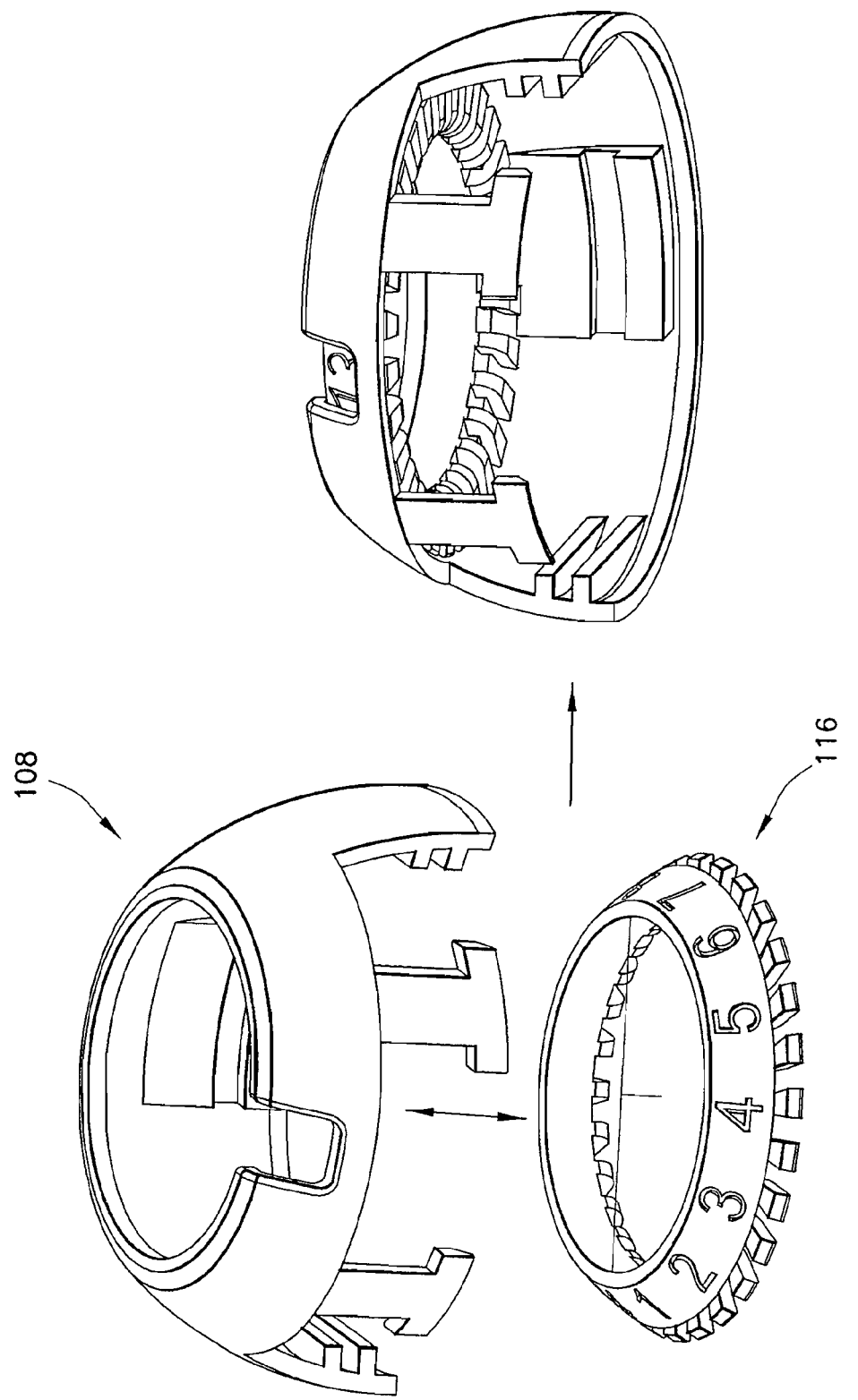
Figure 26:
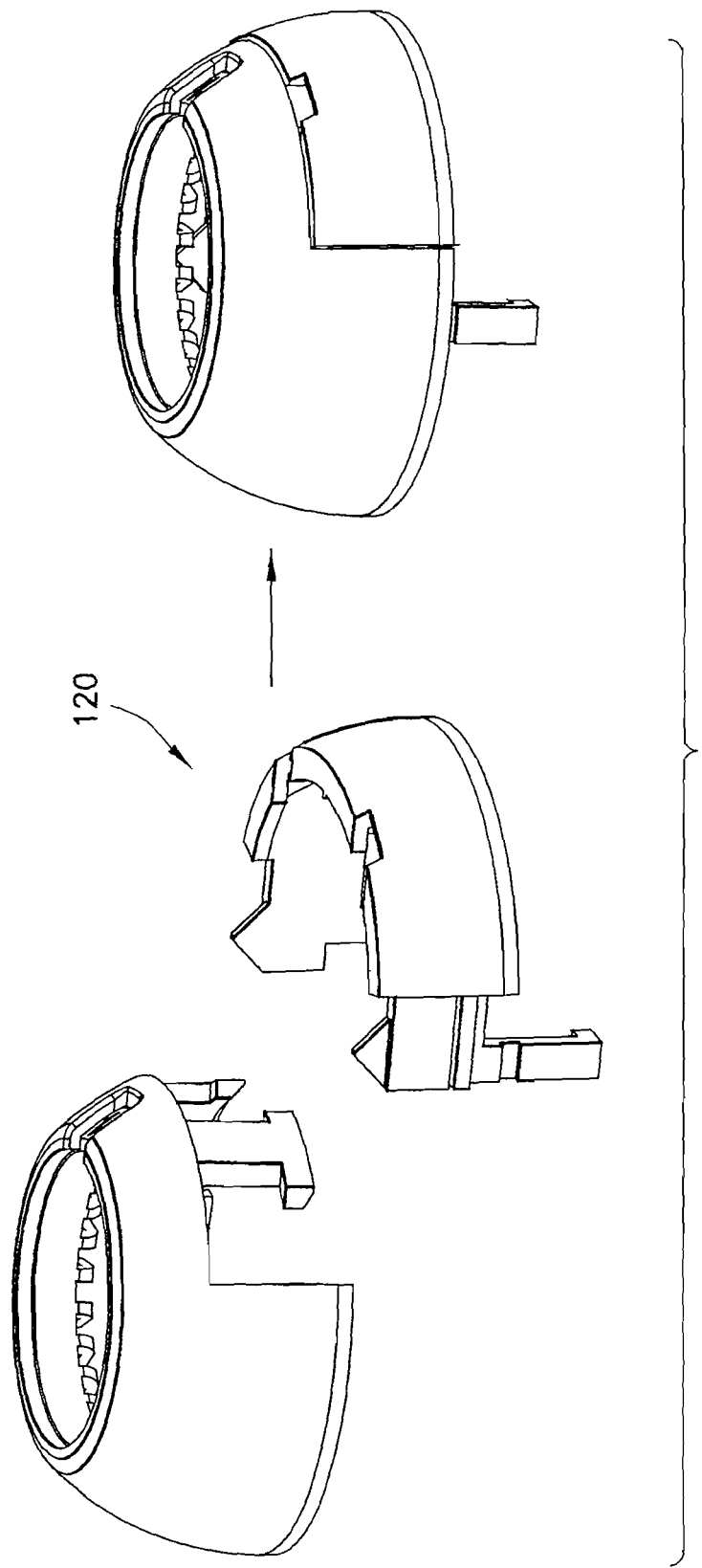
Figure 27:
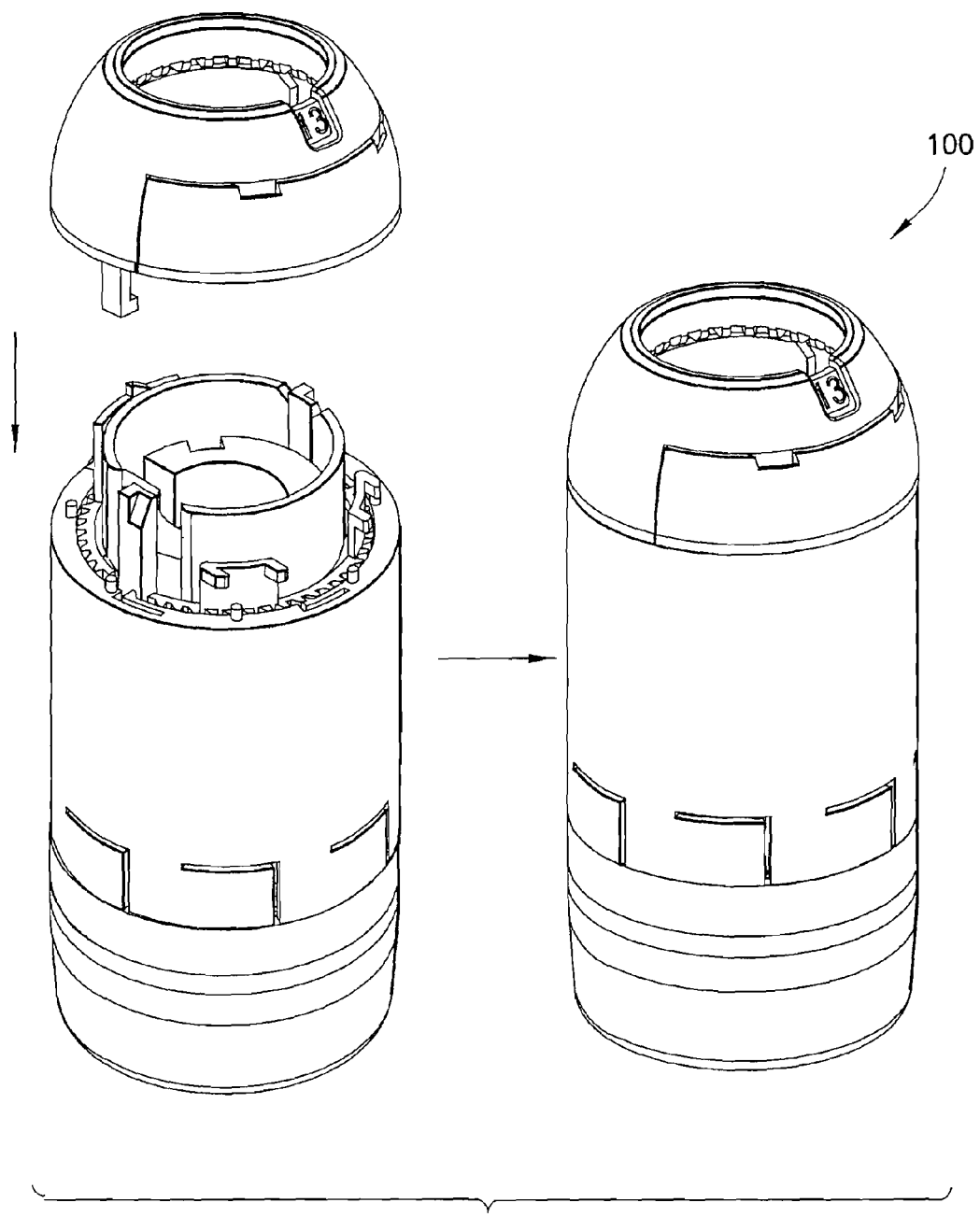

Thereafter, the assembler inserts the fixed mount 172 into the maze member 178 (FIG. 22) and attaches the ratchet top 164 onto the assembly, for example, by snapping (FIG. 23). The assembler then places the user dial 104 over the assembly (FIG. 24). Next, the assembler places the needle counter 116 in the cap 108 (FIG. 25), and slides the user button 120 into the cap assembly (FIG. 26). Finally, the assembler attaches the cap assembly, completing the changing device 100 (FIG. 27).

An overview of the operation of the changing device 100 will now be described with reference to FIGS. 28-34. As shown in FIG. 28, the user combines the pen injector 50 and the changing device 100, for example, by screwing the pen injector 50 into the changing device 100. Next the user rotates the user dial 104 (FIG. 29) to select the next unused needle

Figure 30:
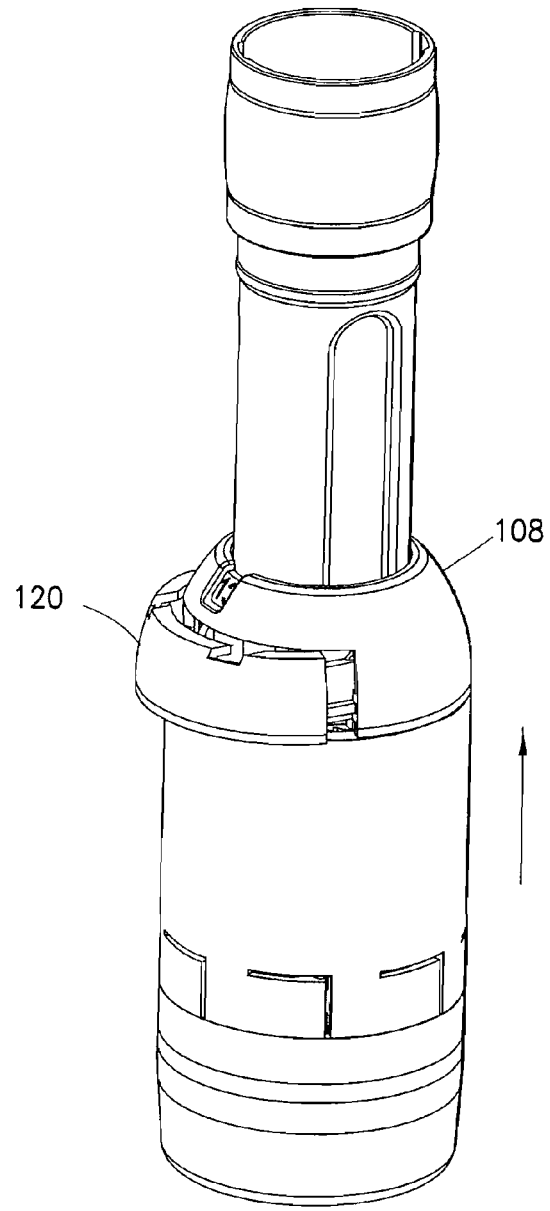
Figure 31:
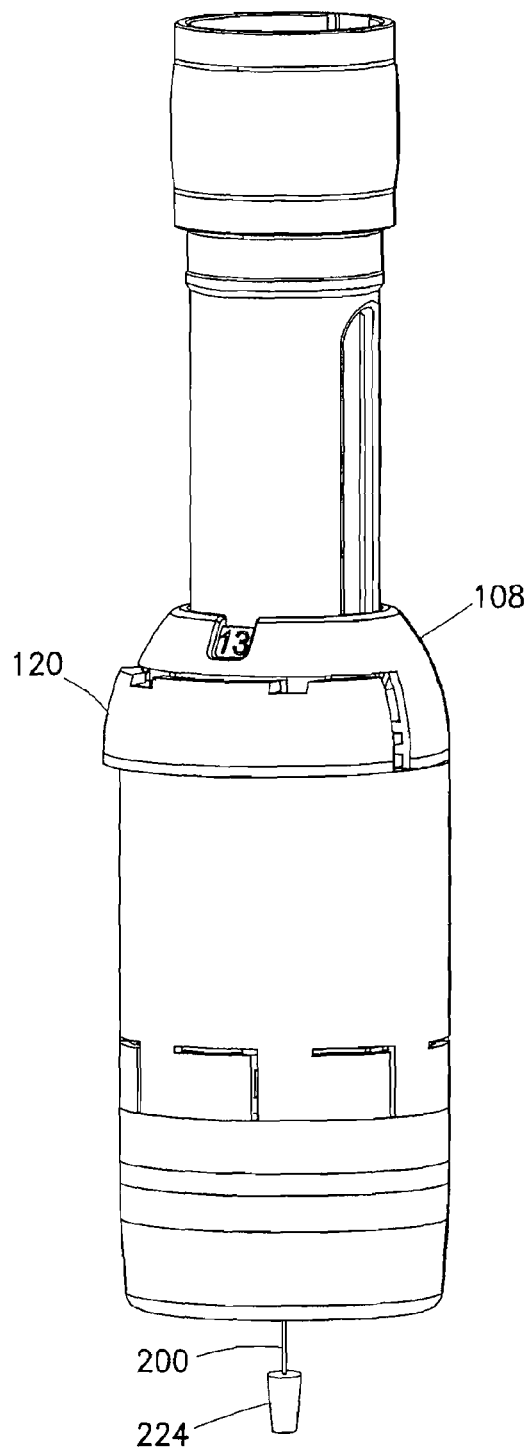

200. The rotation of the user dial 104 causes the user button 120 to extend radially from the changing device 100 (FIG. 30). The user then slides the user dial 104 axially toward the pen injector 50, causing the septum end 204 of the patient needle 200 to pierce the cartridge septum 16 of the pen injector 50 and exposing the patient end 208 of the patient needle 200 and the sterility barrier 224 disposed thereon (FIG. 31).

Figure 32:
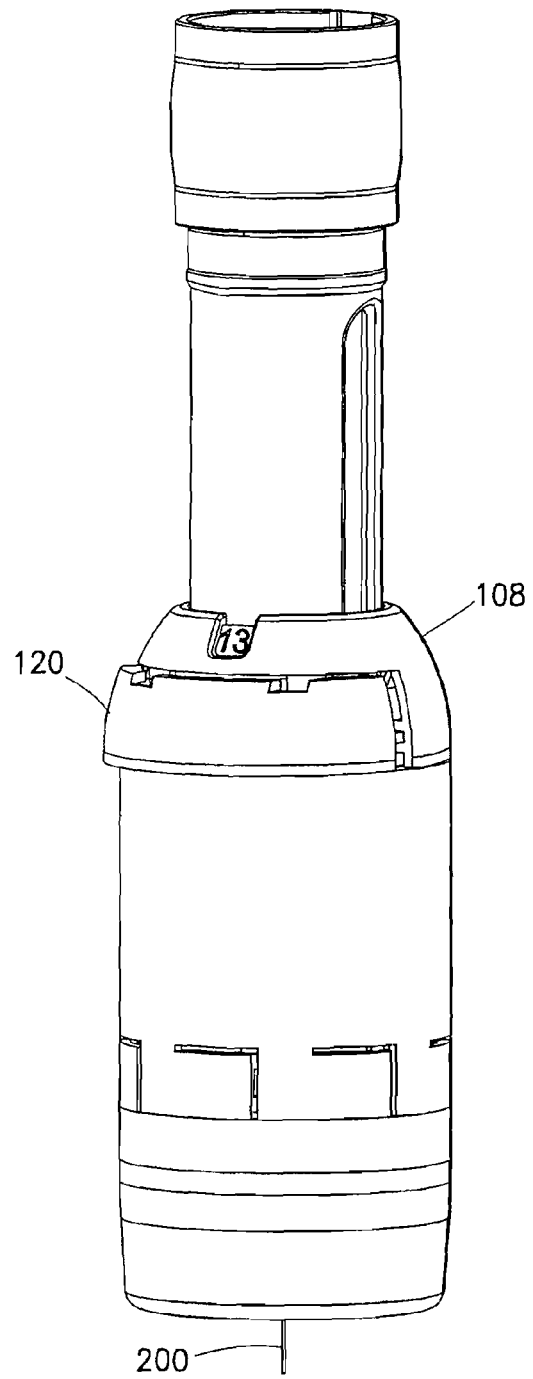
Figure 33:
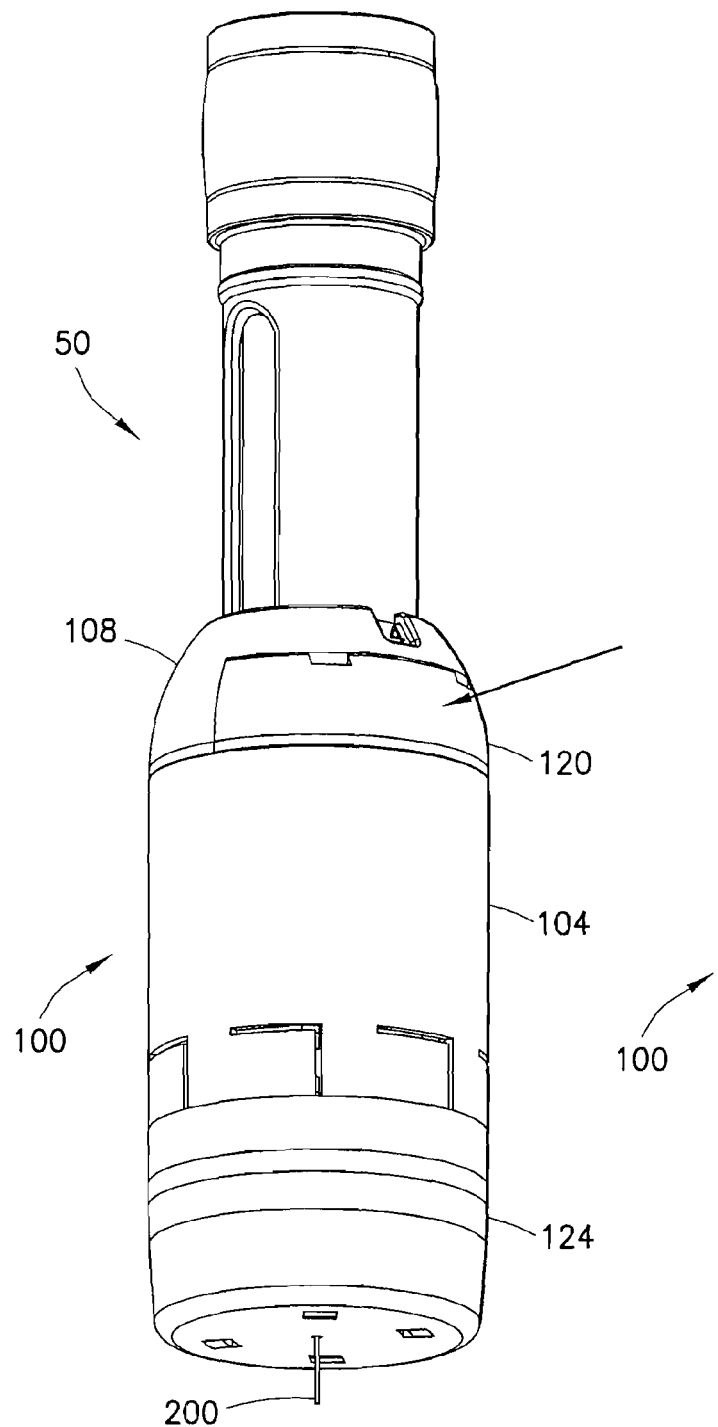
Figure 34:
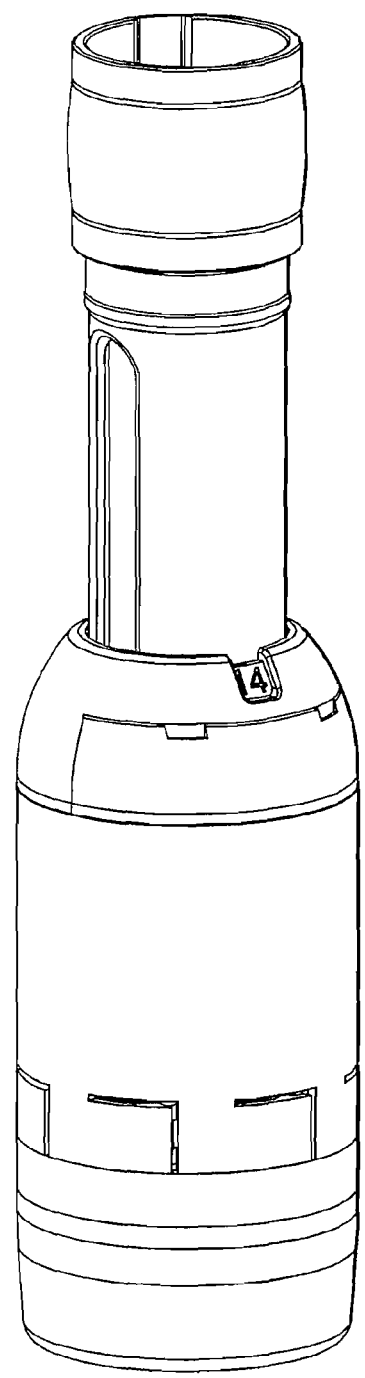

Subsequently, according to an exemplary embodiment, the user removes the sterility barrier 224 from the patient needle 200 for example, by sliding the sterility barrier 224 off of the patient needles 200 (FIG. 32). The device is now ready for the user to inject the medicament. Subsequent to the injection, as will be described in greater detail below, the user depresses the user button 120 (FIG. 33), thereby advancing the needle counter 116. According to one embodiment, the user then slides the user dial 104 axially away from the pen injector to re-sheath the needle 200. According to another exemplary embodiment (not shown), depressing the user button 120 activates a spring-loaded return mechanism that moves the user dial 104 axially away from the pen injector 50 and re-sheathes the needle 200. Once the user dial 104 has completed its down-stroke, moving axially away from the pen injector 50, the changing device 100 is ready for the user to again rotate the user dial 104 and select the next unused needle 200 (FIG. 34).

Figure 35:
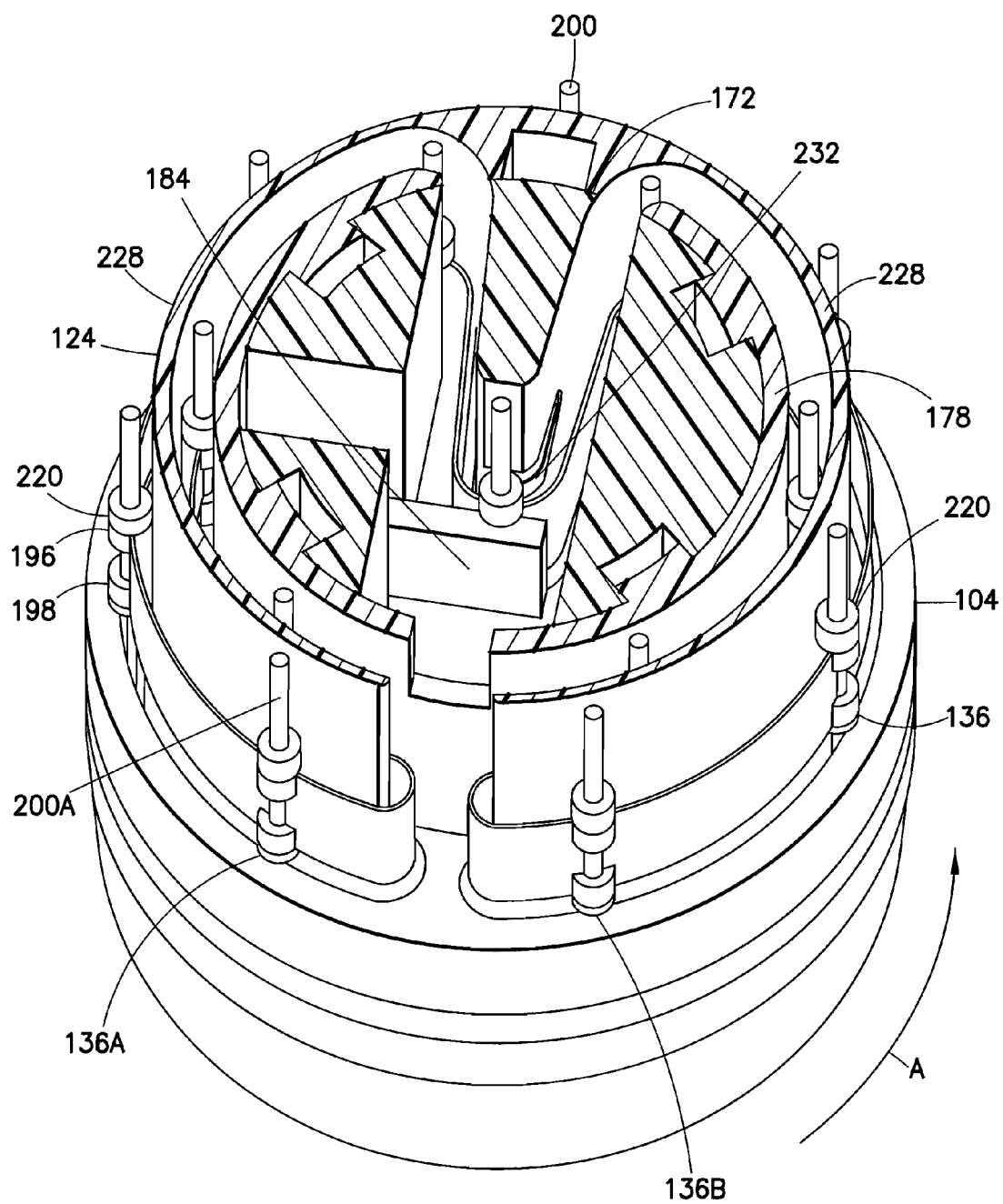
FIG. 35 is a partial perspective view in cross-section of the needle changing device of FIG. 3.

In greater detail, as shown in FIG. 35, the integral engaging structures or axial grooves 136 of the user dial 104 engage radially outermost surfaces of the upper needle guides 196, lower needle guides 198, and lock rings 220 that correspond to the needles 200 in the needle holder 192 that are disposed on the radially outermost portions of wall 228 of the inner track 124. As the user rotates the user dial 104 (FIG. 29), because the upper needle guides 196, lower needle guides 198, and lock rings 220 are engaged with the axial grooves 136, the needle holder 192 is advanced along its non-circular, circuitous path among the inner track 124, the maze 178, and the fixed mount 172. In this illustrated embodiment, the user rotates the user dial 104, and thus the outermost portion of the needle holder 192, in a direction shown by arrow A. One skilled in the art will understand, however, that the user could rotate the user dial 104 in the opposite direction without departing from the scope of the present invention. The user button 120 in combination with a ratchet-interface to the ratchet top 164 prevent the user from re-using a used needle.

With respect to the state depicted in FIG. 35, upon the next rotation of the user dial 104, the needle 200A will pass through the opening in the wall 228 to move in between the wall 228 of the inner track 124 and the maze 178. Similarly, the needle 200B, disposed between the maze 178 and the wall 228 in FIG. 35 will pass through the opening in the wall 228 to a position radially outside of the wall 228. Additionally, during the next rotation of the user dial 104, the axial groove 136A will disengage from the needle 200A as the needle 208 passes through the opening in the wall 228, and will engage needle 200B as it passes through the opening in the wall 228 and come to rest in the position illustrated as 136B in FIG. 35.

Rotation of the user dial 104 (and the corresponding advancement of the needle holder 192 along its circuitous path) moves a next unused needle 200 into a "selected" position substantially in the middle of the changing device 100. As shown in FIG. 35, when a needle 200 moves into the selected position, the upper and lower needle guides 196 and 198 engage the needle snap arm 184. More specifically the upper and lower needle guides 196 and 198 engage the nesting portion 188 of the needle snap arm 184. Additionally, when the needle 220 moves into the selected or activated position, the lock ring 220 engages a lock feature 232 of the fixed mount 172. According to one embodiment, the lock feature 232 is integrally formed as a single unit with the fixed mount 172. According to another embodiment, the lock feature 232 is part of an element that is inserted into the fixed mount 172. The engagement of the upper and lower needle guides 196 and 198 with the nesting portion 188 and the engagement of the lock ring 220 with the lock feature 232 axially aligns the "selected" needle 200 with an opening (described in greater detail below) in the inner track 124 and with the cartridge septum 16.

Figure 36:
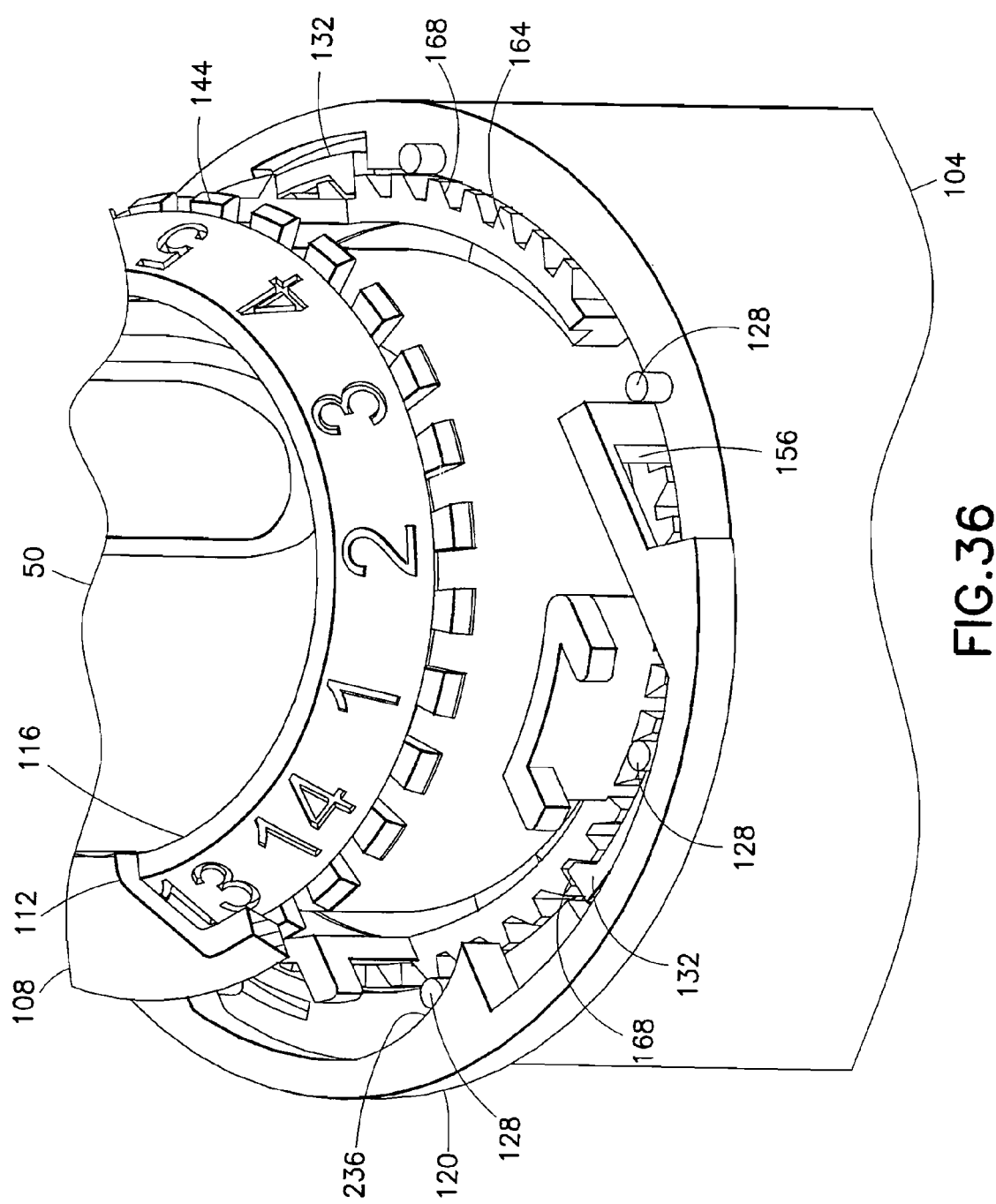
FIG. 36 is a perspective cutaway view of the needle changing device of FIG. 3.

In addition to selecting the next unused needle 200, as noted previously, rotation of the user dial 104 also causes the user button 120 to extend radially from the changing device 100. FIG. 36 is a perspective view of the changing device 100 with several elements cut away for illustrative purposes. For example, only a bottom portion of the user button 120 is shown in FIG. 36. As shown, the bottom portion of the user button 120 includes a ramp portion 236. When the user rotates the user dial 104, one of the bosses 128 on a top thereof engages the ramp portion 236 and the forces the user button 128 radially outward, as shown in FIG. 36. FIG. 36 additionally illustrates how the engagement arms 132 of the user dial 104 serially engage the gear teeth 168 of the ratchet top 164 and prevent backward rotation of the user dial 104.

Figure 38:
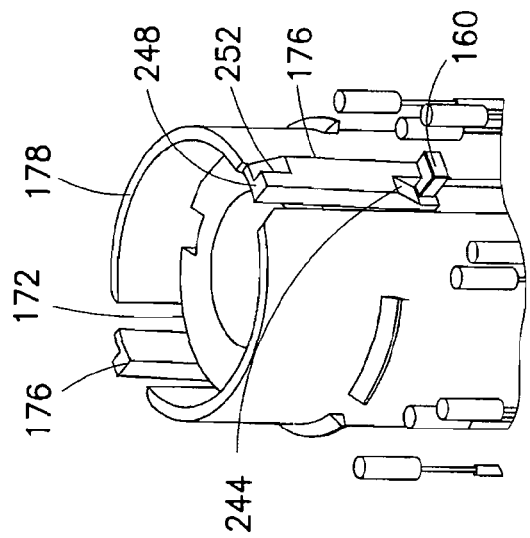
FIGS. 38-41 are partial perspective views of the needle changing device of FIG. 3 illustrating interaction of a user button and a sliding guide.
Figure 37:
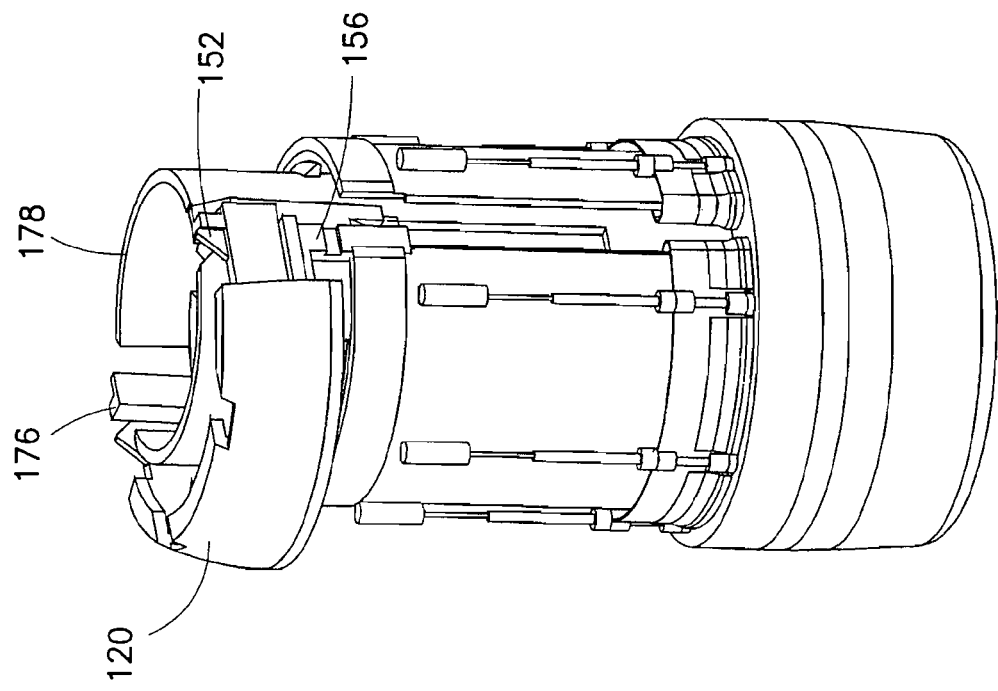
FIG. 37 is a partial perspective view of the needle changing device of FIG. 3.
Figure 39:
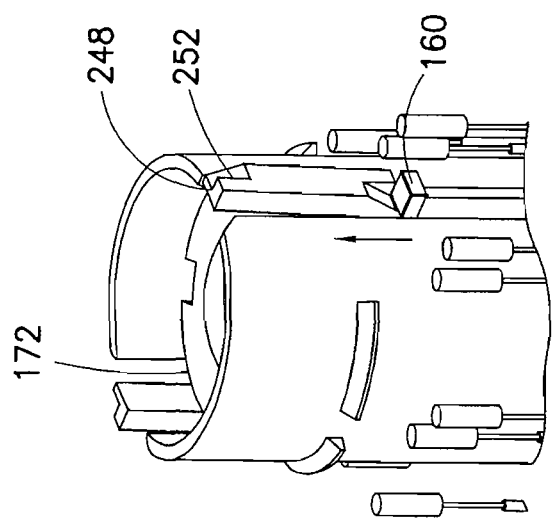

FIG. 37 is a partial perspective view of the changing device 100 and FIGS. 38-41 are partial perspective views illustrating interaction of the user button 120 and the sliding guide 176 during operation of the changing device 100. FIG. 38 illustrates the changing device 100 in a "transport" or "expended" state. In FIGS. 38-41, the majority of the user button 120 is cut away; only the foot 160 of the sliding member 156 is shown. In the transport state, the foot 160 is disposed beneath a lower stop portion 240 (best shown in FIG. 41) of the sliding guide 176. As the user rotates the user dial 104 and the user button 120 moves radially outward, as shown in FIG. 39, the foot 160 moves from beneath the lower stop portion 240 to a position at adjacent a lower ramp portion 244 (best shown in FIGS. 40 and 41).

Figure 41:
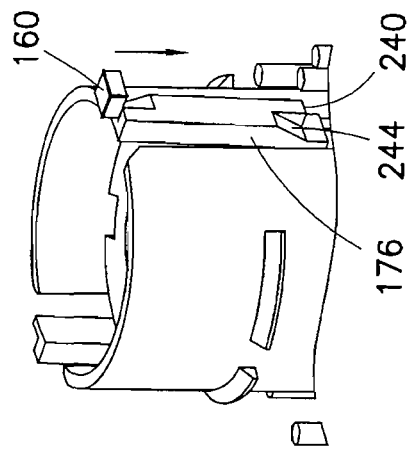
Figure 40:
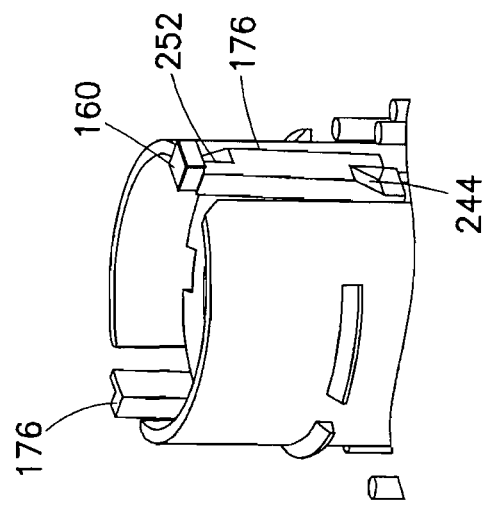

As the user slides the user dial 104 proximally, or axially toward the pen injector 50, the foot 160 travels up the lower ramp portion 244 and across the sliding guide 176 to a position above an upper stop portion 248, as shown in FIG. 40. Then, as the user depresses the user button 120, the foot 160 moves from above the upper stop portion 248 to a position adjacent an upper ramp portion 252, as shown in FIG. 41. Subsequently, as the user (and/or a spring) slides the user dial 104 axially away from the pen injector 50 to complete the stroke, the foot 160 slides up the upper ramp portion 252 and across the sliding guide 176, back to the transport position shown in FIG. 38, beneath the lower stop portion 240.

FIGS. 42-44 are perspective cutaway views of the changing device 100 illustrating the interaction of the needle snap arm 184, the needle 200, and the cartridge septum 16 during the axial movement of the user dial 104 toward the pen injector 50. As shown in FIG. 42, as the user axially moves the user dial 104 toward the pen injector 50, the needle 200 remains substantially stationary as the patient end 208 is exposed through an opening 256 in the inner track 124 by the movement of the inner track 124. Additionally, the needle snap arm 184 lifts the needle holder 192 and the lock ring 220 axially toward the pen injector 50 and slides the needle holder 192 and the lock ring 220 upward with respect to the hub 212.

Subsequently, as shown in FIG. 43, a slanted portion of the openings 256 contacts the lifting hub 216 and begins to lift the needle 200 axially toward the pen injector 50, so that the sterility barrier 224 on the septum end 204 of the needle 200 contacts the septum cartridge 16. Then, as shown in FIG. 44, the slanted portion of the opening 256 continues to lift the needle 200 via the lifting hub 216 until the user dial 104 reaches the top most point of its stroke, at which time the septum end 204 of the selected needle 200 pierces the top of the sterility barrier 224 and the cartridge septum 16 to communicate with the medicament in cartridge 12. At this point, as described previously, the user removes the sterility barrier on the patient end 208 of the needle 200 and injects the medicament using the pen injector 50, through the selected needle 200.

Figure 45:
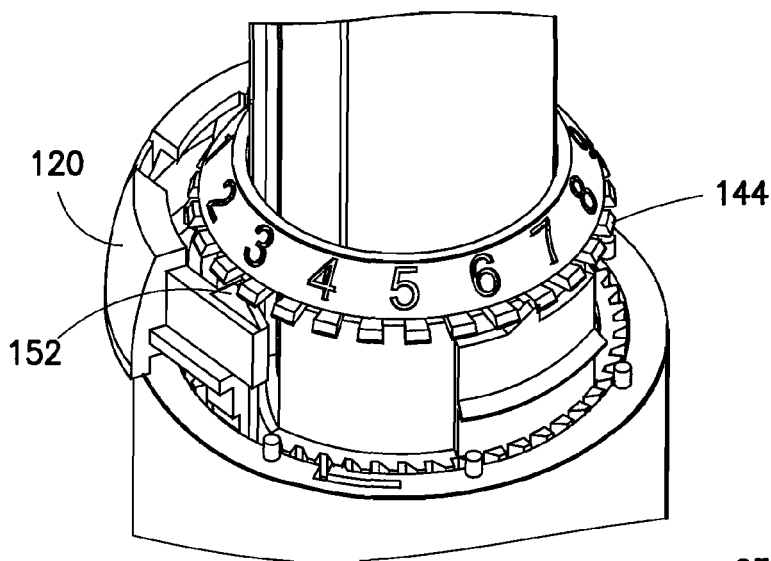
FIG. 45 is a partial perspective view of the needle changing device of FIG. 3 illustrating depression of the user button.

Subsequently, as shown in FIG. 45, when the user depresses the user button 120, a tooth engaging portion 152 of the user button 120 engages one of the plurality of teeth 144 of the needle counter 116 and advances the needle counter 116 so that the next identification number is visible through the window 112 of the cap 108. Additionally, as noted previously, when the user depresses the user button 120, the foot 160 moves from above the upper stop portion 248 to the position adjacent the upper ramp portion 252, thereby allowing the user to then slide the user dial 104 distally, or axially away from the pen injector 50.

Figure 46:
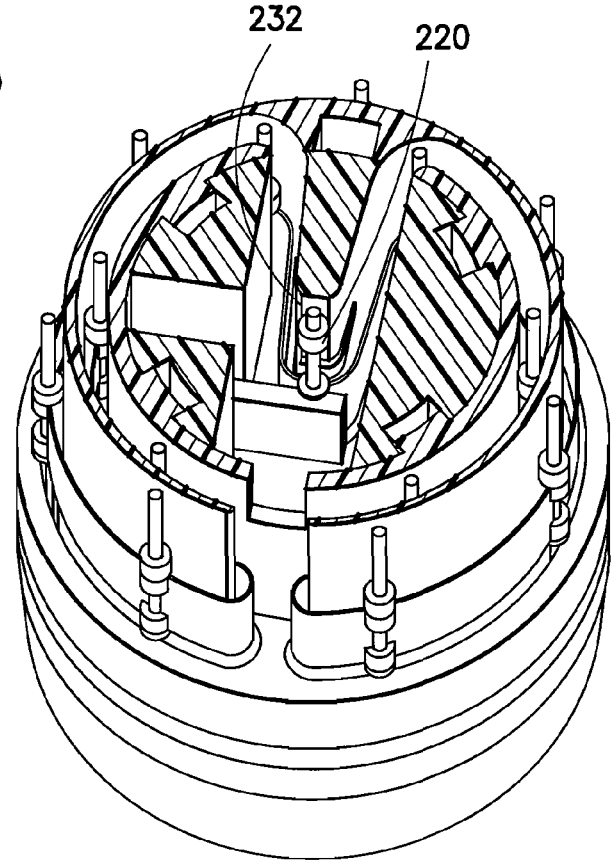
FIG. 46 is a partial perspective view of the needle changing device of FIG. 3.

As shown in FIG. 46, after the user (and/or a spring) moves the user dial 104 fully away from the pen injector 50, the lock ring 220 no longer engages the lock feature 232, thus enabling the user to rotate the user dial 104 and select the next unused needle 200.

FIG. 47 is a perspective view of a changing device 280 in accordance with another embodiment of the present invention. In the changing device 100, the needles 200 remain substantially parallel to a primary longitudinal axis of the changing device 100 throughout their circuitous path. In contrast, however, the bottom of the changing device 280 angles inwardly. Thus, rather than the remaining substantially parallel to a primary longitudinal axis of the changing device 280 during the entire circuitous path of the needle holder 192, when the needles 200 are passing radially outwardly of the walls 228, the needles 200 are substantially parallel to the inwardly tapering exterior surface of the changing device 280. But once the needles 200 are inside the walls 228, then, like the changing device 100, the needles are substantially parallel to the primary longitudinal axis of the changing device 280.

FIG. 48 is a perspective view of a changing device 284 in accordance with another embodiment of the present invention. As shown in FIG. 48, the changing device 284 includes a spring-loaded needle shield 288. The needle shield 288 deploys when the user moves the user dial 104 axially toward the pen injector 50, protects the patient from needle exposure, and prevents medicament flow from the needle 200 until the needle shield 288 is depressed back within the changing device 284. By depressing the needle shield 288 back into the device, the changing device 284 is reset automatically to its starting state. This exemplary embodiment reduces the number of user steps, providing a favorable patient experience.

Figure 49:
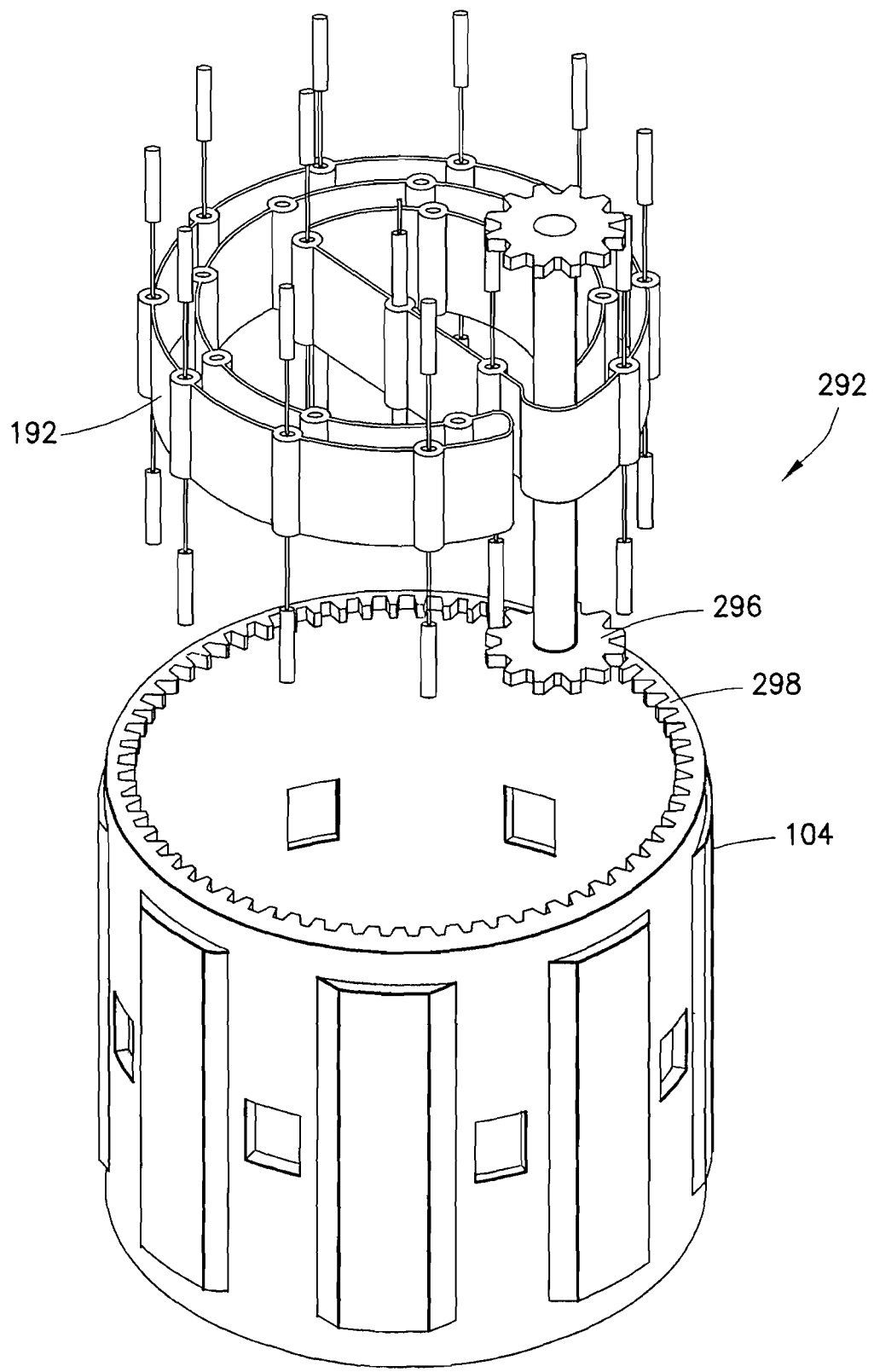
FIG. 49 is a partial perspective view of a needle changing device in accordance with still another embodiment of the present invention.

FIG. 49 is a partial perspective view of a changing device 292 in accordance with another embodiment of the present invention. As shown in FIG. 49, rather than the axial grooves 136, the changing device 292 employs a pinion gear 296 and a circumferential rack 298 to advance the needle holder 192.

FIGS. 50-52 are partial plan views illustrating alternative embodiments of needle-holders. In the embodiment shown in FIG. 50, a needle holder 300 is held in tension as the needles are about to enter a middle portion centered about the selected position, until the needles leave the middle portion. Outside the middle portion, the needle holder 300 is not tensioned, and can float freely. This embodiment is designed to accommodate a great number of needles in a given space.

In FIG. 51, two complete, separate needle holders 304 and 308 follow substantially the same path, and have substantially the same pitch (distance between needles along the needle holder). The separate needle holders 304 and 308, however, alternate which needle holder next advances a needle to the selected position.

As shown in FIG. 52, the needle holder 312 is held in tension through the middle portion by a dummy hub 316. In FIG. 52, all of the needles 200 are unused.

Figure 54:
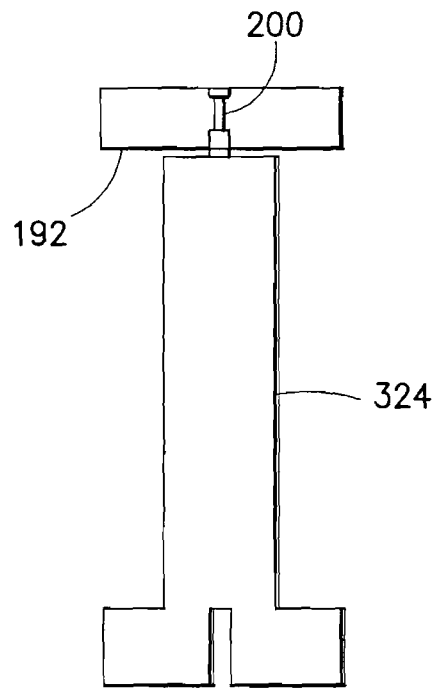
FIGS. 54-59 are perspective views of a manufacturing process of the sterility barrier of FIG. 53.
Figure 55:
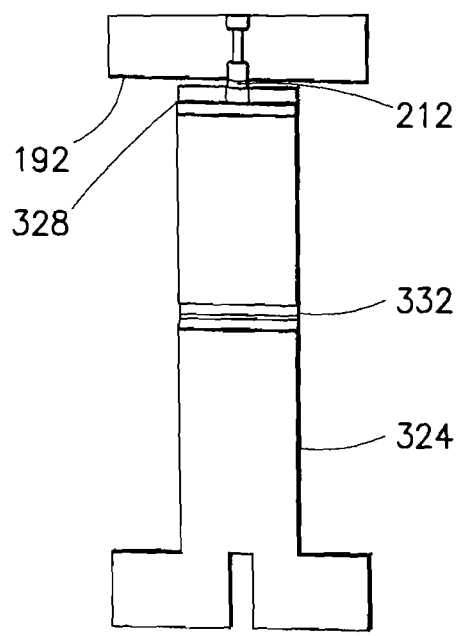
Figure 56:
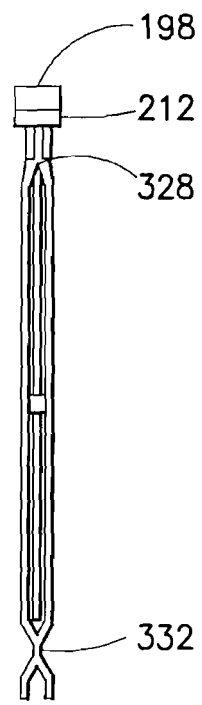
Figure 57:
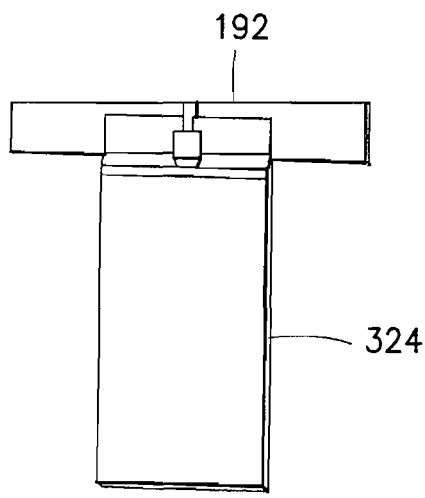
Figure 58:
Figure 59:
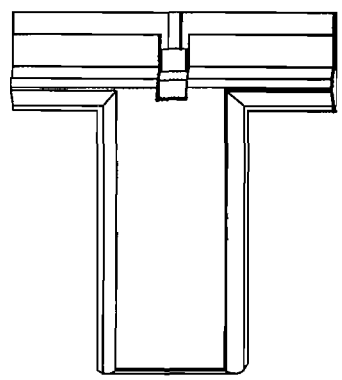

FIG. 53 is a perspective view of an alternative sterility barrier (or lower sterility barrier) 320 for the patient end 208 of the needles 200. FIGS. 54-59 are perspective views of a manufacturing process of the lower sterility barrier 320. Though the lower sterility barrier 320 is manufactured as a continuous part. In other words, the sterility barrier 328 for the needles 200 are serially connected. For clarity, however, only a single lower sterility barrier 320 is shown. As shown in FIG. 54, paper 324 is placed on opposing sides of the needle 200 connected to the needle holder 192. In the operation depicted in FIG. 55, an upper barrier 328 to the needle 200 is sealed at the hub 212, and a lower barrier 332 is sealed below the needle 200. FIG. 56 illustrates a side view of the operation illustrated in FIG. 55. Subsequently, as shown in FIGS. 57 and 58, a lower portion of the paper 324 is folded upward and bonded to the needle holder 192. FIG. 58 illustrates a side view of the operation illustrated in FIG. 57. Finally, as shown in FIG. 59, the open edges are bonded shut.

Figure 60:
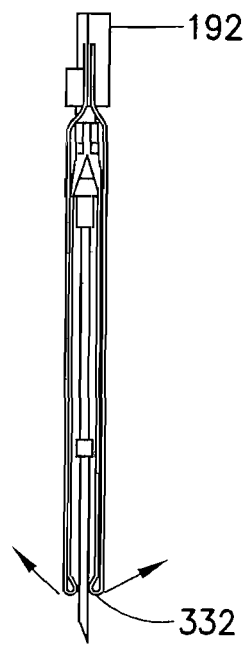
FIG. 60 illustrates removal of the sterility barrier of FIG. 53.

FIG. 60 illustrates removal of the lower sterility barrier 320. When the user moves the user dial 104 axially toward the pen injector 50, as the needle carrier 192 is moved axially toward the pen injector 50 and the needle 200 remains stationary, the paper 324 is peeled upwardly, breaking the lower barrier or bond 332 and exposing the patient end 208 of the needle 200.

Figure 61:
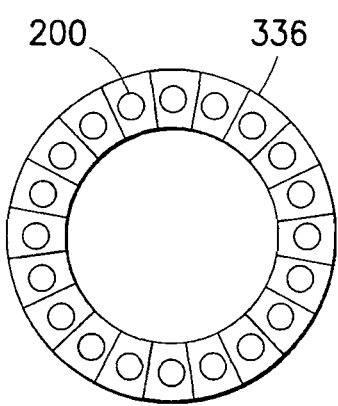
Figure 62:
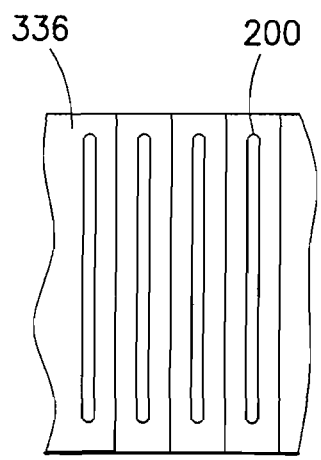

FIGS. 61-87 illustrate additional alternative sterility barriers. FIGS. 61 and 62 illustrate a sterility barrier 336 in which each needle 200 is individually stored in a paper barrier, similar to toothpick wrappers.

Figure 63:
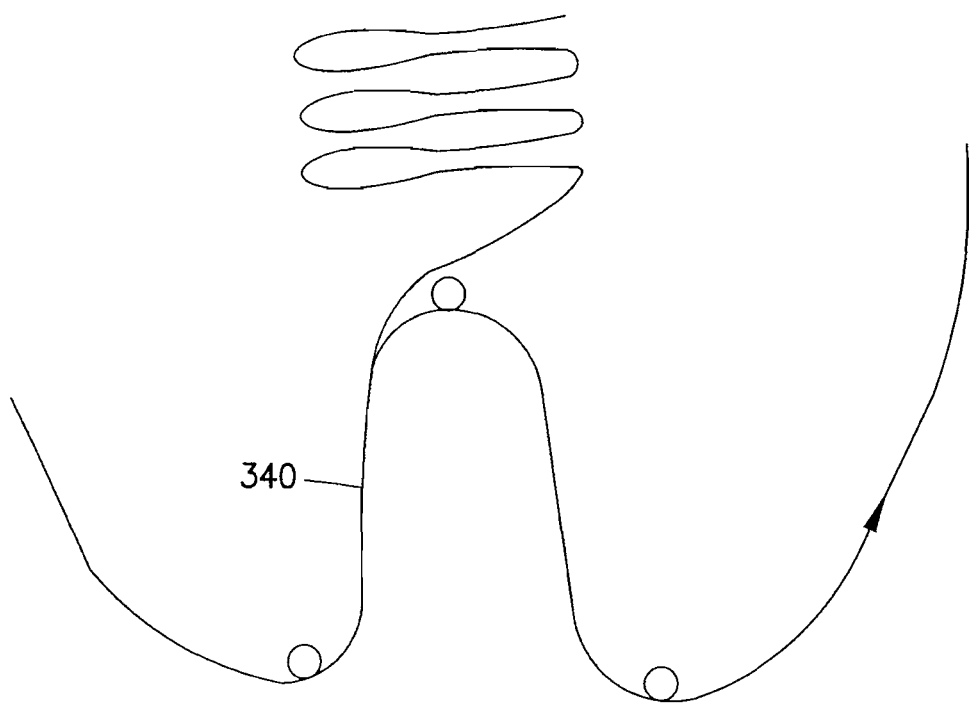
Figure 64:
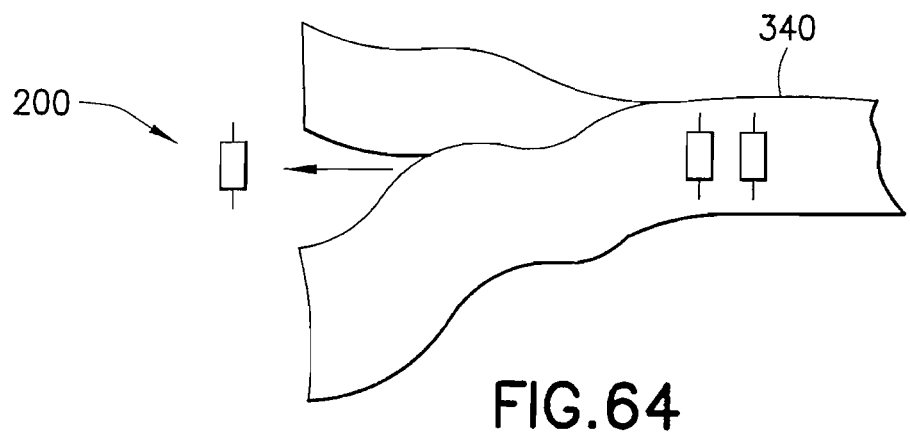
Figure 65:
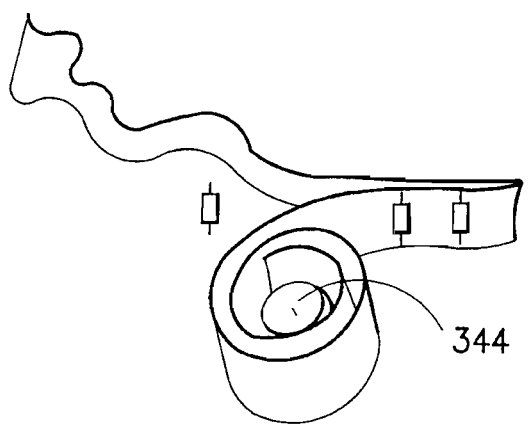
Figure 66:
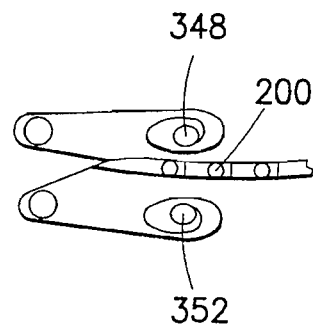

FIGS. 63-67 illustrate a sterility barrier 340 in which each needle 200 is contained between strips of paper. These embodiments take advantage of the sharp curve as the needles 200 rotate into the selected position to split the strips of paper (FIG. 63). According to one embodiment (FIG. 65), a take-up wheel 344 takes up only one of the two parts of the paper strip. According to another embodiment, take-up wheels 348 and 352 take up both parts of the paper strip (FIG. 66). According to yet another embodiment, neither of the strips is taken up, but instead, merely split at the sharp curve (FIG. 64). According to still another embodiment (FIG. 67), as the needle holder 192 rounds the sharp curve, two separate tracks are created for the two strips. This causes the needle 200 to be freed from the strips at the selected position. Then, as the needle 200 moves out of the selected position, the tracks direct the paper strips to re-cover the needle 200. In this embodiment, the strips may be held together by an adhesive, and thus when the paper strips re-cover the needle 200 as the needle 200 moves out of the selected position, the adhesive rejoins the paper strips.

Figure 68:
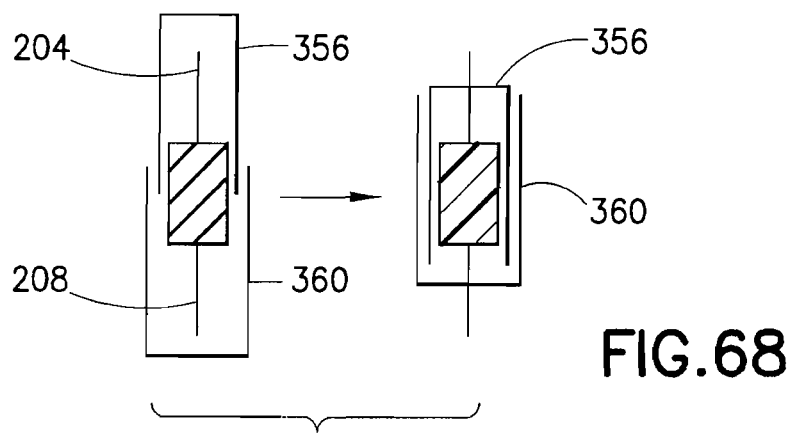
Figure 69:
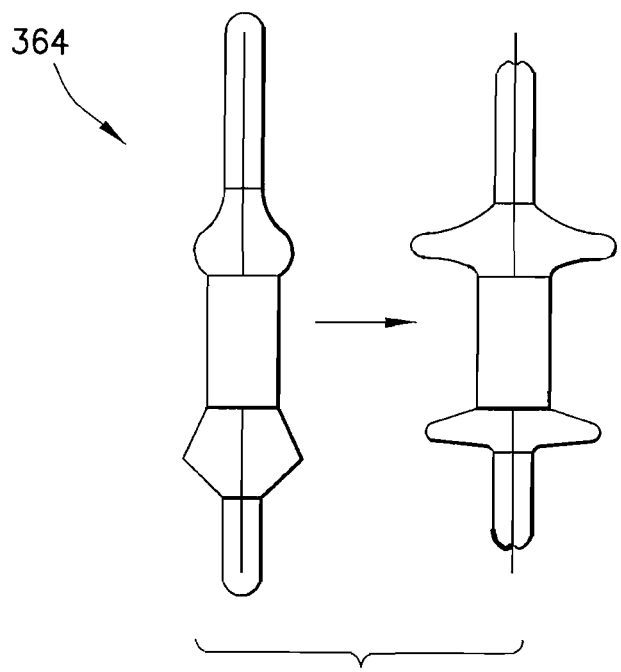
Figure 70:
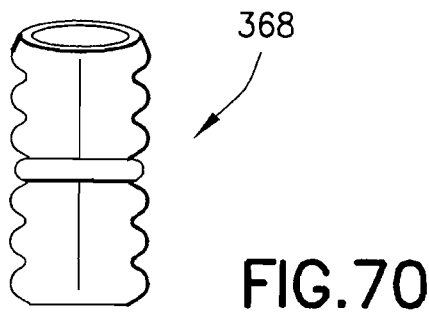

FIGS. 68-70 illustrate three collapsible sterility barriers. As shown in FIG. 68, rigid, inter-fitting cups 356 and 360 cover the septum and patient ends 204 and 208 of the needle 200. As the user moves the user dial 104 axially toward the pen injector 50, the inter-fitting cups 356 and 360 are pressed together and respectively pierced by the septum and patient ends of the needle 200. According to one embodiment, the inter-fitting cups 356 and 360 are made of plastic. Similarly, FIGS. 69 and 70 respectively illustrate sterility barriers 364 and 368 that collapse as the user moves the user dial 104 axially toward the pen injector 50.

Figure 71:
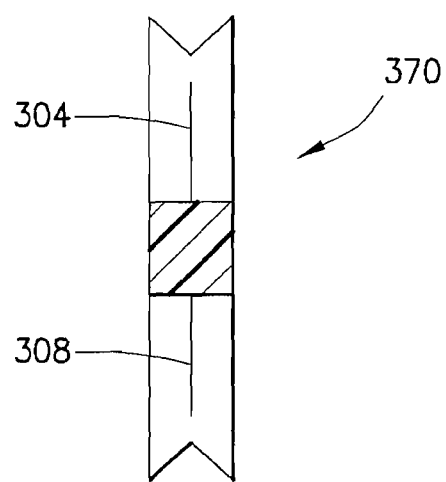
Figure 72:
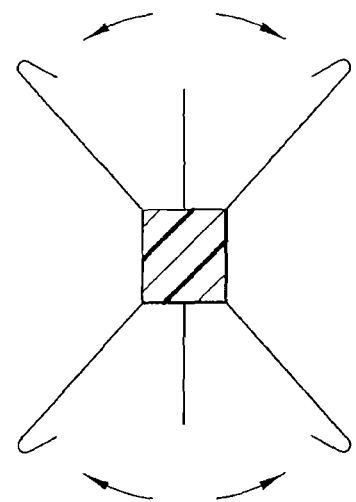
Figure 73:
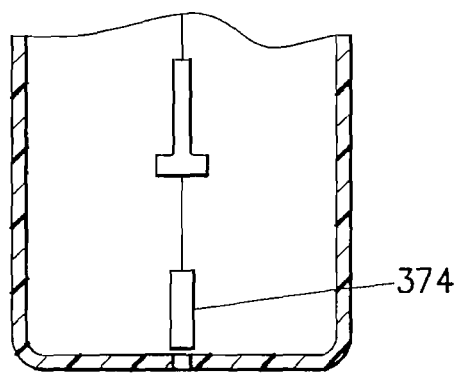
Figure 74:
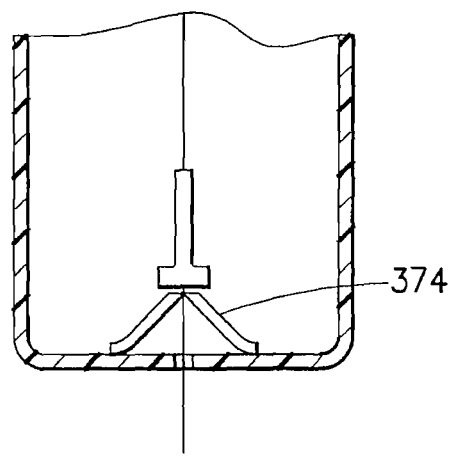

FIGS. 71 and 72 illustrate a rigid sterility barrier 370 that breaks apart during needle engagement. Breaking apart can be achieved by axial penetration of the top and bottom of the sterility barrier 370 with a more rigid object. Alternatively, the sterility barrier 370 can be broken apart by compressing the hub of the sterility barrier laterally (from both sides), which, as a result, breaks the rigid barrier apart. The sterility barrier 370 covers both the septum and patient ends 304 and 308 of the needle 200. In contrast, a rigid sterility barrier 374 shown in FIGS. 73 and 74 only covers the patient end 308 of the needle 200. According to one embodiment, the sterility barriers 370 and 374 are made of plastic. According to one embodiment, the sterility barriers 370 and 374 are integrally formed as a single unit with a needle hub via, for example, living hinges, which are broken apart as the needle is extended out of the device 100

Figure 75:
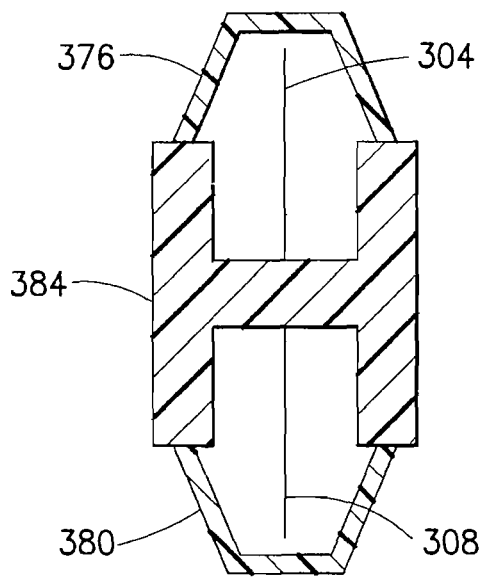
Figure 76:
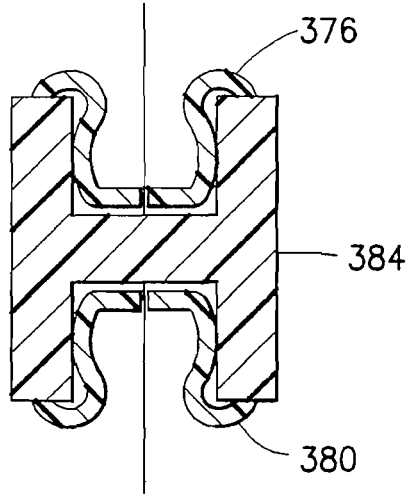

FIGS. 75 and 76 illustrate flexible (elastomeric) domes 376 and 380 connected to a hub 384 and respectively covering septum and patient ends 304 and 308 of the needle 200. According to one embodiment, the domes 376 and 380 are connected to the hub 384 by, for example, living hinges. As shown in FIG. 76, the domes 376 and 380 collapse into the needle hub 384 upon engagement. According to one embodiment, the domes 376 and 380 are collapsible but are not removable. According to one embodiment, the domes 376 and 380 are invert inwardly on themselves and stay inverted. During the inversion, the needles 200 poke through the barriers.

Figure 77:
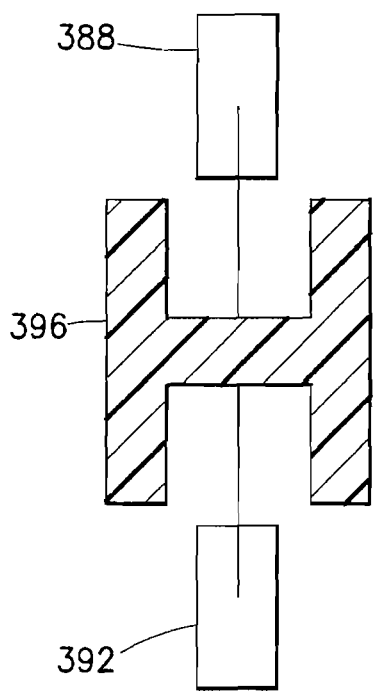
Figure 78:
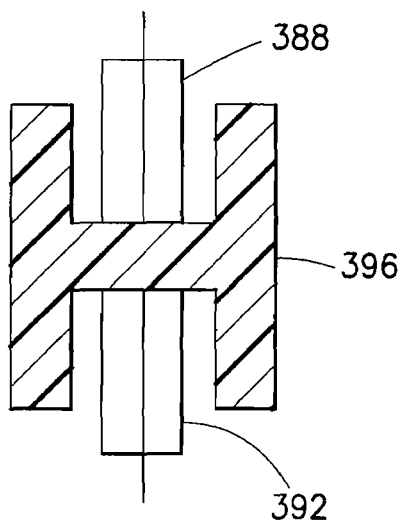

FIGS. 77 and 78 illustrates hollow core caps 388 and 392. As shown in FIG. 78, the hollow core caps collapse into the needle hub 396 upon engagement. According to one embodiment, the hub geometry accommodates the caps 388 and 392 to limit the extended length of the needle 200 past the pierced end of the respective caps 388 and 392.

FIG. 79-81 illustrates an embodiment in which a sterility barrier 400 is peeled back by a rigid blade 404 disposed in a bottom floor of the inner track 124. As shown in FIG. 80, the side barriers 408 and 412 are tortuous path barriers. In addition, these tortuous path barriers 408 and 412 help maintain alignment of the house of the sterility barrier 400 during assembly. As shown in FIG. 81, as the user dial 104 is moved axially toward the pen injector 50, the rigid blade 404 peels back the sterility barrier 400.

FIG. 82 illustrates a rigid lower sterility barrier 416 that connects to a lower portion of the hub 212. The sterility barrier 416 does not contact the patient end 208 of the needle 200. In operation, the user simply pulls the sterility barrier 416 through an opening in the floor of the inner track 124 prior to delivery of the medicament.

FIGS. 83 and 84 illustrates a rigid upper sterility barrier 420 connected to a hub 424 via an adhesive 428. As the needle 200 is advanced axially toward the pen injector 50, the septum end 204 pierces the sterility barrier 420 and the cartridge septum 16 as the sterility barrier 420 slides down the hub 424.

Figure 67:
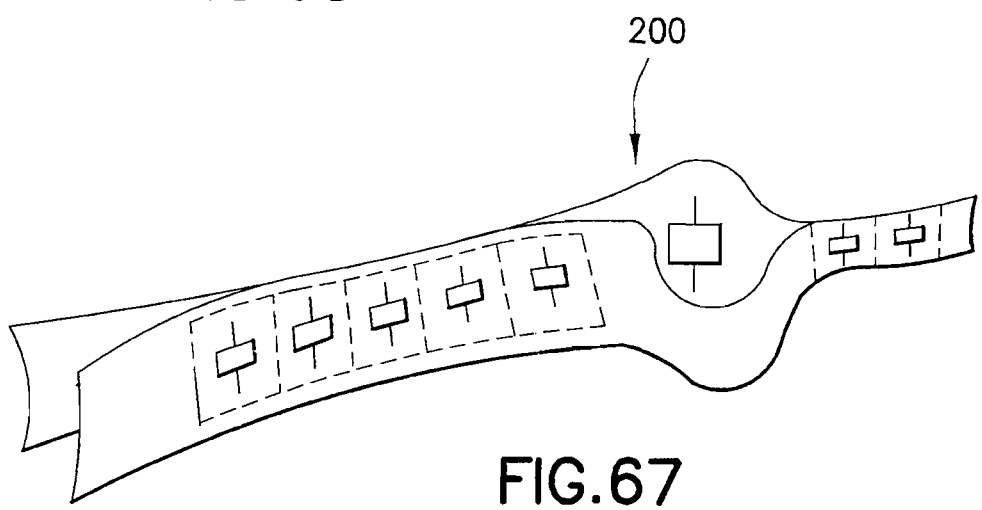
Figure 85:
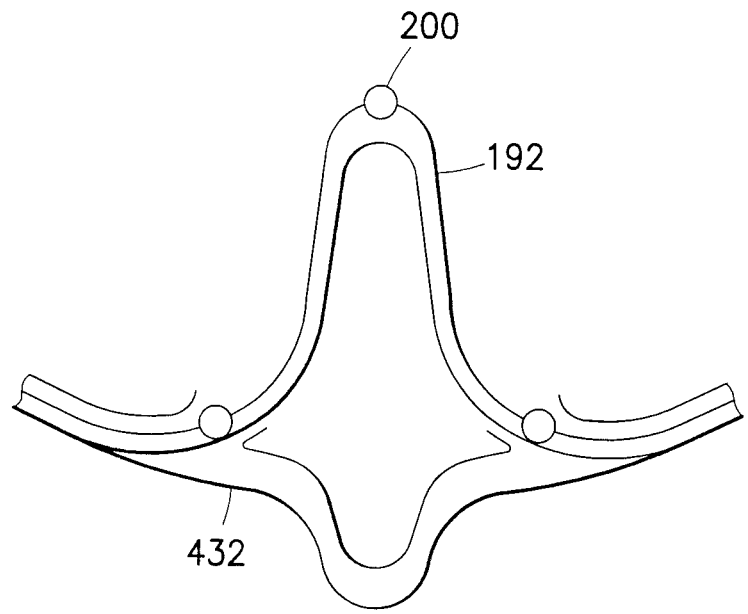

Similar to the embodiment of FIG. 67, FIG. 85 illustrates a sterility barrier 432 in which the needle 200 in the needle holder 192 is freed from the sterility barrier 432 prior to moving into the selected position. Subsequent to moving out of the selected position, the needle 200 rejoins the sterility barrier 432.

Figure 86:
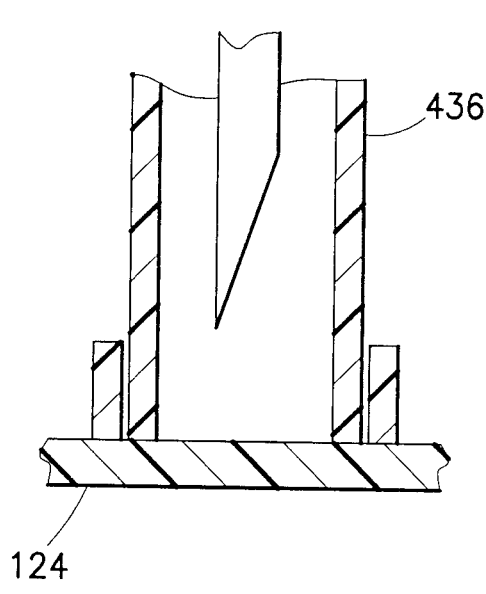
Figure 87:
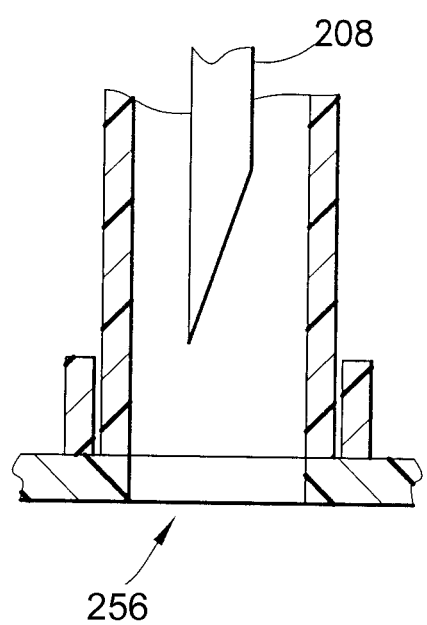

As shown in FIGS. 86 and 87, sterility barrier 436 (with the distal end thereof being open) rides along the floor of the inner track 124. As shown in FIG. 87, however, in the selected position, there is an opening 256 in the floor of the inner track 124, thereby permitting the patient end 208 to be exposed.

Figure 88:
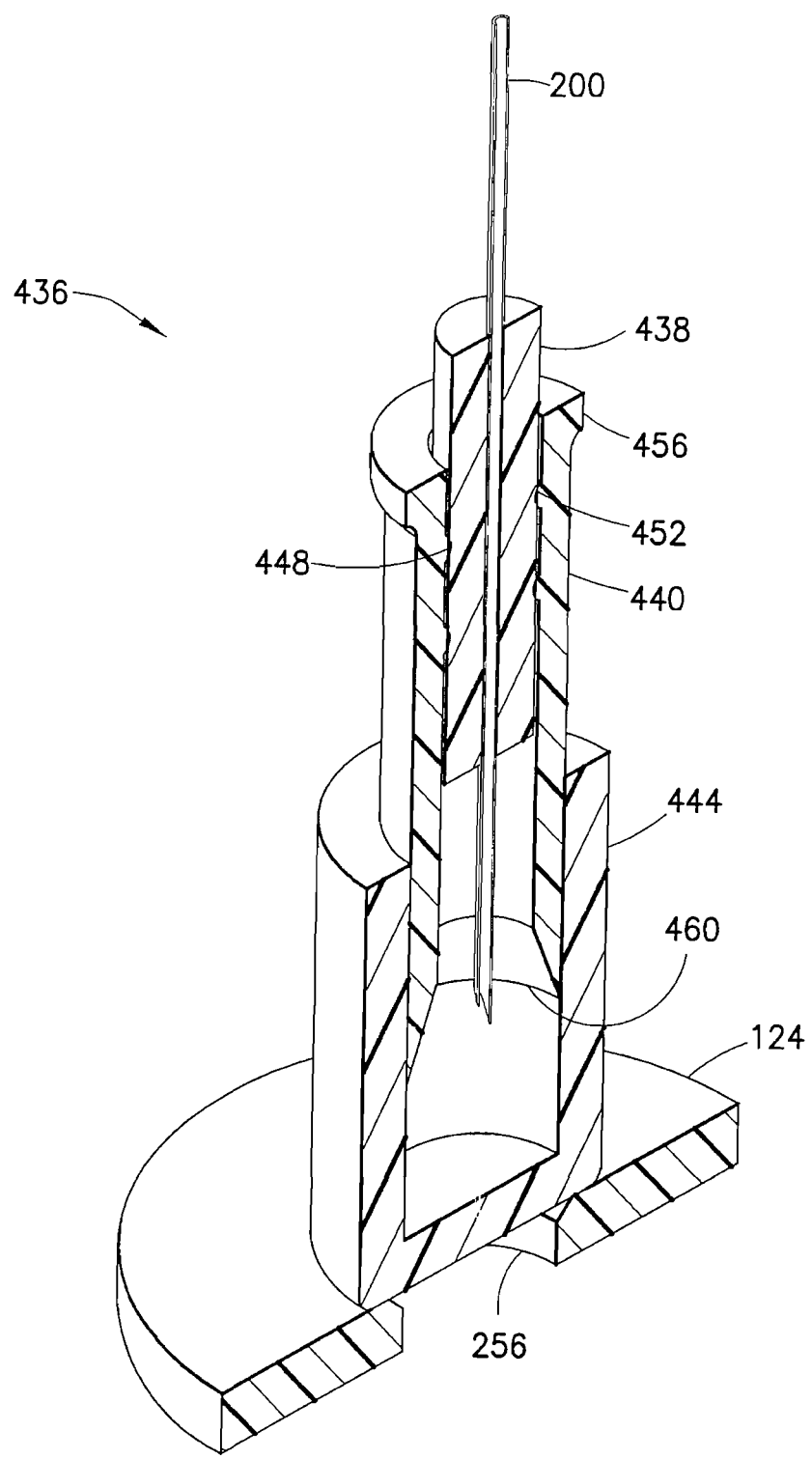

FIG. 88 is a partial perspective view in cross-section of an another alternative sterility barrier 436 for the changing device 100. For clarity, the patient end of only a single needle 200 is shown. The sterility barrier 436 includes a lower needle hub 438 disposed around a portion of the patient and of the needle 200, an introducer 440, and a boot 444. The lower needle hub 438 includes at least one circumferential depression 448 selectively engaged with a corresponding circumferential protrusion 452 on the introducer 440. The introducer 440 also has a shoulder 456 and a beveled distal cutting tip or chisel 460.

As shown in FIG. 88, the floor of the inner track 124 has the opening 256 therethrough. According to one embodiment, the opening 256 is disposed substantially at a central axis of the inner track 124.

Shown in mid-operation in FIG. 88, as the needle 200 is distally displaced relative to the inner track 124, because of the frictional engagement between the circumferential protrusion 452 and the circumferential depression 448, as well as the frictional engagement between the introducer 440 and the boot 444, the sterility barrier 436 travels with needle 200 until the boot 444 contacts the floor of the inner track 124.

With continued distal displacement of the needle 200 relative to the inner track 124, the friction between the boot 444 and the introducer 440 is overcome and the distal cutting tip 460 cuts the floor of the boot 444 and travels distally along with the needle 200 until the shoulder 456 contacts a proximal end of the boot 444. With further distal displacement of the needle 200 relative to the inner track 124, the friction between the circumferential depression 448 and the circumferential protrusion 452 is overcome and the distal end of the needle 200 is exposed outside of the changing device 100 through the opening in the boot 444 cut by the distal cutting tip 460 and through the opening 256 in the floor of the inner track 124. As the needle 200 is re-sheathed within the inner track 124, the needle hub 438, introducer 440, and the boot 444 maintain the relative positions that they possessed at the distal end of the needle's stroke.

According to one embodiment, the distal cutting tip 460 of the introducer 440 is disposed around the entire circumference of the distal end of the introducer 440. According to another embodiment, the distal cutting tip 460 is disposed only around a portion of the circumference (for example, 180° or 270°) of the distal end of the introducer 440. In such an embodiment, the introducer 440 cuts a flap that folds out of the way when the needle 200 is exposed outside of the changing device 100. Such an embodiment also prevents particulate (for example, a piece entirely cut out of the boot 444) from falling out of the changing device 100.

Figure 89:
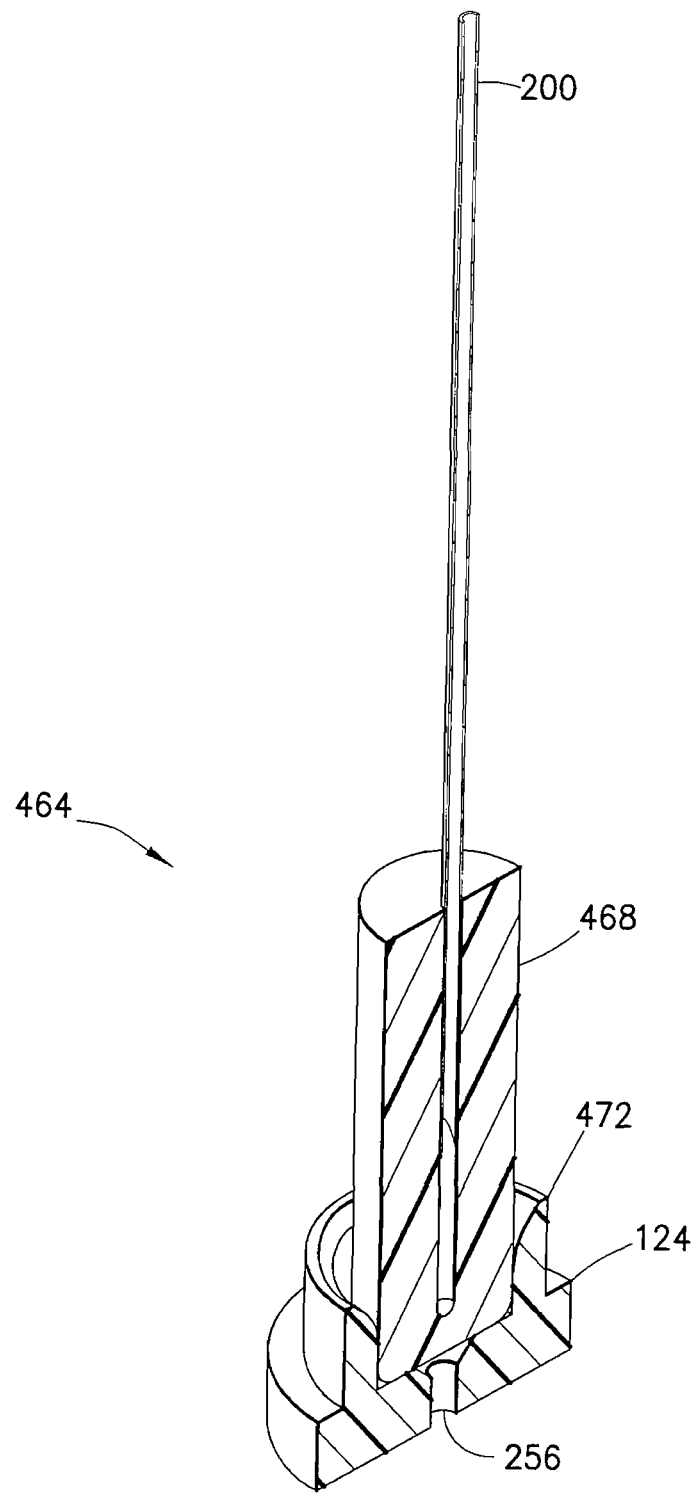

FIG. 89 is a partial perspective view in cross-section of another sterility barrier 464 for the changing device 100. For clarity, the patient end of only a single needle 200 is shown. The sterility barrier 464 includes a boot 468. As shown in FIG. 52, the floor of the inner track 124 has the opening 256 therethrough. According to one embodiment, the opening 256 is disposed substantially at a central axis of the inner track 124.

Shown in mid-operation in FIG. 89, as the needle 200 is distally displaced, the boot 468 travels with needle 200 until the boot 468 contacts the floor of the inner track 124. With further distal displacement, the needle 200 pierces the boot 468 and is exposed outside of the changing device 100 through the opening 256. According to one embodiment, the floor of the inner track 124 also includes a collar 472 with a beveled proximal edge for guiding the boot 468. As the needle 200 is re-sheathed within the inner track 124, the boot 468 maintains the relative position that it possessed at the distal end of the needle's stroke.

Figure 90:
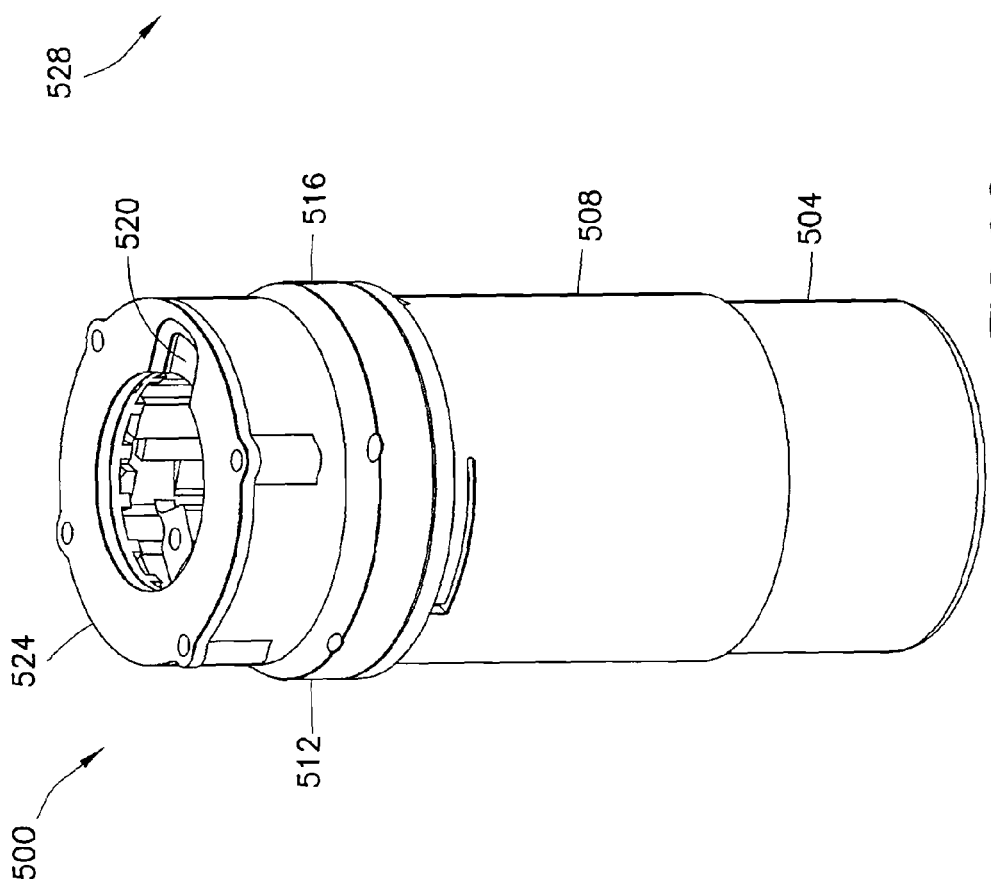
FIG. 90 is a perspective view of a needle changing device in accordance with another embodiment of the present invention.

FIG. 90 is a perspective view of a needle changing device 500 (for brevity, hereinafter changing device 500) in accordance with another embodiment of the present invention. As shown in FIG. 90, the changing device 500 includes a bottom housing or inner housing 504, a user dial or user interface 508, a cap 512, a user button or second user interface 516, a needle counter 520, and a top cover 524. Internally, as discussed in greater detail below, the changing device 500 also includes the fixed mount 528, a maze or guide member 532, and a fixed post 536.

Figure 91:
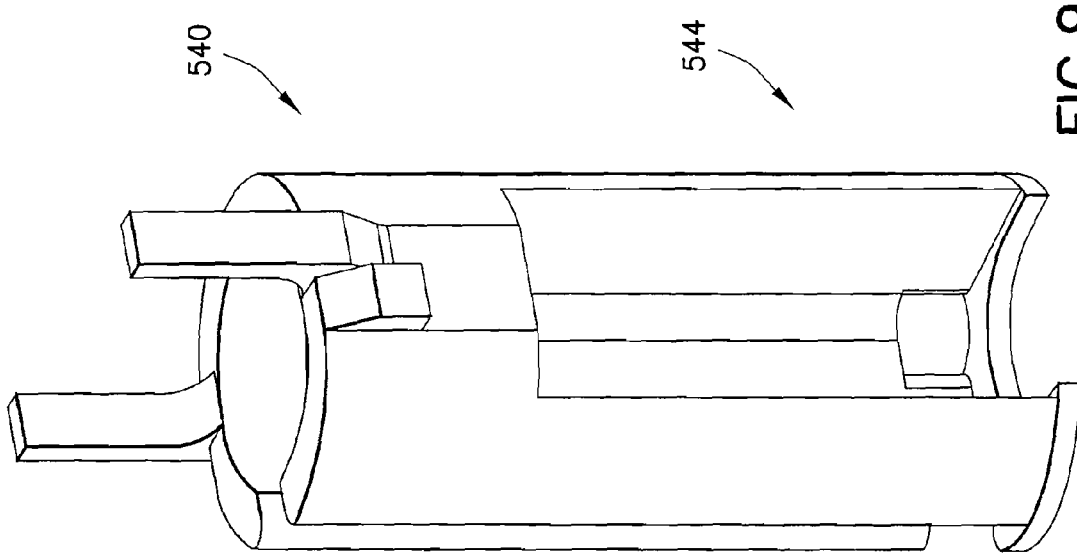
FIGS. 91 and 92 are perspective side and top views, respectively, of a fixed mount of the needle changing device of FIG. 90.
Figure 92:
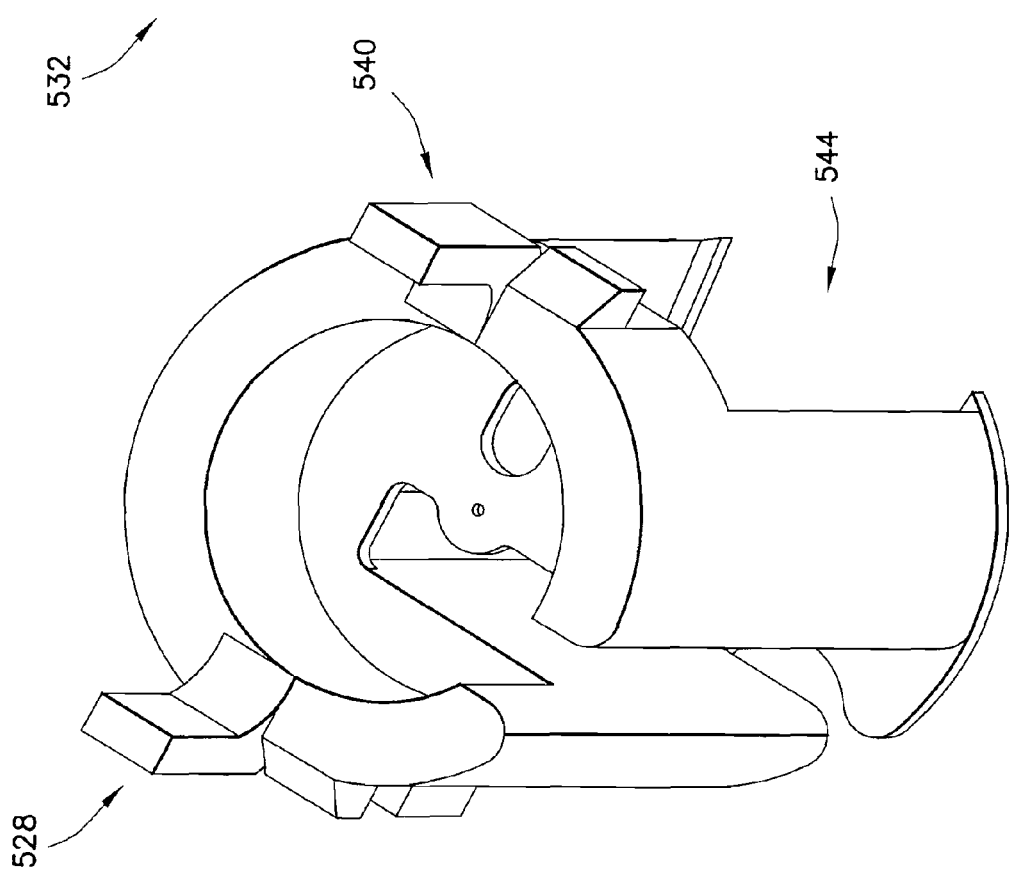

FIGS. 91 and 92 are perspective side and top views, respectively, of the fixed mount 528. As shown in FIGS. 91 and 92, fixed mount 528 includes a sliding guide 540 and an opening 544 for receiving the fixed post 536. The sliding guide 540 functions substantially similarly to the sliding guide 176 of the changing device 100. Accordingly, detailed description of the sliding guide 540 is omitted for brevity. The fixed mount 528 includes means for connecting the fixed mount with the pen injector 50. According to one embodiment, the means for connecting the pen injector 50 include internal threads. According to another embodiment means for connecting the pen injector 50 include L-shaped slots that mate with radial protrusions on the pen injector 50 for a relative sliding and then rotating connection. Additionally, according to one embodiment (not shown), the changing device 500 includes a fixed floor fixedly secured to the fixed mount 528.

Figure 93:
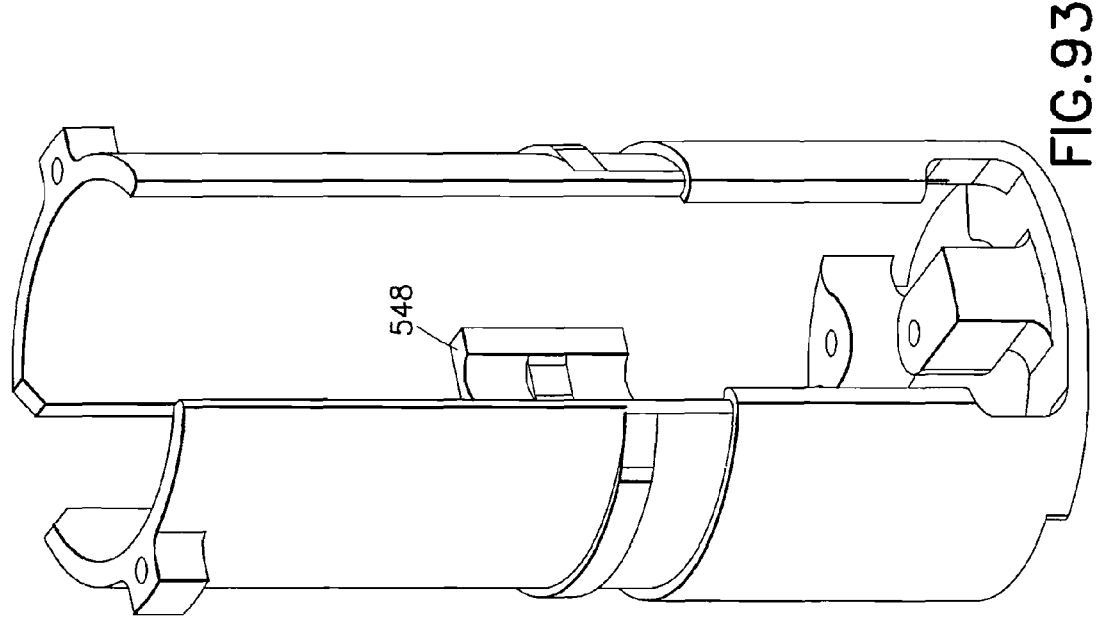
FIGS. 93 and 94 are perspective side and top views, respectively, of a maze of the needle changing device of FIG. 90.
Figure 94:
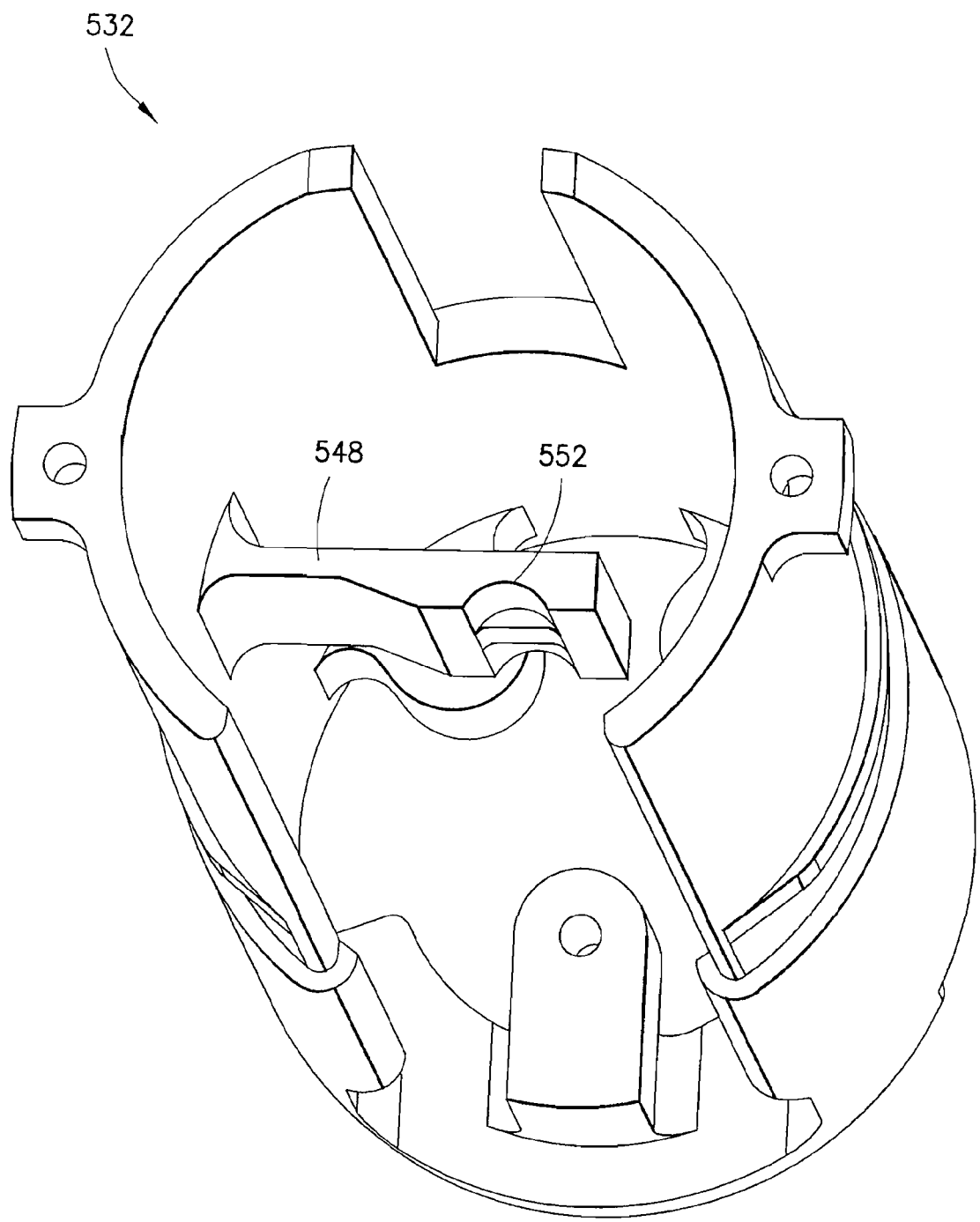

FIGS. 93 and 94 are perspective side and top views, respectively, of the maze 532. Like the maze 178 of the changing device 100, the maze 532 includes a cantilevered needle snap arm 548 with a nesting portion 552 thereon. The maze 532 slidably fits about the fixed mount 540 so that the needle snap arm is disposed within a central portion of the fixed mount 540.

Figure 95:
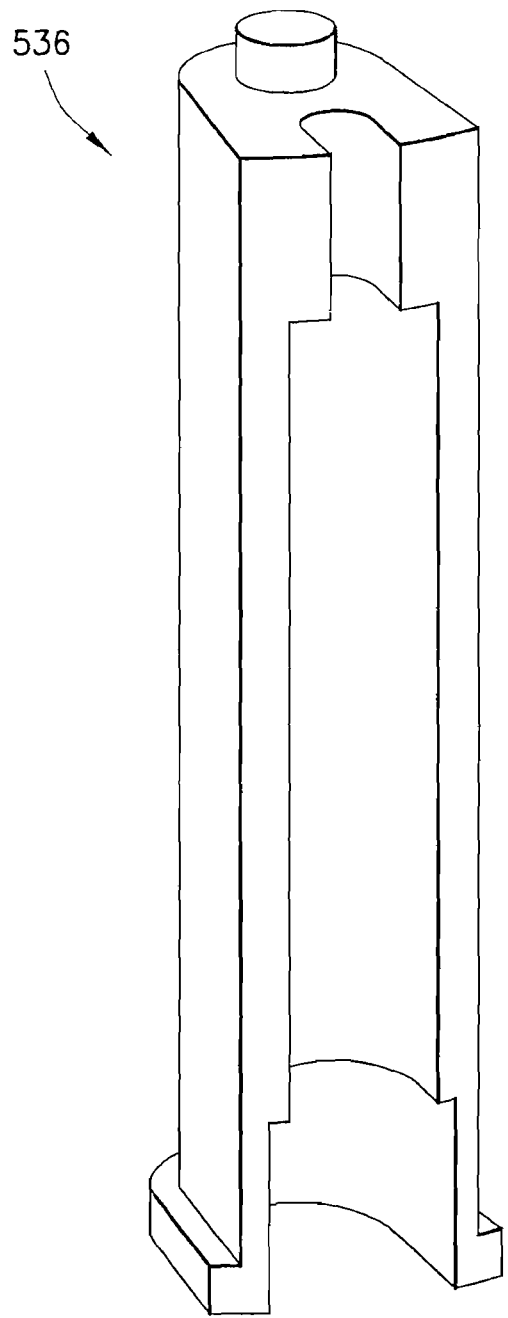
FIGS. 95 and 96 are perspective front and rear views, respectively, of a fixed post of the needle changing device of FIG. 90.
Figure 96:
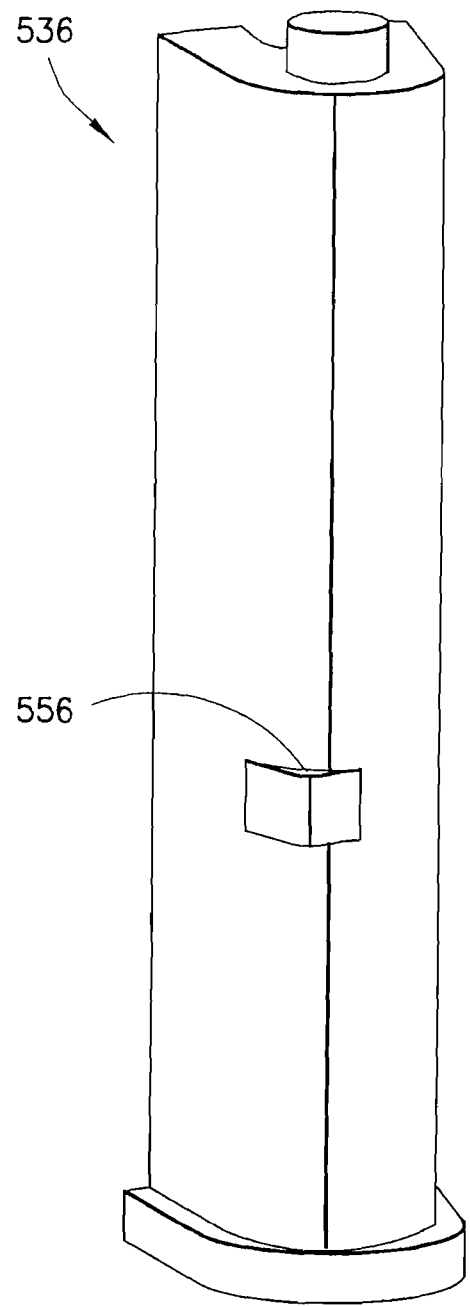

FIGS. 95 and 96 are perspective front and rear views, respectively, of the fixed post 536. The fixed post 536 includes a lock feature 556, which functions similarly to the lock feature 232 of the changing device 100. In the changing device 100, the locking feature 232 is disposed on a portion of the fixed mount 172, which is integrally formed as a unitary structure. In the changing device 500, however, to potentially simplify manufacturing and assembly, the fixed post 536 is a separate unit from the fixed mount 528. As described in greater detail below, subsequent to the installation of a flexible band or needle holder 560 (FIG. 97), the fixed post 536 is inserted into the opening 544 of the fixed mount 528 and fixedly secured to the fixed mount 528. The fixed post 536 is secured to the fixed mount 528 by, for example, one or more screws, or by a snap-fit mechanism.

In conjunction, the maze 532 and the fixed post 536 form a circuitous path for the needle holder 560. As illustrated in FIG. 97, the needle holder 560 is shaped into the circuitous path with the identified needle 200 being disposed in the activated position.

The user dial 508, shown in FIG. 98, includes a plurality of internal engaging structures or radially inward protrusions 572. During rotation of the user dial 508, the inward protrusions 572 engage upper and lower needle guides 564 and 568 (see FIG. 97) to advance the needle holder along the circuitous path.

Figure 100:
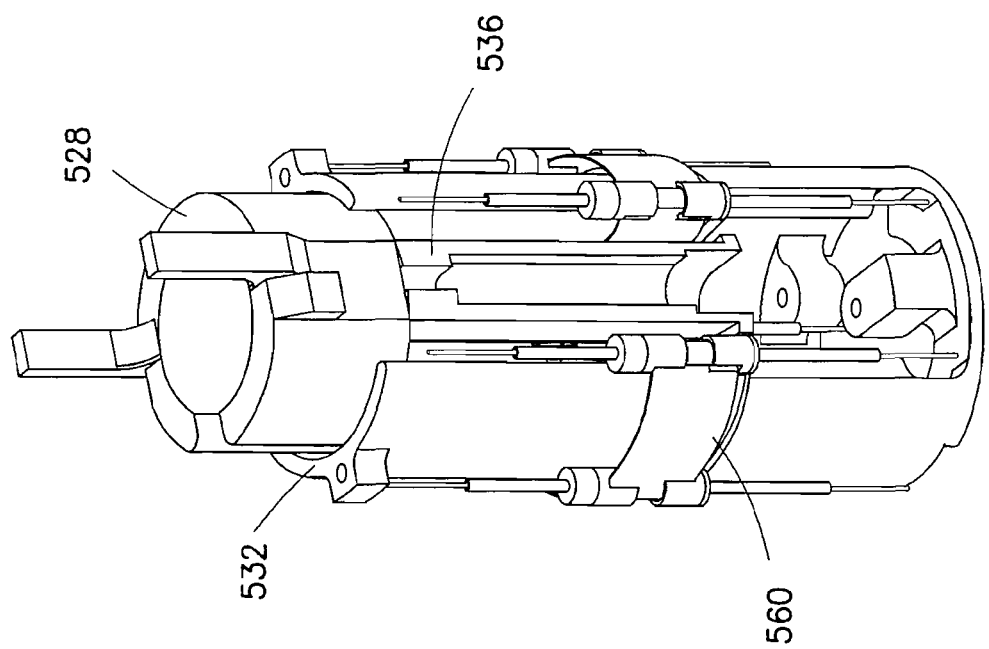
FIGS. 99-108 illustrate a method of assembly of the needle changing device of FIG. 90.
Figure 99:
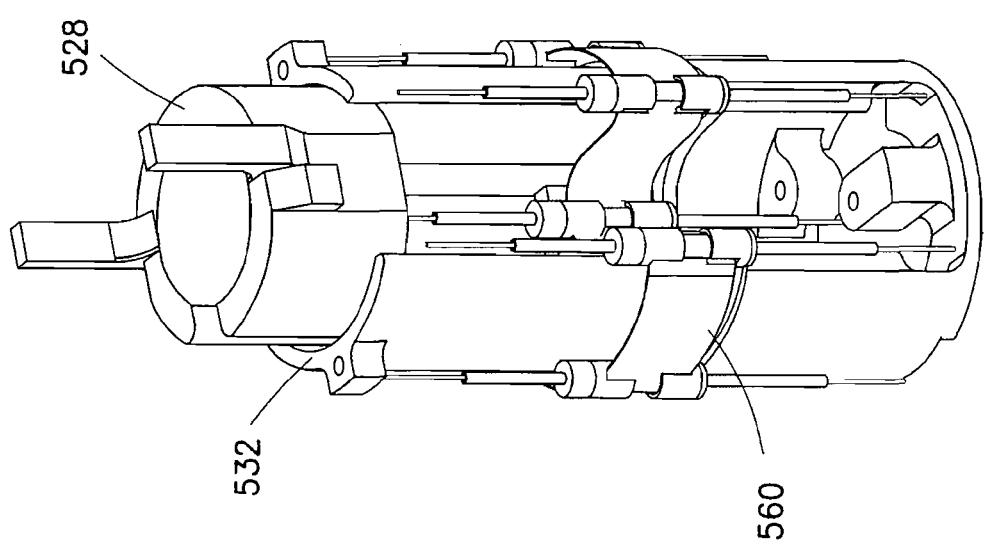
Figure 101:
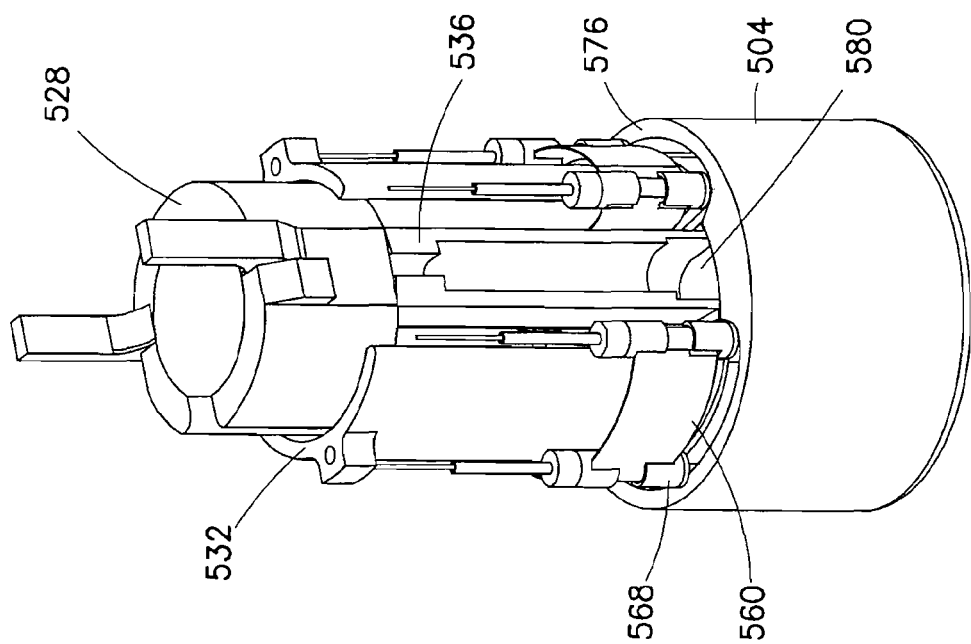

FIGS. 99-108 illustrate a method of assembly of the needle changing device 500. Initially, an assembler axially slides the fixed mount 528 and the maze 532 together. Subsequently, as shown in FIG. 99, the assembler places the needle holder 560 over the fixed mount-maze assembly. Next, the assembler inserts the fixed post 536 into the opening 544 to form the circuitous path (FIG. 100). Then, as shown in FIG. 101, the assembler secures the bottom housing 504 to the maze 532 using, for example, screws or bolts. Also shown in FIG. 101, a proximal surface 576 of the bottom housing 504 interacts with the lower needle guides 568 and functions as a guiding surface for the needle holder 560 as it travels on the outer surface of the maze 532 along the circuitous path. Additionally, the bottom housing 504 includes a radially inward protrusion 580 that provides support for the fixed post 536 during the axial sliding of, for example, the user dial 508, the bottom housing 504, and the maze 532.

Figure 102:
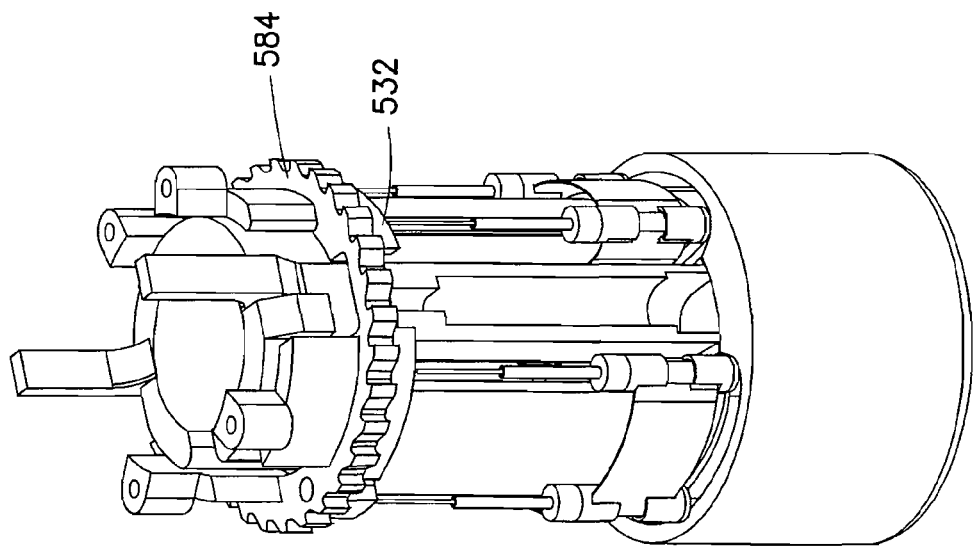
Figure 104:
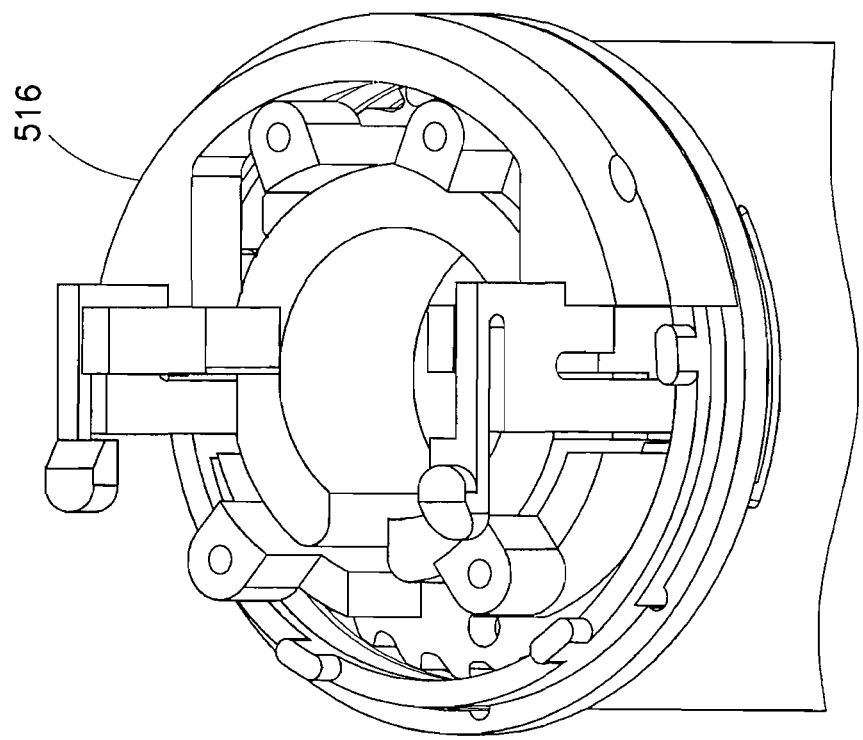
Figure 103:
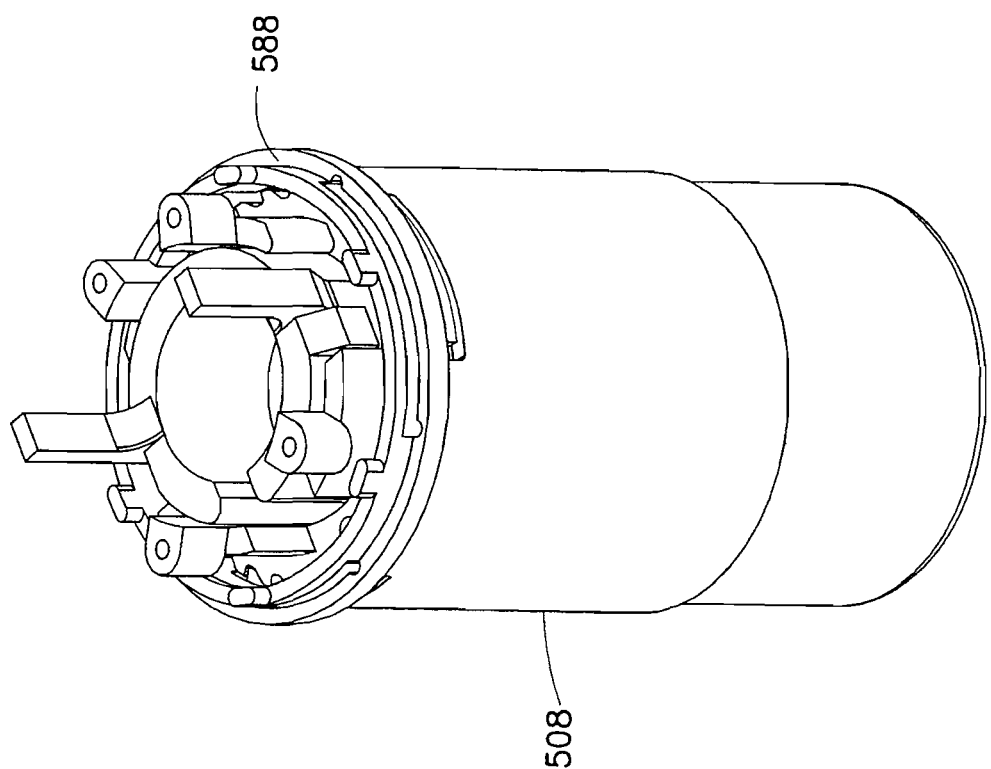
Figure 105:
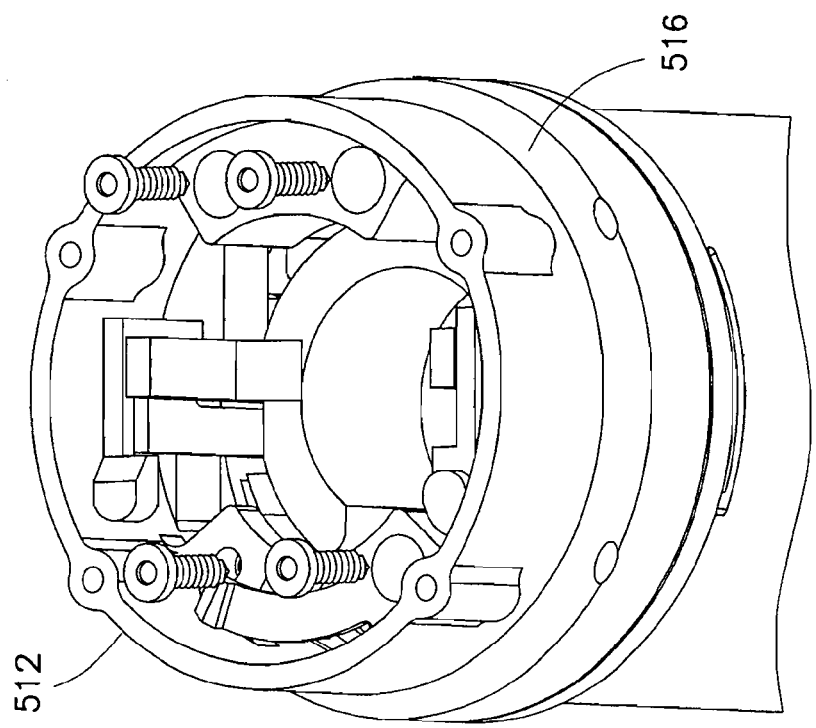

Next, as shown in FIG. 102, the assembler secures a dial ratchet 584 for permitting rotation of the user dial 508 in only a single direction to the maze 532. Subsequently, the assembler places the user dial 508 and the dial top 588 secured thereto onto the device (FIG. 103). Then, as shown in FIGS. 104 and 105, the assembler installs the user button 516 and secures the cap 512 to the dial ratchet 584 using, for example screws or bolts.

Figure 106:
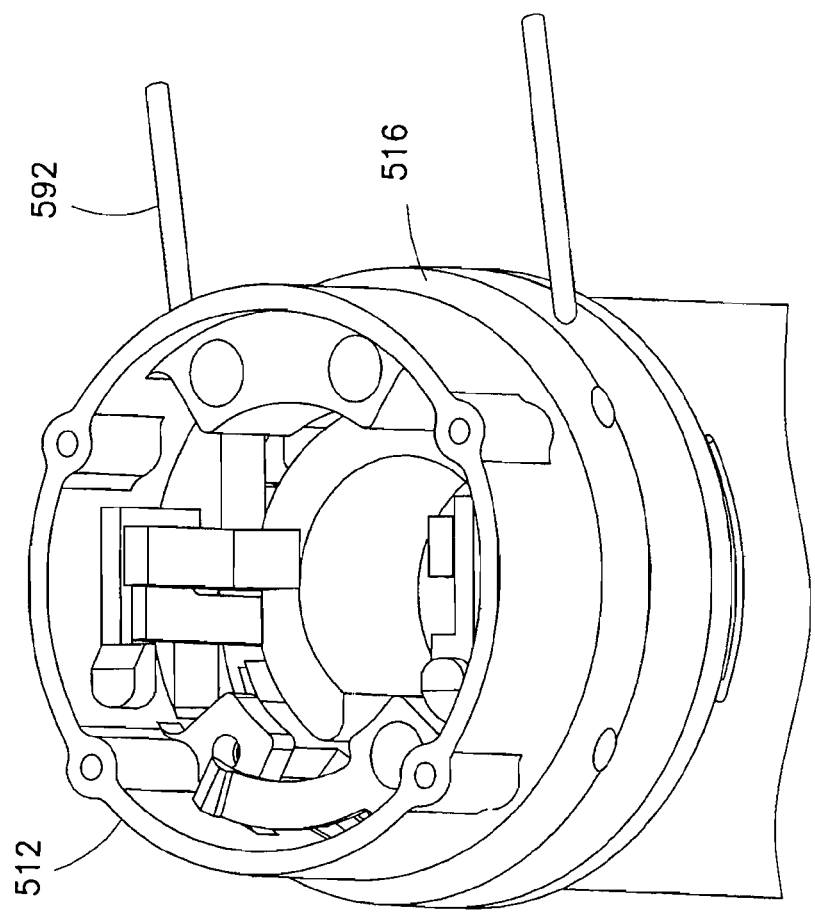
Figure 108:
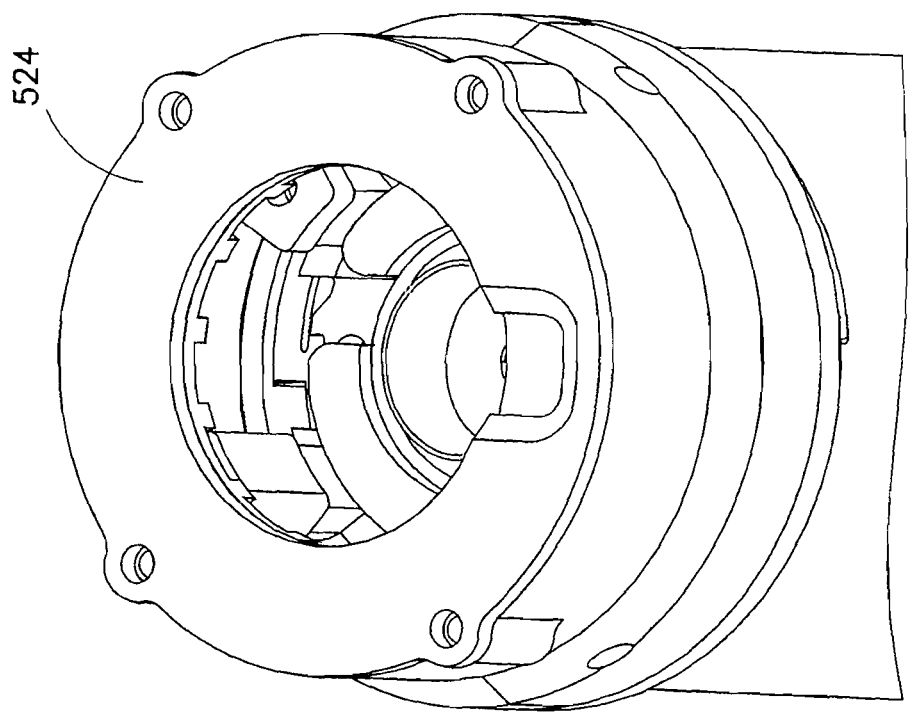
Figure 107:
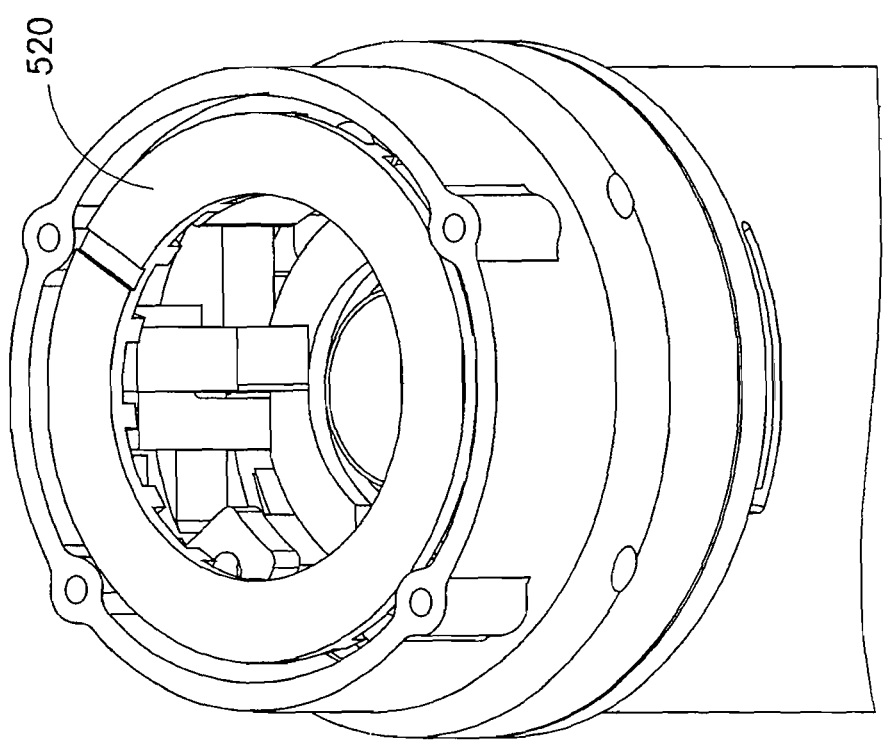

As shown in FIG. 106, the assembler subsequently inserts guide pins 592 into the user dial 516 and the cap 512. The guide pins 592 are fixed to the user button 516 using, for example, an adhesive. Finally, as shown in FIGS. 107 and 108, the assembler inserts the needle counter 520 and fixes the top cover 524 to the device.

In operation, similar to the changing device 100, the changing device 500 is first connected to pen injector 50. Subsequently, the user rotates the user dial 508 to displace the needle holder 560 along the circuitous path so that a selected one of the plurality of needles 200 is disposed at the activated position. This rotation of the user dial 508 also radially extends the user button 516. Next, the user proximally slides the user dial 508. This action exposes the patient end of the needle 200 outside of the changing device 500 and fluidly connects the non-patient end of the needle 200 with the medicament container 12 of the pen injector 50.

Then, after delivering the medicament dosage, the user presses the user button 516 radially inward, thereby advancing the needle counter 520 and permitting the subsequent distal sliding of the user dial 508. This distal sliding of the user dial 508 re-sheathes the patient end of the needle 200 within the bottom housing 504 and disconnects the non-patient end of the needle 200 from the medicament container 12. The distal sliding of the user dial 508 also permits subsequent rotation of the user dial 508 to select another one of the plurality of needles 200.

Figure 109:
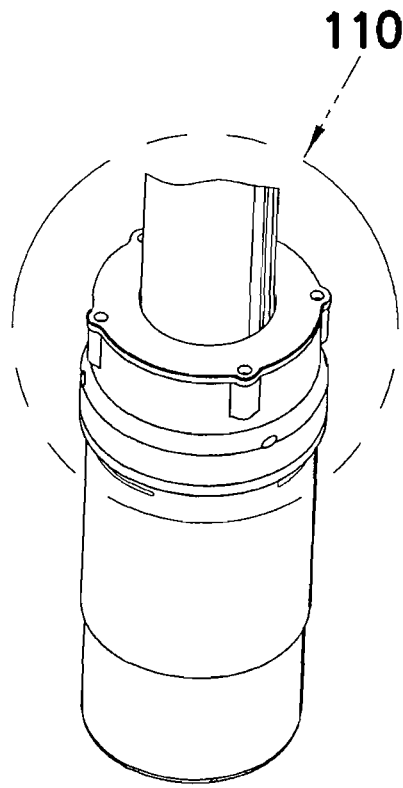
FIGS. 109 and 110 are partial perspective views illustrating an embodiment of the present invention without a user button.
Figure 110:
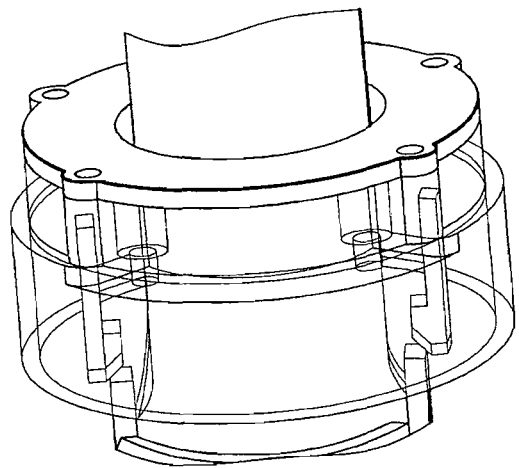

According to one embodiment shown in FIGS. 109 and 110, rather than the user button 120, the changing device 100 or 500 includes a simple passive snap that holds the device in a state ready to deliver medicament.

Although the previously-described embodiments refer to pen injection devices, it will be understood by one skilled in the art that embodiments of the present invention may also be used with other medicament injection devices, such as syringes.

Typical insulin delivery pens require users to change needles after each injection. These needles take up to six user steps to install and remove from the pen; in addition, the user is vulnerable to accidental needle sticks when manipulating the needle. Embodiments of the present invention provide novel means for changing needles in a contained, efficient, and user-friendly manner. An array of needles is contained within the device, attached to the end of a typical pen injector 50, or likewise, integrated into a specially designed delivery device. The device itself has an exterior twisting dial for the user to advance a fresh needle to the delivery position. This dial then can be pulled in the proximal direction of the pen body. As the user pulls back on the dial, the proximal end of the new needle pierces the pen cartridge septum, and the distal end exposes itself for insertion into the delivery site. According to one embodiment, when the delivery is complete, the device springs back into the initial un-pulled state, removing the needle from the pen septum and sheathing the exposed distal end of the needle. According to another embodiment, the user slides the device back into the un-pulled state. The user may now advance the next needle into the delivery or selected position and start the process again.

Within the device, a maze-like path positions the needles around the distal end of the pen injector. One needle is clamped in the delivery position, directly under the septum, whereas the other needles sit at the same vertical height relative to the pen. When the device is pulled up toward the pen, the delivery needle slides through its needle hub, piercing the septum. The other needles move to a higher level up the pen body, allowing the distal end of the delivery needle to be exposed. According to one embodiment, after delivery, the delivery needle is then removed from the septum via a spring which transmits force to the same clamping mechanism that lifted the needle into the septum. The delivery needle, removed from the septum returns to the same height (along the pen) as the remaining needles. The used needle is now ready to be moved in the circuitous path, away from the delivery position, and a new needle advances and takes its place. The process can then be repeated.

Currently there are no fully automatic needle changing devices on the market. There are devices that aid with individual steps of the needle changing process, including needle storage, needle attachment, needle removal, and needle disposal. None of these devices, however, integrates the needle changing processes into a single device.

The circuitous band of needles housed within the present device serves as an excellent storage mechanism. Sterility barriers over new needles greatly reduce the potential for contamination. In addition, the housed band of needles integrates storage with the pen, reducing the need for users to carry large and cumbersome kits.

Cumbersome and potentially dangerous needle attachment is made easier for the user. The device interfaces are more user friendly than the typical pen needle hub. With embodiments of the present invention, the user can interface with a familiar twist grip, inserting the needle with a twist then a pulling motion. Currently, the user must remove the top of the needle container, twist the needle onto the pen, remove the needle container, and then finally remove a needle cap. While there are some needle storage devices that aid in placing the needle hub on the pen, the user still must remove needle hub packaging, including the inner needle sheath, to place a needle hub onto a typical insulin pen. In embodiments of the present invention, the typical four meticulous steps with small sharp needle hubs have been reduced to two intuitive steps with ergonomic user interfaces.

Needle removal and disposal has been simplified with embodiments of the present invention. There are devices that aid in removing needles from pens after use, including needle clipping devices and sharps containers that pull the needle from the pen body. But these devices are more cumbersome when compared to embodiments of the present invention. One embodiment of the present invention includes an automated removal step. Additionally, by including a needle shield or sheathing, embodiments of the present invention can remove the needle from the septum after delivery and place it in used needle storage without further user input.

Several factors make embodiments of the present invention reliable. For example, the needle holder can fix the needle position. Additionally, gear teeth or axial grooves in combination with a flexible needle holder and a center snap arm can provide a simple advancement mechanism. Further, having the bottom of the device drive the needle into the septum and having the needle slide through the needle holder provides a simple engagement mechanism.

The engagement between the user gear/axial grooves and the needle holder is flexible, thereby allowing loose system tolerances, i.e., the manufacturing tolerances are not overly small. Moreover, needle straightness and alignments are not critical for proper septum engagement.

The degree of rotation of the user dial can be made large in embodiments of the present invention, to address patient dexterity issues. Further, the needle holder can ensure that the needle stays in place after a device impact, thereby making embodiments of the present invention robust.

Embodiments of the present invention can integrate the needle changing process into a single device. Needle storage, needle attachment, needle removal, and needle disposal can now be accomplished via a single system.

New needles can be located underneath the septum and attached to the pen injector's fluid system via a continuous band of needles. The band can include hubs in which the needles are slidably mounted. The user can turn this band with a dial, placing the new needle into position, and moving the used one into storage. By pulling the dial upwardly along the pen, the delivery needle then slides through the band hub and sterility barriers slide down the needle, allowing the needle to pierce the septum and expose itself for delivery.

According to one embodiment of the present invention, the needle is removed from the septum and sheathed into the device via an unlocking mechanism attached to a needle shield. This shield is compressed during needle insertion, indicating that a delivery is being made. According to one embodiment of the present invention, as the shield moves into the device, the shield unlocks a spring that was compressed during the needle attachment. This spring then releases the device to move back toward the distal end of the pen. The device has arms which pull the needle from the pen septum.

Figure 111:
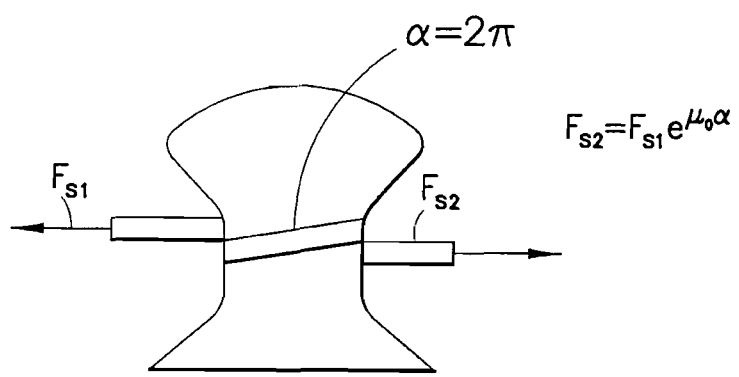
FIG. 111 is an illustration of the force of a rope winding around an anchor.

According to one embodiment of the present invention, the needle holder is pulled through a circuitous path via arms on the external user dial. According to another embodiment of the present invention, the needle holder is pulled through the circuitous path via engagement with axial slots in the user dial. According to yet another embodiment of the present invention, the needle holder is pulled through the circuitous path via engagement with a rack an opinion system. As the needle holder winds through the device, the frictional force will grow if a single arm is engaged throughout the turn. This principle is similar to a rope winding around an anchor. As shown in FIG. 111, with each degree of wrap, the force needed to pull the rope over the anchor increases.

$$F_{S2} = F_{S1} e^{\mu_0 \alpha}$$

where $F_{S1}$ is the force that needs to be pulled by the rope, $F_{S2}$ is the force needed to pull $F_{S1}$ with the rope, $\mu_0$ is the coefficient of friction, and $\alpha$ is the wrapping angle.

According to one embodiment of the present invention, flexible hub interface arms are employed to ensure that the user dial force is not excessive.

Linking the needles via a needle holder can give each needle a known position, aiding handling. The needle holder can also keep needles secure in the event of sudden shocks/impulses to the device.

In an exemplary embodiment of the present invention, each new needle, i.e., prior to being used for an injection, stored in the needle changing device is individually sterile, thereby preventing contamination of a new needle by a used needle. For example, a sterility barrier is provided for each new needle.

In another exemplary embodiment of the present invention, each used needle remains accessible such that the user has access to the used needles in case of an emergency. Alternatively, only the last needle is always accessible, thereby providing an available needle in case of emergency.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the claims and their equivalents.

What is claimed is:

1. An apparatus for storing and changing needles for a medicament delivery device having a medicament container, the apparatus comprising:
    a fixed mount adapted to connect the apparatus with the medicament delivery device;
    a needle holder displaceable along a circuitous path and connecting a plurality of needles displaceably disposed thereon;
    a guide member adapted to guide displacement of the needle holder, the guide member being disposed about the fixed mount;
    a user interface rotatably disposed about the fixed mount and having at least one internal engaging structure adapted to displace the needle holder along the circuitous path; and
    a fixed post connected with the fixed mount adapted to guide the needle holder toward an activated position;
    wherein the user interface is rotated to displace the needle holder along the circuitous path and position a selected needle in the activated position;
    wherein the guide member comprises a stabilizing member adapted to position the selected needle in the activated position; and
    wherein the fixed post comprises a lock feature adapted to selectively engage a lock ring displaceably disposed on the selected needle, to selectively prevent rotation of the user interface and displacement of the needle holder subsequent to the needle being positioned in the activated position.

2. The apparatus according to claim 1, further comprising:
    a radially displaceable second user interface, the second user interface having a foot;
    wherein the fixed mount comprises a sliding guide for guiding movement of the foot, the sliding guide having a lower stop, a lower ramp, an upper stop, and an upper ramp; and
    wherein the rotation of the user interface and displacement of the selected needle into the activated position displaces the second user interface radially outward, thereby displacing the foot from a position adjacent to the lower stop to a position adjacent to the lower ramp, and enabling proximal axial displacement of the user interface toward the medicament delivery device.

3. The apparatus according to claim 2, wherein proximal axial displacement of the user interface toward the medicament delivery device exposes a patient end of the selected needle outside of the apparatus, fluidly connects a non-patient end of the selected needle with the medicament container, displaces the lock ring relative to the selected needle, and displaces the foot over the lower ramp to a position adjacent to the upper stop, thereby preventing distal axial displacement of the user interface; and
    wherein subsequent inward radial displacement of the second user interface displaces the foot from the position adjacent to the upper stop to a position adjacent to the upper ramp, thereby enabling distal axial displacement of the user interface, which re-sheathes the selected needle within the apparatus.

4. The apparatus according to claim 3, wherein the displacement of the lock ring relative to the selected needle prevents engagement of the lock ring and the lock feature of the fixed post subsequent to re-sheathing of the selected needle, thereby enabling rotation of the user interface for selection of another needle.

5. An apparatus for storing and changing needles for a medicament delivery device having a medicament container, the apparatus comprising:
    a fixed mount adapted to connect the apparatus with the medicament delivery device;
    a needle holder displaceable along a circuitous path and connecting a plurality of needles displaceably disposed thereon;
    a guide member adapted to guide displacement of the needle holder, the guide member being disposed about the fixed mount;
    a user interface rotatably disposed about the fixed mount and having at least one internal engaging structure adapted to displace the needle holder along the circuitous path;
    a bottom housing slidable relative to the fixed mount; and
    a sterility barrier ensuring sterility of at least a patient end of each needle prior to exposure to the outside of the apparatus;
    wherein each needle comprises the patient end and a non-patient end, and has a central hub disposed thereon;
    wherein the sterility barrier for each needle comprises a pair of paper sheets disposed on opposing sides of the needle, bonded about the central hub and at a position distally spaced from a distal end of the patient end to form respective seals and a pair of lower portions, which are folded proximally at the distal bond and bonded to the needle holder; and
    wherein side edges of the paper are bonded to seal the needle within the sterility barrier.

6. The apparatus according to claim 5, wherein the sterility barriers are serially connected.

7. An apparatus for storing and changing needles for a medicament delivery device having a medicament container, the apparatus comprising:
    a fixed mount adapted to connect the apparatus with the medicament delivery device;
    a needle holder displaceable along a circuitous path and connecting a plurality of needles displaceably disposed thereon;
    a guide member adapted to guide displacement of the needle holder, the guide member being disposed about the fixed mount;

a first user interface rotatably disposed about the fixed mount and having at least one internal engaging structure adapted to displace the needle holder along the circuitous path;

a radially displaceable second user interface; and a needle counter rotatable relative to the fixed mount and the first user interface;

wherein the first user interface is rotated to displace the needle holder along the circuitous path and position a selected needle in an activated position; and wherein the rotation of the first user interface and displacement of the selected needle into the activated position displaces the second user interface radially outward, and subsequent inward radial displacement of the second user interface advances the needle counter.

8. An apparatus for storing and changing needles for a medicament delivery device having a medicament container, the apparatus comprising:

a fixed mount adapted to connect the apparatus with the medicament delivery device;

a needle holder displaceable along a circuitous path and connecting a plurality of needles displaceably disposed thereon;

a guide member adapted to guide displacement of the needle holder, the guide member being disposed about the fixed mount;

a user interface rotatably disposed about the fixed mount and having at least one internal engaging structure adapted to displace the needle holder along the circuitous path;

a bottom housing slidable relative to the fixed mount; and a sterility barrier ensuring sterility of at least a patient end of each needle prior to exposure to the outside of the apparatus;

wherein each needle comprises the patient end and a non-patient end, and has a central hub disposed thereon; and wherein the sterility barrier for each needle comprises:

a lower needle hub disposed around a portion of the patient end of the needle;

an introducer, selectively slidable relative to the lower needle hub; and a boot, selectively slidable relative to the introducer, the boot having a sterile floor at a distal end thereof;

wherein the introducer has a distal cutting tip adapted to cut a portion of the sterile floor, and a proximal shoulder adapted to engage the boot;

wherein during distal displacement of the selected needle relative to the bottom housing, subsequent to contact between the boot and a floor of the bottom housing, the introducer distally displaces relative to the boot and cuts the sterile floor; and wherein subsequent to engagement between the proximal shoulder and the boot, further distal displacement of the selected needle relative to the bottom housing distally displaces the needle hub relative to the introducer and exposes a distal end of the patient end to the outside of the apparatus.

9. An apparatus for storing and changing needles for a medicament delivery device having a medicament container, the apparatus comprising:

a fixed mount adapted to connect the apparatus with the medicament delivery device;

a needle holder displaceable along a circuitous path and connecting a plurality of needles displaceably disposed thereon;

a guide member adapted to guide displacement of the needle holder, the guide member being disposed about the fixed mount;

a user interface rotatably disposed about the fixed mount and having at least one internal engaging structure adapted to displace the needle holder along the circuitous path;

a bottom housing slidable relative to the fixed mount; and a sterility barrier ensuring sterility of at least a patient end of each needle prior to exposure to the outside of the apparatus;

wherein each needle comprises the patient end and a non-patient end, and has a central hub disposed thereon;

wherein the sterility barrier for each needle comprises a boot disposed at a distal end of the patient end of the needle; and wherein during distal displacement of the needle relative to the bottom housing, subsequent to contact between the boot and a floor of the bottom housing, the selected needle pierces a distal end of the boot and passes through an opening in the floor of the bottom housing, exposing an end of the patient portion to the outside of the apparatus.

10. An apparatus for storing and changing needles for a medicament delivery device having a medicament container, the apparatus comprising:

a fixed mount adapted to connect the apparatus with the medicament delivery device;

a needle holder displaceable along a circuitous path and connecting a plurality of needles displaceably disposed thereon;

a guide member adapted to guide displacement of the needle holder, the guide member being disposed about the fixed mount;

a user interface rotatably disposed about the fixed mount and having at least one internal engaging structure adapted to displace the needle holder along the circuitous path;

a bottom housing slidable relative to the fixed mount; and a sterility barrier ensuring sterility of at least a patient end of each needle prior to exposure to the outside of the apparatus;

wherein each needle comprises the patient end and a non-patient end, and has a central hub disposed thereon;

wherein the sterility barrier for each needle comprises a boot disposed at a proximal end of the non-patient end of the needle; and wherein during proximal displacement of the selected needle relative to the fixed mount, subsequent to contact between the boot and a septum of the medicament container, the selected needle pierces a proximal end of the boot and passes through the septum, fluidly communicating with an interior of the medicament container.

11. An apparatus for storing and changing needles for a medicament delivery device having a medicament container, the apparatus comprising:

a fixed mount adapted to connect the apparatus with the medicament delivery device;

a guide member axially slidably disposed about the fixed mount, the fixed mount and the guide member forming at least a portion of a circuitous path;

a needle holder displaceable along the circuitous path and connecting a plurality of needles displaceably disposed thereon, the circuitous path being planar and non-circular and including an activated position in which a selected needle can communicate with the medicament container; and a user interface rotatably disposed about the fixed mount and the guide member, and axially slidable relative to the fixed mount for sliding along with the guide member.

12. An apparatus for storing and changing needles for a medicament delivery device having a medicament container, the apparatus comprising:
a fixed mount adapted to connect the apparatus with the medicament delivery device;
a needle holder displaceable along a circuitous path and connecting a plurality of needles displaceably disposed thereon, the circuitous path being planar and non-circular and including an activated position in which a selected needle can communicate with the medicament container;
a guide member adapted to guide displacement of the needle holder, the guide member being disposed about the fixed mount; and
a user interface rotatably disposed about the fixed mount and having at least one internal engaging structure adapted to displace the needle holder along the circuitous path.

13. The apparatus according to claim 12, wherein each needle comprises a patient end and a non-patient end, and has a central hub disposed thereon; and
the apparatus further comprises:
a bottom housing slidable relative to the fixed mount; and
a sterility barrier ensuring sterility of at least the patient end of each needle prior to exposure to the outside of the apparatus.

14. The apparatus according to claim 12, wherein the internal engaging structure of the user interface comprises at least one axial groove.

15. The apparatus according to claim 12, wherein the internal engaging structure of the user interface comprises at least one radially inward protrusion.

16. The apparatus according to claim 12, wherein the user interface is rotated to displace the needle holder along the circuitous path and position a selected needle in the activated position.

17. The apparatus according to claim 16, wherein the activated position is on a central axis of the apparatus.

18. The apparatus according to claim 16, wherein the user interface is axially slidable relative to the fixed mount for exposing a patient end of the selected needle outside of the apparatus, fluidly connecting a non-patient end of the selected needle with the medicament container, and re-sheathing the selected needle, wherein the patient and non-patient ends of the selected needle are fluidly connected.

19. The apparatus according to claim 16, wherein the guide member comprises a stabilizing member for positioning the selected needle in the activated position.

20. The apparatus according to claim 16, further comprising a fixed post connected with the fixed mount for guiding the needle holder toward the activated position.

21. The apparatus according to claim 20, wherein the fixed mount and the fixed post are integrally formed as a unitary structure.

22. A method of selecting a needle for a medicament delivery device having a medicament container, the method comprising:
connecting the medicament delivery device with an apparatus for storing and changing needles;
rotating a first user interface of the apparatus to displace one of a plurality of needles mounted in a needle holder along a circuitous path to an activated position in which said one needle can communicate with the medicament container, and also to displace a second user interface;
proximally sliding the first user interface axially to expose a patient end of said one needle outside of the apparatus and fluidly connect a non-patient end of said one needle with the medicament container;
radially displacing the second user interface to advance a needle counter; and
distally sliding the first user interface to re-sheathe the patient end of said one needle and disconnect the non-patient end of said one needle from the medicament container.

23. The method according to claim 22, wherein rotating the first user interface to displace the second user interface enables subsequent proximal sliding of the first user interface.

24. The method according to claim 22, wherein radially displacing the second user interface to advance the needle counter enables subsequent distal sliding of the first user interface.

25. The method according to claim 22, wherein distally sliding the first user interface enables subsequent rotation of the first user interface to displace another of the plurality of needles to the activated position.

* * * * *